(12) United States Patent
Poudel et al.

(10) Patent No.: US 11,400,094 B2
(45) Date of Patent: *Aug. 2, 2022

(54) 2H-PYRAZOLO[4,3-D]PYRIMIDINE COMPOUNDS AS TOLL-LIKE RECEPTOR 7 (TLR7) AGONISTS AND METHODS AND USES THEREFOR

(71) Applicant: BRISTOL-MYERS SQUIBB COMPANY, Princeton, NJ (US)

(72) Inventors: Yam B. Poudel, Fremont, CA (US); Sanjeev Gangwar, Foster City, CA (US); Liqi He, San Jose, CA (US); Prasanna Sivaprakasam, Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 345 days.

This patent is subject to a terminal disclaimer.

(21) Appl. No.: 16/529,457

(22) Filed: Aug. 1, 2019

(65) Prior Publication Data

US 2020/0039986 A1 Feb. 6, 2020

Related U.S. Application Data

(60) Provisional application No. 62/714,238, filed on Aug. 3, 2018.

(51) Int. Cl.
| | | |
|---|---|---|
| *A61K 31/519* | (2006.01) | |
| *A61K 47/60* | (2017.01) | |
| *A61K 39/395* | (2006.01) | |
| *C07D 487/04* | (2006.01) | |
| *A61P 35/00* | (2006.01) | |
| *A61K 31/395* | (2006.01) | |

(52) U.S. Cl.
CPC .......... *A61K 31/519* (2013.01); *A61K 31/395* (2013.01); *A61K 39/3955* (2013.01); *A61K 39/39558* (2013.01); *A61K 47/60* (2017.08); *A61P 35/00* (2018.01); *C07D 487/04* (2013.01)

(58) Field of Classification Search
CPC ................ A61K 31/519; A61K 31/395; A61K 39/3955; A61K 39/39558; A61K 47/60; A61K 45/06; A61K 2300/00; A61P 35/00; C07D 487/04

See application file for complete search history.

(56) References Cited

U.S. PATENT DOCUMENTS

| | | | |
|---|---|---|---|
| 6,028,076 | A | 2/2000 | Hirota et al. |
| 6,376,501 | B1 | 4/2002 | Isobe et al. |
| 7,241,890 | B2 | 7/2007 | Kasibhatla et al. |
| 7,521,454 | B2 | 4/2009 | Isobe et al. |
| 7,642,350 | B2 | 1/2010 | Pryde |
| 7,691,877 | B2 | 4/2010 | Jones |
| 7,979,498 | B2 | 7/2011 | Melick |
| 8,148,371 | B2 | 4/2012 | Isobe et al. |
| 8,729,088 | B2 | 5/2014 | Carson et al. |
| 8,993,755 | B2 | 3/2015 | Graupe et al. |
| 9,050,376 | B2 | 6/2015 | Carson et al. |
| 9,127,006 | B2 | 9/2015 | Desai et al. |
| 9,161,934 | B2 | 10/2015 | Halcomb et al. |
| 9,173,935 | B2 | 11/2015 | Maj et al. |
| 9,295,732 | B2 | 3/2016 | Lioux et al. |
| 9,499,549 | B2 | 11/2016 | Mcgowan |
| 9,662,336 | B2 | 5/2017 | Coe |
| 9,902,730 | B2 | 2/2018 | Li et al. |
| 9,944,649 | B2 | 4/2018 | Cortez |
| 10,457,681 | B2 | 10/2019 | Young |
| 10,487,084 | B2 | 11/2019 | He et al. |
| 10,494,370 | B2 | 12/2019 | Poudel |
| 2007/0225303 | A1 | 9/2007 | Ogita et al. |
| 2009/0105212 | A1 | 4/2009 | Isobe et al. |
| 2009/0118263 | A1 | 5/2009 | Hashimoto et al. |
| 2011/0028715 | A1 | 2/2011 | Isobe et al. |
| 2012/0003298 | A1 | 1/2012 | Barberis et al. |

(Continued)

FOREIGN PATENT DOCUMENTS

| | | |
|---|---|---|
| JP | 2004137157 A | 5/2004 |
| WO | WO2007028129 A1 | 3/2007 |

(Continued)

OTHER PUBLICATIONS

Akinbobuyi et al., Facile syntheses of functionalized toll-like receptor 7 agonists, 2015, 459-460, 56, Tetrahedron Letters.

(Continued)

*Primary Examiner* — Julie Wu
*Assistant Examiner* — John L Van Druff
(74) *Attorney, Agent, or Firm* — Joseph F. Reidy; Yuan Chao

(57) ABSTRACT

Compounds according to formula II are useful as agonists of Toll-like receptor 7 (TLR7).

(II)

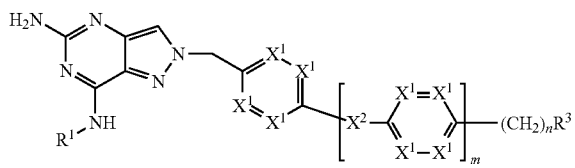

Figure 1:
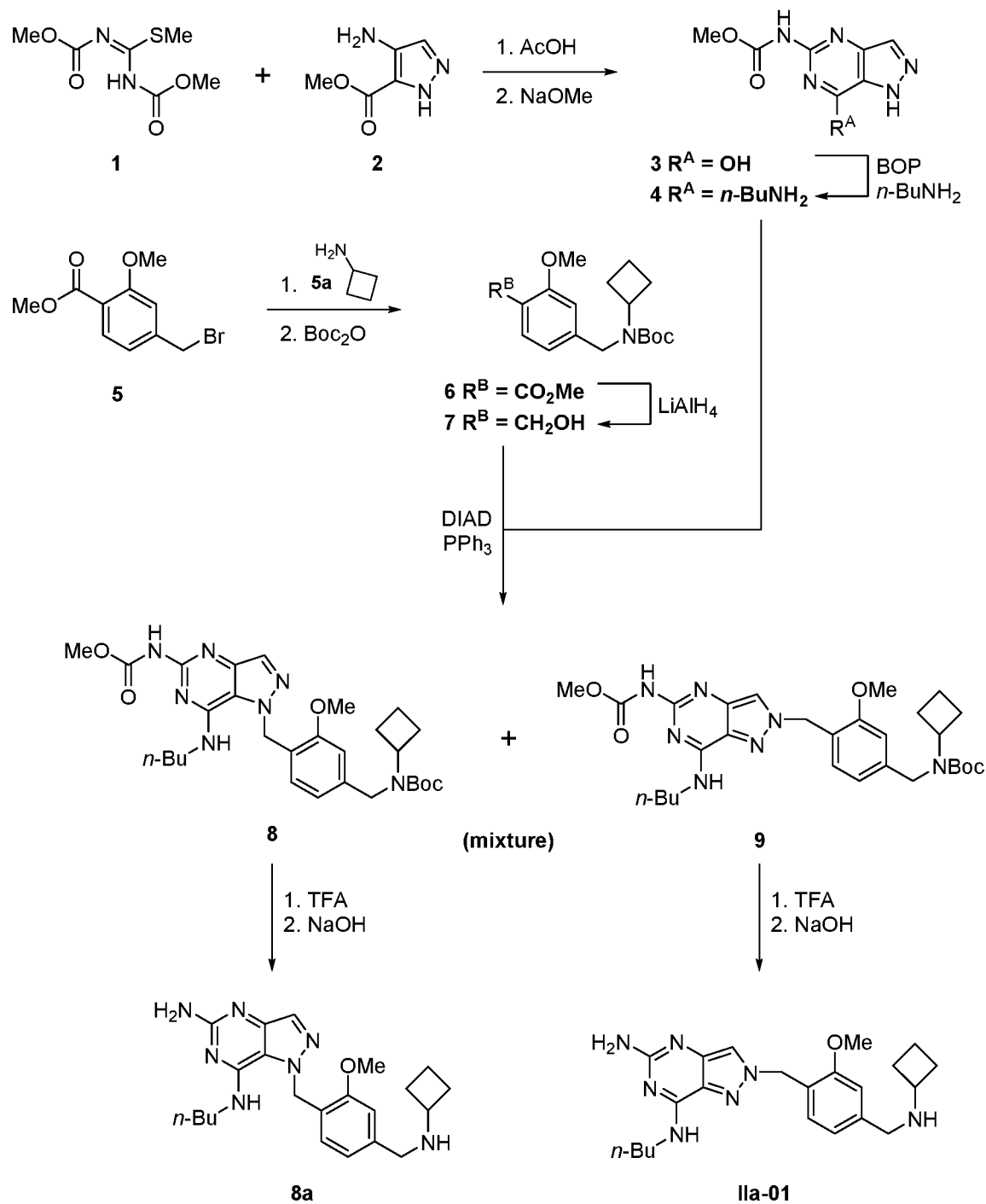

Such compounds can be used in cancer treatment, especially in combination with an anti-cancer immunotherapy agent, or as a vaccine adjuvant.

18 Claims, 8 Drawing Sheets

(56) References Cited

U.S. PATENT DOCUMENTS

| | | | |
|---|---|---|---|
| 2012/0083473 | A1 | 4/2012 | Holldack et al. |
| 2012/0231023 | A1 | 9/2012 | Zurawski et al. |
| 2012/0302598 | A1 | 11/2012 | Jones |
| 2013/0202629 | A1 | 8/2013 | Carson et al. |
| 2014/0141033 | A1 | 5/2014 | Vernejoul et al. |
| 2014/0323441 | A1 | 10/2014 | Bonfanti et al. |
| 2015/0299221 | A1 | 10/2015 | Bonfanti |
| 2016/0168150 | A1 | 6/2016 | McGowan |
| 2016/0199499 | A1 | 7/2016 | Carson et al. |
| 2017/0121421 | A1 | 5/2017 | Cortez et al. |
| 2017/0273983 | A1 | 9/2017 | Tianqing et al. |
| 2019/0055245 | A1 | 2/2019 | Poudel |
| 2019/0055246 | A1 | 2/2019 | He |
| 2019/0055247 | A1 | 2/2019 | He |
| 2020/0038403 | A1* | 2/2020 | Poudel .................. A61K 47/60 |

FOREIGN PATENT DOCUMENTS

| | | | |
|---|---|---|---|
| WO | WO2015036044 | A1 | 3/2015 |
| WO | WO-2015171527 | A1 * | 11/2015 ........... C07D 487/04 |
| WO | WO2016107536 | A1 | 7/2016 |
| WO | WO2017076346 | A1 | 5/2017 |
| WO | WO2017216293 | A1 | 12/2017 |
| WO | WO2018095426 | A1 | 5/2018 |
| WO | WO2019124500 | A1 | 6/2019 |
| WO | WO2019209811 | A1 | 10/2019 |

OTHER PUBLICATIONS

Akinbobuyi et al., Synthesis and immunostimulatory activity of substituted TLR7 agonists, 2016, 4246-4249, 26, Bioorganic & Medicinal Chemistry Letters.

Beesu et al., Identification of High-Potency Human TLR8 and Dual TLR7/TLR8 Agonists in Pyrimidine-2,4-diamines, 2017, 2084-2098, 60, J Med Chem.

Berghofer et al., Natural and Synthetic TLR7 Ligands Inhibit CpG-A- and CpG-C-Oligodeoxynucleotide-Induced IFN . . . , 2007, 4072-4079, 178, The Journal of Immunology.

Chan et al., Synthesis and Characterization of PEGylated Toll Like Receptor 7 Ligands, 2011, 445-454, 22, Bioconugate Chemistry.

Chan et al., Synthesis and Immunological Characterization of Toll-Like Receptor 7 Agonistic Conjugates, 2009, 1194-_1200, vol. 20, Bioconjugate Chemistry.

Cortez et al., Recent Advances in Small-Molecule TLR7 Agonists for Drug Discovery, 2018, 481_502, Medicinal Chemistry Reviews.

Embrechts et al., 2,4-Diaminoquinazolines as Dual Toll-like Receptor (TLR) 7/8 Modulators for the Treatment of Hepatitis B Virus, 2018, 6236_6246, 61, Journal of Medicinal Chemistry.

Gadd et al., Targeted Activation of Toll-Like Receptors: Conjugation of a Toll-Like Receptor 7 Agonist to a Monoclonal Antibody Maintains Antigen Binding and Specificity, 2015, 1743_1752, 26, Bioconjugate Chemistry.

Isobe et al., Synthesis and Biological Evaluation of Novel 9-Substituted-8-Hydroxyadenine Derivatives as Potent Interferon Inducers, 2006, 2088-2095, 49, J Med Chem.

Koga-Yamakawa et al., Intratracheal and oral administration of SM-276001: A selective TLR7 agonist, leads to antitumor efficacy in primary and metastatic models of cancer, 2013, 580-590, 132, IJC Cancer.

Lund et al., Recognition of single-stranded RNA viruses by Toll-like receptor 7, 2004, 5598-5603, 101:15, ProcNatlAcadSciUSA.

McGowan et al., Identification and Optimization of Pyrrolo[3,2-d]pyrimidine Toll-like Receptor 7 (TLR7) Selective Agonists for the Treatment of Hepatitis B, 2017, 6137-6151, 60, J Med Chem.

Musmuca et al., Small-Molecule Interferon Inducers. Toward the Comprehension of the Molecular Determinants through Ligand-Based Approaches, 2009, 1777-1786,49, J Chem Inform Model.

PCT International Search Report, dated Oct. 9, 2019, ISA EP.

Nakamira et al., Synthesis and evaluation of 8-oxoadenine derivatives as potent Toll-like receptor 7 agonists with high water solubility, 2013, 669-672, 23, BioorgMedChemLett.

Sato-Kaneko et al., Combination Immunotherapy With TLR Agonists and Checkpoint Inhibitors Suppresses Head and Neck Cancer, 2017, 93397, 2:18, JCI Insight.

Smitts et al., The Use of TLR7 and TLR8 Ligands for the Enhancement of Cancer Immunotherapy, 2008, 859_875, 13, The Oncologist.

Vakslakos et al., The use of Toll-like receptor 7/8 agonists as vaccine adjuvants, 2013, 809_819, 12_7, Expert Review of Vaccines.

Yoshiaki et al., JP2004137157_ABSTRACT, 2004, NA.

Yu et al., Toll-Like Receptor 7 Agonists: Chemical Feature Based Pharmacophore Identification and Molecular Docking Studies, 2013, 1-12, PLOSSONE.

Zhang et al., Structural Analysis Reveals that Toll-like Receptor 7 Is a Dual Receptor for Guanosine and Single-Stranded RNA, 2016, 737_748, 45, Immunity.

* cited by examiner

2H-PYRAZOLO[4,3-D]PYRIMIDINE COMPOUNDS AS TOLL-LIKE RECEPTOR 7 (TLR7) AGONISTS AND METHODS AND USES THEREFOR

CROSS-REFERENCE TO RELATED APPLICATIONS

This application claims the benefit under 35 U.S.C. § 119(e) of U.S. Provisional Application Ser. No. 62/714,238, filed Aug. 3, 2018; the disclosure of which is incorporated herein by reference.

BACKGROUND OF THE DISCLOSURE

This disclosure relates to Toll-like receptor 7 ("TLR7") agonists and conjugates thereof, and methods for the preparation and use of such agonists and their conjugates.

Toll-like receptors ("TLRs") are receptors that recognize pathogen-associated molecular patterns ("PAMPs"), which are small molecular motifs conserved in certain classes of pathogens. TLRs can be located either on a cell's surface or intracellularly. Activation of a TLR by the binding of its cognate PAMP signals the presence of the associated pathogen inside the host—i.e., an infection—and stimulates the host's immune system to fight the infection. Humans have 10 TLRs, named TLR1, TLR2, TLR3, and so on.

The activation of a TLR—with TLR7 being the most studied—by an agonist can have a positive effect on the action of vaccines and immunotherapy agents in treating a variety of conditions other than actual pathogen infection, by stimulating the immune response overall. Thus, there is considerable interest in the use of TLR7 agonists as vaccine adjuvants or as enhancers in cancer immunotherapy. See, for example, Vasilakos and Tomai 2013, Sato-Kaneko et al. 2017, Smits et al. 2008, and Ota et al. 2019.

TLR7, an intracellular receptor located on the membrane of endosomes, recognizes PAMPs associated with single-stranded RNA viruses. Its activation induces secretion of Type I interferons such as IFNα and IFNβ (Lund et al. 2004). TLR7 has two binding sites, one for single stranded RNA ligands (Berghöfer et al. 2007) and one for small molecules such as guanosine (Zhang et al. 2016).

TLR7 can bind to, and be activated by, guanosine-like synthetic agonists such as imiquimod, resiquimod, and gardiquimod, which are based on a 1H-imidazo[4,5-c]quinoline scaffold. For a review of small-molecule TLR7 agonists, see Cortez and Va 2018.

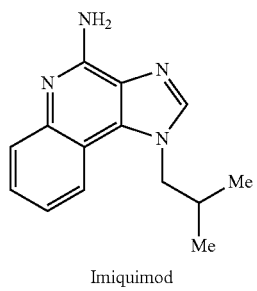

Imiquimod

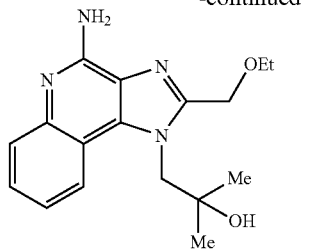

Resiquimod

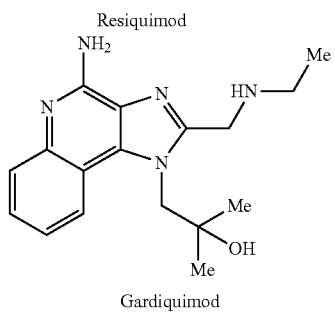

Gardiquimod

Synthetic TLR7 agonists based on a pteridinone molecular scaffold are also known, as exemplified by vesatolimod (Desai et al. 2015).

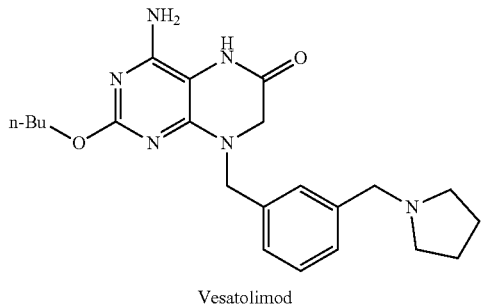

Vesatolimod

Other synthetic TLR7 agonists based on a purine-like scaffold have been disclosed, frequently according to the general formula (A):

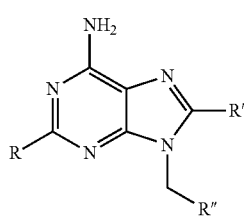

(A)

where R, R', and R" are structural variables, with R" typically containing an unsubstituted or substituted aromatic or heteroaromatic ring.

Disclosures of bioactive molecules having a purine-like scaffold and their uses in treating conditions such as fibrosis, inflammatory disorders, cancer, or pathogenic infections include: Akinbobuyi et al. 2015 and 2016; Barberis et al. 2012; Carson et al. 2014; Ding et al. 2016, 2017a, and 2017b; Graupe et al. 2015; Hashimoto et al. 2009; He et al.

2019a and 2019b; Holldack et al. 2012; Isobe et al. 2009a and 2012; Poudel et al. 2019a and 2019b; Pryde 2010; and Young et al. 2019.

The group R" can be pyridyl: Bonfanti et al. 2015a and 2015b; Halcomb et al. 2015; Hirota et al. 2000; Isobe et al. 2002, 2004, 2006, 2009a, 2009b, 2011, and 2012; Kasibhatla et al. 2007; Koga-Yamakawa et al. 2013; Musmuca et al. 2009; Nakamura 2012; Ogita et al. 2007; and Yu et al. 2013.

There are disclosures of related molecules in which the 6,5-fused ring system of formula (A)—a pyrimidine six member ring fused to an imidazole five member ring—is modified. (a) Dellaria et al. 2007, Jones et al. 2010 and 2012, and Pilatte et al. 2017 disclose compounds in which the pyrimidine ring is replaced by a pyridine ring. (b) Chen et al. 2011, Coe et al. 2017, and Zhang et al. 2018 disclose compounds in which the imidazole ring is replaced by a pyrazole ring. (c) Cortez et al. 2017 and 2018; Li et al. 2018; and McGowan et al. 2016a, 2016b, and 2017 disclose compounds in which the imidazole ring is replaced by a pyrrole ring.

Bonfanti et al. 2015b and 2016 and Purandare et al. 2019 disclose TLR7 modulators in which the two rings of a purine moiety are spanned by a macrocycle:

A TLR7 agonist can be conjugated to a partner molecule, which can be, for example, a phospholipid, a poly(ethylene glycol) ("PEG"), an antibody, or another TLR (commonly TLR2). Exemplary disclosures include: Carson et al. 2013, 2015, and 2016, Chan et al. 2009 and 2011, Cortez et al. 2017, Gadd et al. 2015, Lioux et al. 2016, Maj et al. 2015, Vernejoul et al. 2014, and Zurawski et al. 2012. A frequent conjugation site is at the R" group of formula (A).

Jensen et al. 2015 discloses the use of cationic lipid vehicles for the delivery of TLR7 agonists.

Some TLR7 agonists, including resiquimod are dual TLR7/TLR8 agonists. See, for example, Beesu et al. 2017, Embrechts et al. 2018, Lioux et al. 2016, and Vernejoul et al. 2014.

Full citations for the documents cited herein by first author or inventor and year are listed at the end of this specification.

BRIEF SUMMARY OF THE DISCLOSURE

This specification relates to compounds having a 2H-pyrazolo[4,3-d]pyrimidine aromatic system, having activity as TLR7 agonists

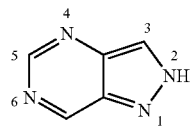

2H-pyrazolo[4,3-d]pyrimidine

In one aspect, there is provided a compound with a structure according to formula II

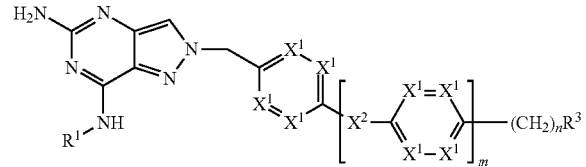

wherein
each $X^1$ is independently N or $CR^2$;
$X^2$ is O, $CH_2$, NH, S, or $N(C_1-C_3$ alkyl);
$R^1$ is H, $CH_3(CH_2)_{1-3}$, $CH_3(CH_2)_{0-1}O(CH_2)_{2-3}$, $CH_3(CH_2)_{0-3}C(=O)$, $CH_3(CH_2)_{0-1}O(CH_2)_{2-3}C(=O)$,

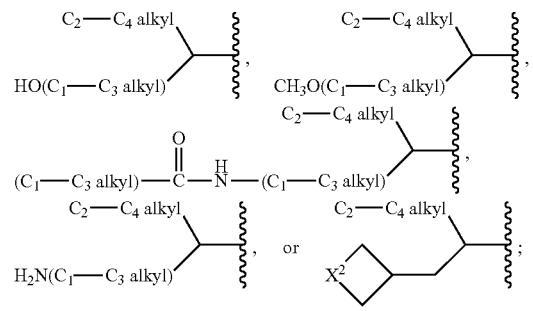

$R^2$ is H, $O(C_1-C_3$ alkyl), $C_1-C_3$ alkyl, Cl, F, or CN;
$R^3$ is H, halo, OH, CN, $NH_2$, $NH(C_1-C_5$ alkyl), $N(C_1-C_5$ alkyl)$_2$, $NH(CH_2)_{0-1}(C_3-C_6$ cycloalkyl), $NH(C_4-C_8$ bicycloalkyl), $NH(C_6-C_{10}$ spirocycloalkyl), $N(C_3-C_6$ cycloalkyl)$_2$, $NH(CH_2)_{1-3}(aryl)$, $N((CH_2)_{1-3}(aryl))_2$, a cyclic amine moiety having the structure

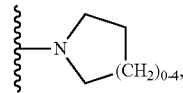

a 6-membered aromatic or heteroaromatic moiety or a 5-membered heteroaromatic moiety;
wherein
an alkyl, cycloalkyl, bicycloalkyl, spirocycloalkyl, cyclic amine, 6-membered aromatic or heteroaromatic, or 5-membered heteroaromatic moiety is optionally substituted with one or more substituents selected from OH, halo, CN, $(C_1-C_3$ alkyl), $O(C_1-C_3$ alkyl), $C(=O)$ (Me), $SO_2(C_1-C_3$ alkyl), $C(=O)(Et)$, $NH_2$, NH(Me), $N(Me)_2$, NH(Et), $N(Et)_2$, and $N(C_1-C_3$ alkyl), $(CH_2)_{1-2}OH$, $(CH_2)_{1-2}OMe$; and
a cycloalkyl, bicycloalkyl, spirocycloalkyl, or cyclic amine moiety may have a $CH_2$ group replaced by O, S, $SO_2$, NH, $C(=O)$, $N(C_1-C_3$ alkyl), $NC(=O)(C_1-C_3$ alkyl), or N(Boc);
m is 0 or 1;
and
n is 1, 2, or 3.

Compounds disclosed herein have activity as TLR7 agonists and some can be conjugated to an antibody for targeted delivery to a target tissue or organ of intended action. They can also be PEGylated, to modulate their pharmaceutical properties.

Compounds disclosed herein, or their conjugates or their PEGylated derivatives, can be used to treat a subject suffering from a condition amenable to treatment by activation of the immune system, by administering to such subject a therapeutically effective amount of such a compound or a conjugate thereof or a PEGylated derivative thereof, especially in combination with a vaccine or a cancer immunotherapy agent.

BRIEF DESCRIPTION OF THE DRAWING(S)

FIGS. 1, 2A, 2B, 3, 4A, and 4B show reaction schemes for preparing compounds disclosed herein.

Figure 5:
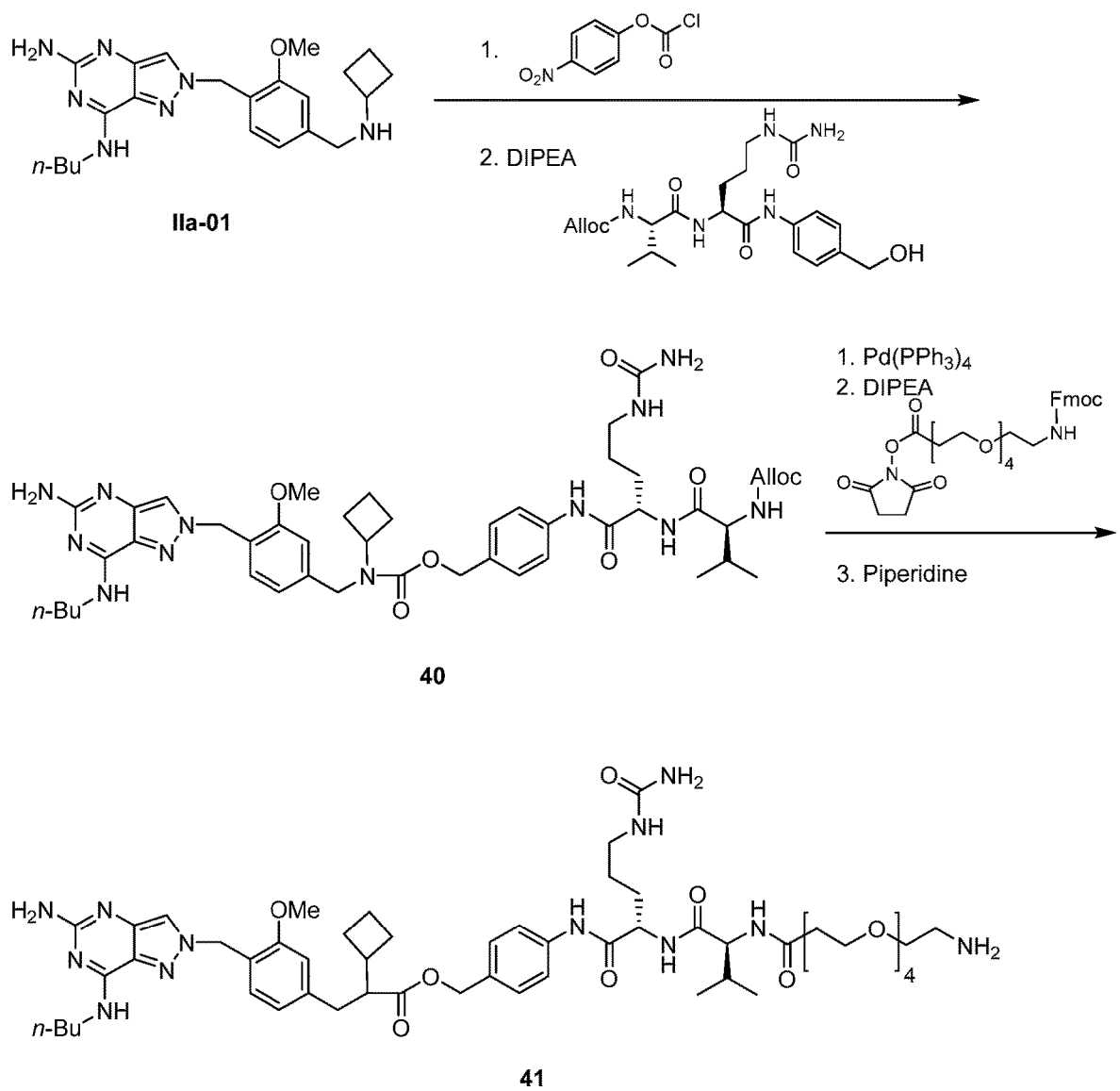
Figure 6:
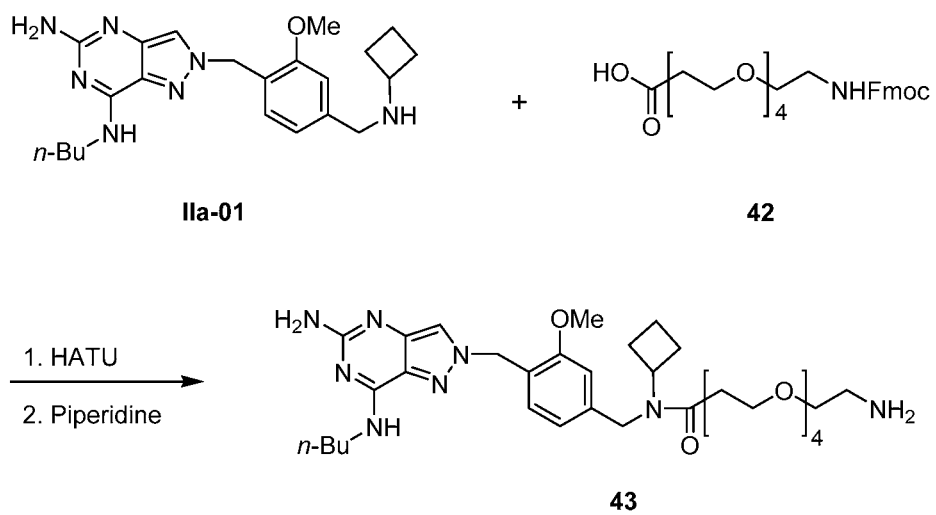

FIGS. 5 and 6 show schemes for the attachment of linkers to compounds of this disclosure, rendering them suitable for conjugation.

DETAILED DESCRIPTION OF THE INVENTION

Definitions

"Antibody" means whole antibodies and any antigen binding fragment (i.e., "antigen-binding portion") or single chain variants thereof. A whole, or full length, antibody is a protein comprising at least two heavy (H) chains and two light (L) chains inter-connected by disulfide bonds. Each heavy chain comprises a heavy chain variable region ($V_H$) and a heavy chain constant region comprising three domains, $C_{H1}$, $C_{H2}$ and $C_{H3}$. Each light chain comprises a light chain variable region ($V_L$ or $V_k$) and a light chain constant region comprising one single domain, $C_L$. The $V_H$ and $V_L$ regions can be further subdivided into regions of hypervariability, termed complementarity determining regions (CDRs), interspersed with more conserved framework regions (FRs). Each $V_H$ and $V_L$ comprises three CDRs and four FRs, arranged from amino- to carboxy-terminus in the following order: FR1, CDR1, FR2, CDR2, FR3, CDR3, and FR4. The variable regions contain a binding domain that interacts with an antigen. The constant regions may mediate the binding of the antibody to host tissues or factors, including various cells of the immune system (e.g., effector cells) and the first component (Clq) of the classical complement system. An antibody is said to "specifically bind" to an antigen X if the antibody binds to antigen X with a $K_D$ of $5 \times 10^{-8}$ M or less, more preferably $1 \times 10^{-8}$ M or less, more preferably $6 \times 10^{-9}$ M or less, more preferably $3 \times 10^{-9}$ M or less, even more preferably $2 \times 10^{-9}$ M or less. The antibody can be chimeric, humanized, or, preferably, human. The heavy chain constant region can be engineered to affect glycosylation type or extent, to extend antibody half-life, to enhance or reduce interactions with effector cells or the complement system, or to modulate some other property. The engineering can be accomplished by replacement, addition, or deletion of one or more amino acids or by replacement of a domain with a domain from another immunoglobulin type, or a combination of the foregoing.

"Antigen binding fragment" and "antigen binding portion" of an antibody (or simply "antibody portion" or "antibody fragment") mean one or more fragments of an antibody that retain the ability to specifically bind to an antigen. It has been shown that the antigen-binding function of an antibody can be performed by fragments of a full-length antibody, such as (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fab' fragment, which is essentially an Fab with part of the hinge region (see, for example, Abbas et al., *Cellular and Molecular Immunology*, 6th Ed., Saunders Elsevier 2007); (iv) a Fd fragment consisting of the $V_H$ and Cm domains; (v) a Fv fragment consisting of the $V_L$ and $V_H$ domains of a single arm of an antibody, (vi) a dAb fragment (Ward et al., (1989) *Nature* 341:544-546), which consists of a $V_H$ domain; (vii) an isolated complementarity determining region (CDR); and (viii) a nanobody, a heavy chain variable region containing a single variable domain and two constant domains. Preferred antigen binding fragments are Fab, F(ab')2, Fab', Fv, and Fd fragments. Furthermore, although the two domains of the Fv fragment, $V_L$ and $V_H$, are encoded by separate genes, they can be joined, using recombinant methods, by a synthetic linker that enables them to be made as a single protein chain in which the $V_L$ and $V_H$ regions pair to form monovalent molecules (known as single chain Fv, or scFv); see, e.g., Bird et al. (1988) *Science* 242:423-426; and Huston et al. (1988) *Proc. Natl. Acad. Sci. USA* 85:5879-5883). Such single chain antibodies are also encompassed within the term "antigen-binding portion" of an antibody.

Unless indicated otherwise—for example by reference to the linear numbering in a SEQ ID NO: listing—references to the numbering of amino acid positions in an antibody heavy or light chain variable region ($V_H$ or $V_L$) are according to the Kabat system (Kabat et al., "Sequences of proteins of immunological interest, 5th ed., Pub. No. 91-3242, U.S. Dept. Health & Human Services, NIH, Bethesda, Md., 1991, hereinafter "Kabat") and references to the numbering of amino acid positions in an antibody heavy or light chain constant region ($C_{H1}$, $C_{H2}$, $C_{H3}$, or $C_L$) are according to the EU index as set forth in Kabat. See Lazar et al., US 2008/0248028 A1, the disclosure of which is incorporated herein by reference, for examples of such usage. Further, the ImMunoGeneTics Information System (IMGT) provides at its website a table entitled "IMGT Scientific Chart: Correspondence between C Numberings" showing the correspondence between its numbering system, EU numbering, and Kabat numbering for the heavy chain constant region.

An "isolated antibody" means an antibody that is substantially free of other antibodies having different antigenic specificities (e.g., an isolated antibody that specifically binds antigen X is substantially free of antibodies that specifically bind antigens other than antigen X). An isolated antibody that specifically binds antigen X may, however, have cross-reactivity to other antigens, such as antigen X molecules from other species. In certain embodiments, an isolated antibody specifically binds to human antigen X and does not cross-react with other (non-human) antigen X antigens. Moreover, an isolated antibody may be substantially free of other cellular material and/or chemicals.

"Monoclonal antibody" or "monoclonal antibody composition" means a preparation of antibody molecules of single molecular composition, which displays a single binding specificity and affinity for a particular epitope.

"Human antibody" means an antibody having variable regions in which both the framework and CDR regions (and the constant region, if present) are derived from human germline immunoglobulin sequences. Human antibodies may include later modifications, including natural or synthetic modifications. Human antibodies may include amino acid residues not encoded by human germline immunoglobulin sequences (e.g., mutations introduced by random or site-specific mutagenesis in vitro or by somatic mutation in vivo). However, "human antibody" does not include antibodies in which CDR sequences derived from the germline of another mammalian species, such as a mouse, have been grafted onto human framework sequences.

"Human monoclonal antibody" means an antibody displaying a single binding specificity, which has variable regions in which both the framework and CDR regions are derived from human germline immunoglobulin sequences. In one embodiment, human monoclonal antibodies are produced by a hybridoma that includes a B cell obtained from a transgenic nonhuman animal, e.g., a transgenic mouse, having a genome comprising a human heavy chain transgene and a light chain transgene fused to an immortalized cell.

"Aliphatic" means a straight- or branched-chain, saturated or unsaturated, non-aromatic hydrocarbon moiety having the specified number of carbon atoms (e.g., as in "$C_3$ aliphatic," "$C_{1-5}$ aliphatic," "$C_1$-$C_5$ aliphatic," or "$C_1$ to $C_5$ aliphatic," the latter three phrases being synonymous for an aliphatic moiety having from 1 to 5 carbon atoms) or, where the number of carbon atoms is not explicitly specified, from 1 to 4 carbon atoms (2 to 4 carbons in the instance of unsaturated aliphatic moieties). A similar understanding is applied to the number of carbons in other types, as in $C_2$-4 alkene, $C_4$-$C_7$ cycloaliphatic, etc. In a similar vein, a term such as "$(CH_2)_{1-3}$" is to be understand as shorthand for the subscript being 1, 2, or 3, so that such term represents $CH_2$, $CH_2CH_2$, and $CH_2CH_2CH_2$.

"Alkyl" means a saturated aliphatic moiety, with the same convention for designating the number of carbon atoms being applicable. By way of illustration, $C_1$-$C_4$ alkyl moieties include, but are not limited to, methyl, ethyl, propyl, isopropyl, isobutyl, t-butyl, 1-butyl, 2-butyl, and the like. "Alkylene" means a divalent counterpart of an alkyl group, such as $CH_2CH_2$, $CH_2CH_2CH_2$, and $CH_2CH_2CH_2CH_2$.

"Alkenyl" means an aliphatic moiety having at least one carbon-carbon double bond, with the same convention for designating the number of carbon atoms being applicable. By way of illustration, $C_2$-$C_4$ alkenyl moieties include, but are not limited to, ethenyl (vinyl), 2-propenyl (allyl or prop-2-enyl), cis-1-propenyl, trans-1-propenyl, E- (or Z-) 2-butenyl, 3-butenyl, 1,3-butadienyl (but-1,3-dienyl) and the like.

"Alkynyl" means an aliphatic moiety having at least one carbon-carbon triple bond, with the same convention for designating the number of carbon atoms being applicable. By way of illustration, $C_2$-$C_4$ alkynyl groups include ethynyl (acetylenyl), propargyl (prop-2-ynyl), 1-propynyl, but-2-ynyl, and the like.

"Cycloaliphatic" means a saturated or unsaturated, non-aromatic hydrocarbon moiety having from 1 to 3 rings, each ring having from 3 to 8 (preferably from 3 to 6) carbon atoms. "Cycloalkyl" means a cycloaliphatic moiety in which each ring is saturated. "Cycloalkenyl" means a cycloaliphatic moiety in which at least one ring has at least one carbon-carbon double bond. "Cycloalkynyl" means a cycloaliphatic moiety in which at least one ring has at least one carbon-carbon triple bond. By way of illustration, cycloaliphatic moieties include, but are not limited to, cyclopropyl, cyclobutyl, cyclopentyl, cyclopentenyl, cyclohexyl, cyclohexenyl, cycloheptyl, cyclooctyl, and adamantyl. Preferred cycloaliphatic moieties are cycloalkyl ones, especially cyclopropyl, cyclobutyl, cyclopentyl, and cyclohexyl. "Cycloalkylene" means a divalent counterpart of a cycloalkyl group. Similarly, "bicycloalkylene" and "spirocycloalkylene" (or "spiroalkylene") refer to divalent counterparts of a bicycloalkyl and spirocycloalkyl/spiroalkyl group.

"Heterocycloaliphatic" means a cycloaliphatic moiety wherein, in at least one ring thereof, up to three (preferably 1 to 2) carbons have been replaced with a heteroatom independently selected from N, O, or S, where the N and S optionally may be oxidized and the N optionally may be quaternized. Preferred cycloaliphatic moieties consist of one ring, 5- to 6-membered in size. Similarly, "heterocycloalkyl," "heterocycloalkenyl," and "heterocycloalkynyl" means a cycloalkyl, cycloalkenyl, or cycloalkynyl moiety, respectively, in which at least one ring thereof has been so modified. Exemplary heterocycloaliphatic moieties include aziridinyl, azetidinyl, 1,3-dioxanyl, oxetanyl, tetrahydrofuryl, pyrrolidinyl, piperidinyl, piperazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolanyl, tetrahydro-1,1-dioxothienyl, 1,4-dioxanyl, thietanyl, and the like. "Heterocycloalkylene" means a divalent counterpart of a heterocycloalkyl group.

"Alkoxy," "aryloxy," "alkylthio," and "arylthio" mean —O(alkyl), —O(aryl), —S(alkyl), and —S(aryl), respectively. Examples are methoxy, phenoxy, methylthio, and phenylthio, respectively.

"Halogen" or "halo" means fluorine, chlorine, bromine or iodine, unless a narrower meaning is indicated.

"Aryl" means a hydrocarbon moiety having a mono-, bi-, or tricyclic ring system (preferably monocyclic) wherein each ring has from 3 to 7 carbon atoms and at least one ring is aromatic. The rings in the ring system may be fused to each other (as in naphthyl) or bonded to each other (as in biphenyl) and may be fused or bonded to non-aromatic rings (as in indanyl or cyclohexylphenyl). By way of further illustration, aryl moieties include, but are not limited to, phenyl, naphthyl, tetrahydronaphthyl, indanyl, biphenyl, phenanthryl, anthracenyl, and acenaphthyl. "Arylene" means a divalent counterpart of an aryl group, for example 1,2-phenylene, 1,3-phenylene, or 1,4-phenylene.

"Heteroaryl" means a moiety having a mono-, bi-, or tricyclic ring system (preferably 5- to 7-membered monocyclic) wherein each ring has from 3 to 7 carbon atoms and at least one ring is an aromatic ring containing from 1 to 4 heteroatoms independently selected from from N, O, or S, where the N and S optionally may be oxidized and the N optionally may be quaternized. Such at least one heteroatom containing aromatic ring may be fused to other types of rings (as in benzofuranyl or tetrahydroisoquinolyl) or directly bonded to other types of rings (as in phenylpy-ridyl or 2-cyclopentylpyridyl). By way of further illustration, heteroaryl moieties include pyrrolyl, furanyl, thiophenyl (thienyl), imidazolyl, pyrazolyl, oxazolyl, isoxazolyl, thiazolyl, isothiazolyl, triazolyl, tetrazolyl, pyridyl, N-oxopyridyl, pyridazinyl, pyrimidinyl, pyrazinyl, quinolinyl, isoquinolynyl, quinazolinyl, cinnolinyl, quinozalinyl, naphthyridinyl, benzofuranyl, indolyl, benzothiophenyl, oxadiazolyl, thiadiazolyl, phenothiazolyl, benzimidazolyl, benzotriazolyl, dibenzofuranyl, carbazolyl, dibenzothiophenyl, acridinyl, and the like. "Heteroarylene" means a divalent counterpart of a heteroaryl group.

Where it is indicated that a moiety may be substituted, such as by use of "unsubstituted or substituted" or "optionally substituted" phrasing as in "unsubstituted or substituted $C_1$-$C_5$ alkyl" or "optionally substituted heteroaryl," such moiety may have one or more independently selected substituents, preferably one to five in number, more preferably one or two in number. Substituents and substitution patterns can be selected by one of ordinary skill in the art, having regard for the moiety to which the substituent is attached, to provide compounds that are chemically stable and that can be synthesized by techniques known in the art as well as the methods set forth herein. Where a moiety is identified as being "unsubstituted or substituted" or "optionally substituted," in a preferred embodiment such moiety is unsubstituted.

"Arylalkyl," (heterocycloaliphatic)alkyl," "arylalkenyl," "arylalkynyl," "biarylalkyl," and the like mean an alkyl, alkenyl, or alkynyl moiety, as the case may be, substituted with an aryl, heterocycloaliphatic, biaryl, etc., moiety, as the case may be, with the open (unsatisfied) valence at the alkyl, alkenyl, or alkynyl moiety, for example as in benzyl, phenethyl, N-imidazoylethyl, N-morpholinoethyl, and the like. Conversely, "alkylaryl," "alkenylcycloalkyl," and the like mean an aryl, cycloalkyl, etc., moiety, as the case may be, substituted with an alkyl, alkenyl, etc., moiety, as the case may be, for example as in methylphenyl (tolyl) or allylcyclohexyl. "Hydroxyalkyl," "haloalkyl," "alkylaryl," "cyanoaryl," and the like mean an alkyl, aryl, etc., moiety, as the case may be, substituted with one or more of the identified substituent (hydroxyl, halo, etc., as the case may be).

For example, permissible substituents include, but are not limited to, alkyl (especially methyl or ethyl), alkenyl (especially allyl), alkynyl, aryl, heteroaryl, cycloaliphatic, heterocycloaliphatic, halo (especially fluoro), haloalkyl (especially trifluoromethyl), hydroxyl, hydroxyalkyl (especially hydroxyethyl), cyano, nitro, alkoxy, —O(hydroxyalkyl), —O(haloalkyl) (especially —OCF$_3$), —O(cycloalkyl), —O(heterocycloalkyl), —O(aryl), alkylthio, arylthio, =O, =NH, =N(alkyl), =NOH, =NO(alkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), —SO$_2$N(alkyl)$_2$, and the like.

Where the moiety being substituted is an aliphatic moiety, preferred substituents are aryl, heteroaryl, cycloaliphatic, heterocycloaliphatic, halo, hydroxyl, cyano, nitro, alkoxy, —O(hydroxyalkyl), —O(haloalkyl), —O(cycloalkyl), —O(heterocycloalkyl), —O(aryl), alkylthio, arylthio, =O, =NH, =N(alkyl), =NOH, =NO(alkyl), —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(=O)alkyl, —S(cycloalkyl), —SO$_2$(alkyl), —SO$_2$NH$_2$, —SO$_2$NH(alkyl), and —SO$_2$N(alkyl)$_2$. More preferred substituents are halo, hydroxyl, cyano, nitro, alkoxy, —O(aryl), =O, =NOH, =NO(alkyl), —OC(=O)(alkyl), —OC(=O)O(alkyl), —OC(=O)NH$_2$, —OC(=O)NH(alkyl), —OC(=O)N(alkyl)$_2$, azido, —NH$_2$, —NH(alkyl), —N(alkyl)$_2$, —NH(aryl), —NHC(=O)(alkyl), —NHC(=O)H, —NHC(=O)NH$_2$, —NHC(=O)NH(alkyl), —NHC(=O)N(alkyl)$_2$, and —NHC(=NH)NH$_2$. Especially preferred are phenyl, cyano, halo, hydroxyl, nitro, C$_1$-C$_4$alkyoxy, O(C$_2$-C$_4$ alkylene)OH, and O(C$_2$-C$_4$ alkylene)halo.

Where the moiety being substituted is a cycloaliphatic, heterocycloaliphatic, aryl, or heteroaryl moiety, preferred substituents are alkyl, alkenyl, alkynyl, halo, haloalkyl, hydroxyl, hydroxyalkyl, cyano, nitro, alkoxy, —O(hydroxyalkyl), —O(haloalkyl), —O(aryl), —O(cycloalkyl), —O(heterocycloalkyl), alkylthio, arylthio, —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O)(alkyl), —OC(=O)(hydroxyalkyl), —OC(=O)O(alkyl), —OC(=O)O(hydroxyalkyl), —OC(=O)NH$_2$, —OC(=O) NH(alkyl), —OC(=O)N(alkyl)$_2$, azido, —NH$_2$, —NH(alkyl), —N(alkyl)$_2$, —NH(aryl), —NH(hydroxyalkyl), —NHC(=O)(alkyl), —NHC(=O)H, —NHC(=O)NH$_2$, —NHC(=O)NH(alkyl), —NHC(=O)N(alkyl)$_2$, —NHC(=NH)NH$_2$, —OSO$_2$(alkyl), —SH, —S(alkyl), —S(aryl), —S(cycloalkyl), —S(=O)alkyl, —SO$_2$(alkyl), —SO$_2$NH$_2$, —SO$_2$NH(alkyl), and —SO$_2$N(alkyl)$_2$. More preferred substituents are alkyl, alkenyl, halo, haloalkyl, hydroxyl, hydroxyalkyl, cyano, nitro, alkoxy, —O(hydroxyalkyl), —C(=O)(alkyl), —C(=O)H, —CO$_2$H, —C(=O)NHOH, —C(=O)O(alkyl), —C(=O)O(hydroxyalkyl), —C(=O)NH$_2$, —C(=O)NH(alkyl), —C(=O)N(alkyl)$_2$, —OC(=O) (alkyl), —OC(=O)(hydroxyalkyl), —OC(=O)O(alkyl), —OC(=O)O(hydroxyalkyl), —OC(=O)NH$_2$, —OC(=O) NH(alkyl), —OC(=O)N(alkyl)$_2$, —NH$_2$, —NH(alkyl), —N(alkyl)$_2$, —NH(aryl), —NHC(=O)(alkyl), —NHC (=O)H, —NHC(=O)NH$_2$, —NHC(=O)NH(alkyl), —NHC(=O)N(alkyl)$_2$, and —NHC(=NH)NH$_2$. Especially preferred are C$_1$-C$_4$ alkyl, cyano, nitro, halo, and C$_1$-C$_4$alkoxy.

Where a range is stated, as in "C$_1$-C$_5$ alkyl" or "5 to 10%," such range includes the end points of the range, as in C$_1$ and C$_5$ in the first instance and 5% and 10% in the second instance.

Unless particular stereoisomers are specifically indicated (e.g., by a bolded or dashed bond at a relevant stereocenter in a structural formula, by depiction of a double bond as having E or Z configuration in a structural formula, or by use stereochemistry-designating nomenclature or symbols), all stereoisomers are included within the scope of the invention, as pure compounds as well as mixtures thereof. Unless otherwise indicated, racemates, individual enantiomers (whether optically pure or partially resolved), diastereomers, geometrical isomers, and combinations and mixtures thereof are all encompassed by this invention.

Those skilled in the art will appreciate that compounds may have tautomeric forms (e.g., keto and enol forms), resonance forms, and zwitterionic forms that are equivalent to those depicted in the structural formulae used herein and that the structural formulae encompass such tautomeric, resonance, or zwitterionic forms.

"Pharmaceutically acceptable ester" means an ester that hydrolyzes in vivo (for example in the human body) to produce the parent compound or a salt thereof or has per se activity similar to that of the parent compound. Suitable esters include C$_1$-C$_5$ alkyl, C$_2$-C$_5$ alkenyl or C$_2$-C$_5$ alkynyl esters, especially methyl, ethyl or n-propyl.

"Pharmaceutically acceptable salt" means a salt of a compound suitable for pharmaceutical formulation. Where a compound has one or more basic groups, the salt can be an acid addition salt, such as a sulfate, hydrobromide, tartrate, mesylate, maleate, citrate, phosphate, acetate, pamoate (embonate), hydroiodide, nitrate, hydrochloride, lactate, methylsulfate, fumarate, benzoate, succinate, mesylate, lactobionate, suberate, tosylate, and the like. Where a compound has one or more acidic groups, the salt can be a salt such as a calcium salt, potassium salt, magnesium salt, meglumine salt, ammonium salt, zinc salt, piperazine salt, tromethamine salt, lithium salt, choline salt, diethylamine salt, 4-phenylcyclohexylamine salt, benzathine salt, sodium salt, tetramethylammonium salt, and the like. Polymorphic crystalline forms and solvates are also encompassed within the scope of this invention.

"Subject" refers to an animal, including, but not limited to, a primate (e.g., human), monkey, cow, pig, sheep, goat, horse, dog, cat, rabbit, rat, or mouse. The terms "subject" and "patient" are used interchangeably herein in reference, for example, to a mammalian subject, such as a human.

The terms "treat," "treating," and "treatment," in the context of treating a disease or disorder, are meant to include alleviating or abrogating a disorder, disease, or condition, or one or more of the symptoms associated with the disorder, disease, or condition; or to slowing the progression, spread or worsening of a disease, disorder or condition or of one or more symptoms thereof. The "treatment of cancer", refers to one or more of the following effects: (1) inhibition, to some extent, of tumor growth, including, (i) slowing down and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

In the formulae of this specification, a wavy line ( ~~~~ ) transverse to a bond or an asterisk (*) at the end of the bond denotes a covalent attachment site. For instance, a statement that R is

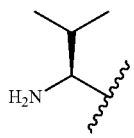

or that R is

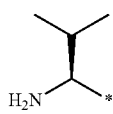

in the formula

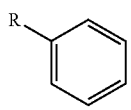

means

In the formulae of this specification, a bond traversing an aromatic ring between two carbons thereof means that the group attached to the bond may be located at any of the positions of the aromatic ring made available by removal of the hydrogen that is implicitly there. By way of illustration, the formula

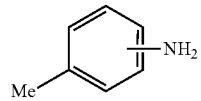

represents

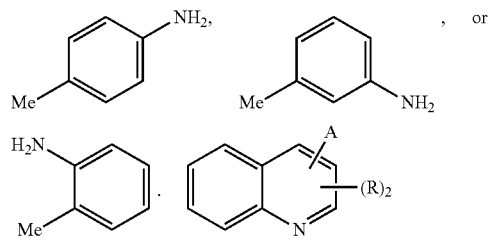

In other illustrations, represents

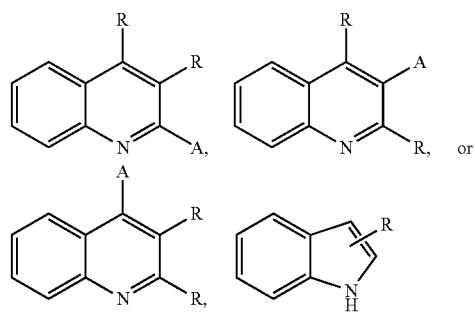

and

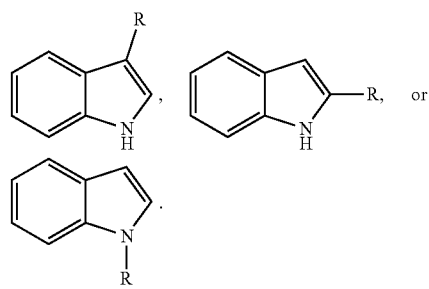

represents

Those skilled in the art will appreciate that certain structures can be drawn in one tautomeric form or another—for example, keto versus enol—and that the two forms are equivalent.

Compounds

In one embodiment, either each $X^1$ is $CR^2$ or not more than two $X^1$'s are N in the moiety

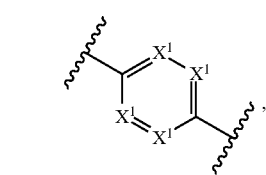
preferably
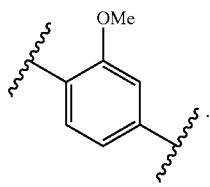 [SMILES: *c1ccc(*)c(OC)c1]
Preferably the group R¹ is
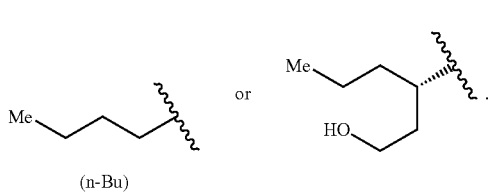 [SMILES: *CCCC ; *[C@@H](CCC)CCO]
Examples of R³ include Cl, OH,
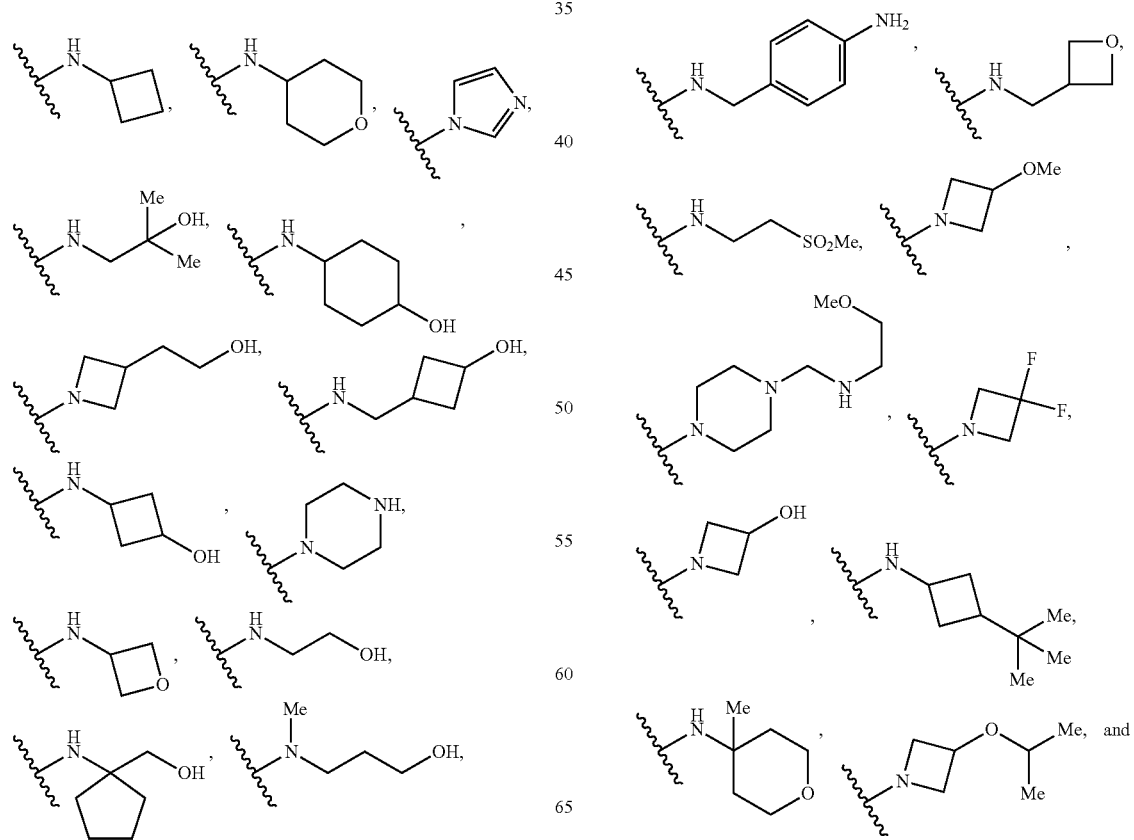

-continued

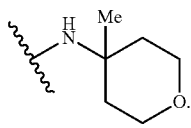

Examples of where the group $R^3$ has the structure

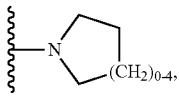

(including instances with one or more methylene (CH$_2$) groups optionally replaced by one or more of O, S, SO$_2$, NH, C(=O), N(C$_1$-C$_3$ alkyl), NC(=O)(C$_1$-C$_3$ alkyl), or N(Boc), or has another ring fused thereto, as disclosed hereinabove) are:

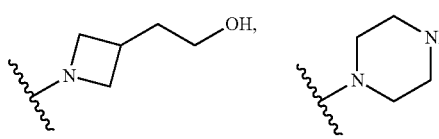

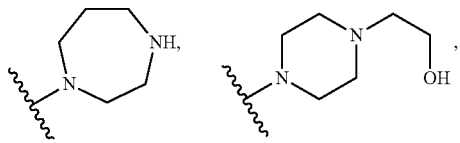

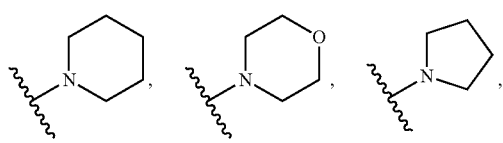

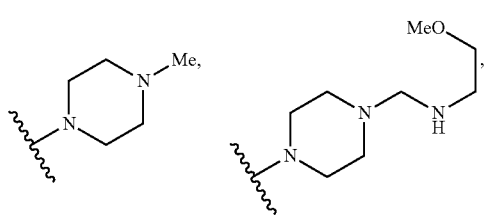

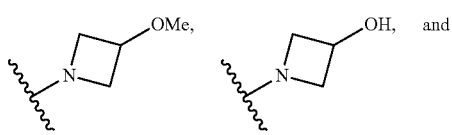

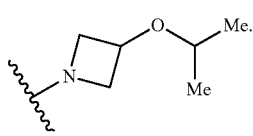

In another embodiment, $R^3$ is selected from the group consisting of

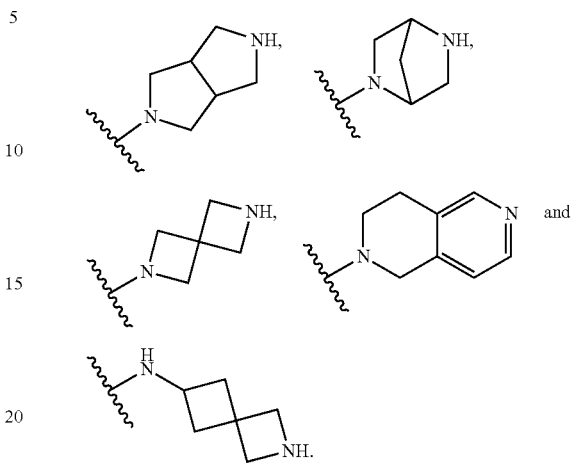

In one embodiment of formulae II, m is 0, in which case it simplifies to II':

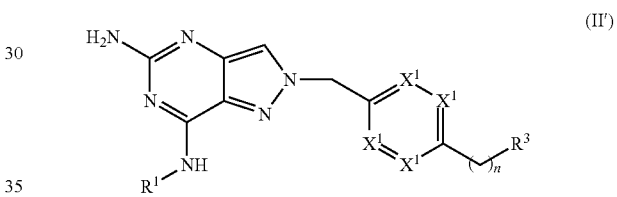

(II')

In formula II, preferably

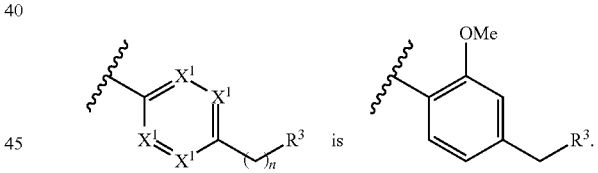

An embodiment of compounds according to formula II is represented by formula IIa, wherein $R^1$ and $R^3$ are as defined in respect of formula II hereinabove. Examples of such compounds are shown in Table A. Table A includes biological activity data for TLR7 agonism activity using the HEK-Blue™ TLR7 reporter assay, as described hereinbelow. For comparison, the activities of resiquimod and gardiquimod are also presented.

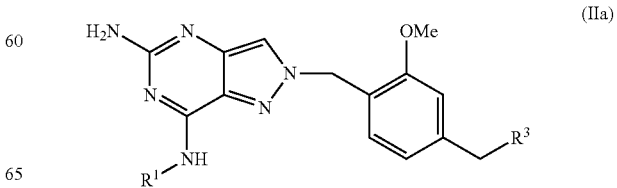

(IIa)

TABLE A

| Compound No. | TLR7 EC$_{50}$ (nM) | Structure |
|---|---|---|
| Resiquimod | 450 | 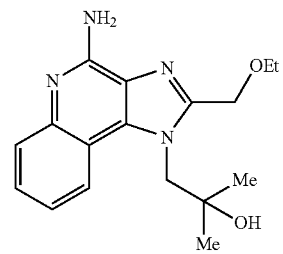 [SMILES: CCOCc1nc2c(N)nc3ccccc3c2n1CC(C)(C)O] |
| Gardiquimod | 3,300 | 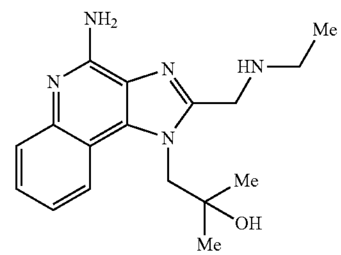 [SMILES: CCNCc1nc2c(N)nc3ccccc3c2n1CC(C)(C)O] |
| IIa-01 | 340 | 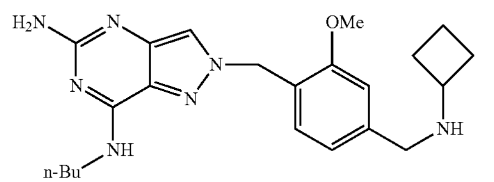 |
| IIa-02 | 510 | 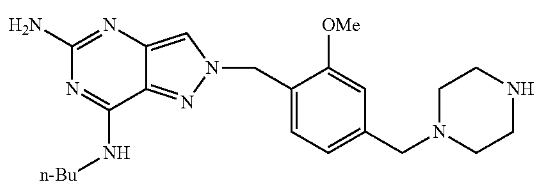 |
| IIa-03 | 1,000 | 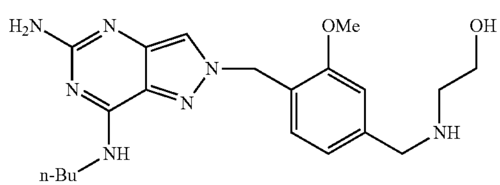 |
| IIa-04 | 1,600 | 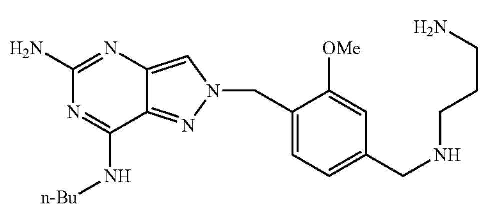 |
| IIa-05 | 450 | 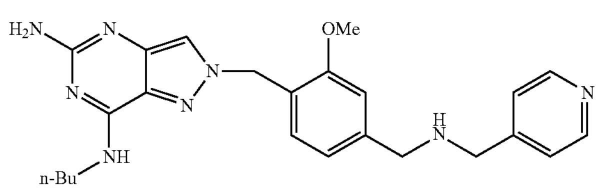 |

TABLE A-continued

Formula IIa compounds

| Compound No. | TLR7 EC$_{50}$ (nM) | Structure |
|---|---|---|
| IIa-06 | 5,000 | 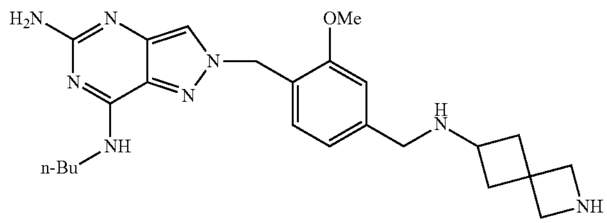 |
| IIa-07 | 610 | 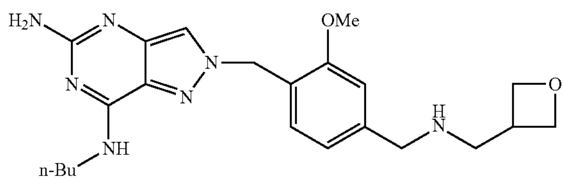 |
| IIa-08 | 650 | 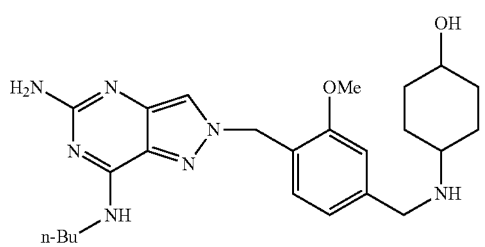 |
| IIa-09 | 420 | 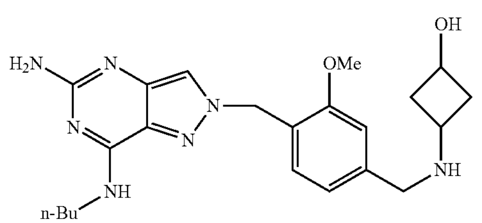 |
| IIa-10 | 270 | 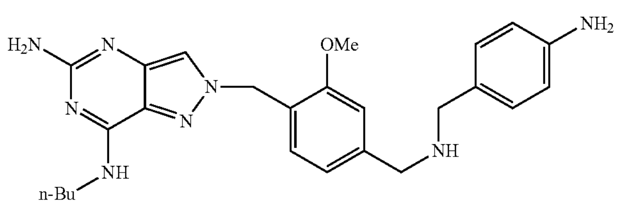 |
| IIa-11 | 540 | 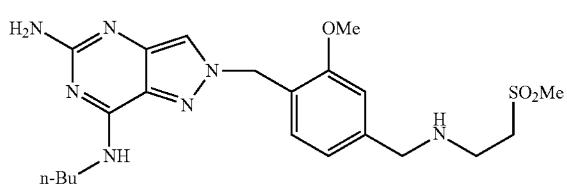 |
| IIa-12 | 840 | 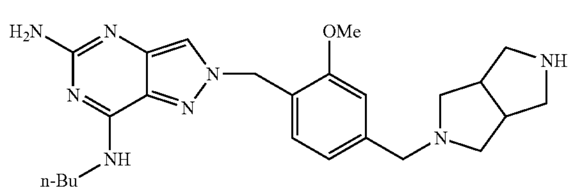 |

TABLE A-continued

Formula IIa compounds

| Compound No. | TLR7 EC$_{50}$ (nM) | Structure |
| --- | --- | --- |
| IIa-14 | 550 | 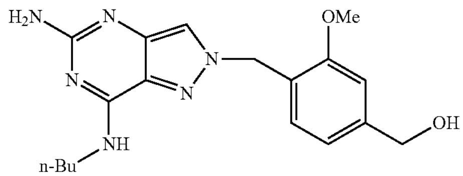 |
| IIa-15 | 300 | 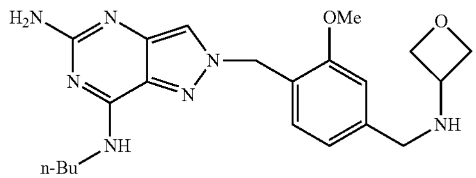 |
| IIa-17 | 180 | 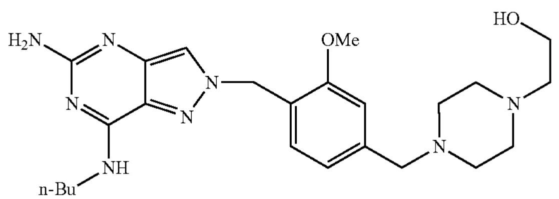 |
| IIa-18 | 520 | 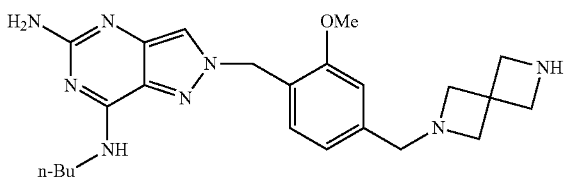 |
| IIa-19 | 320 | 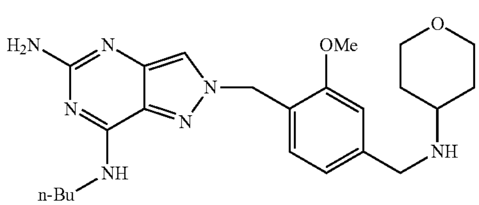 |
| IIa-20 | 280 | 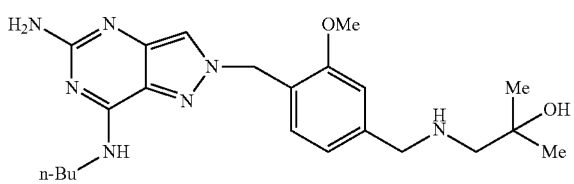 |
| IIa-21 | 190 | 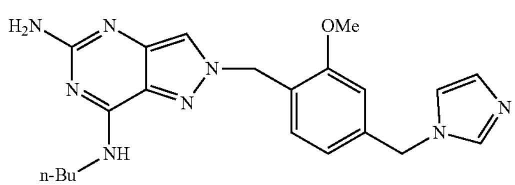 |
| IIa-22 | 200 | 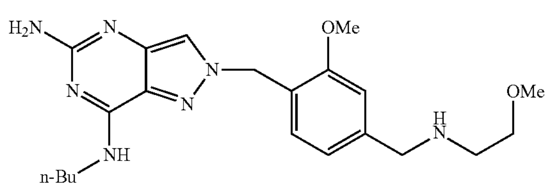 |

TABLE A-continued

Formula IIa compounds

| Compound No. | TLR7 EC$_{50}$ (nM) | Structure |
|---|---|---|
| IIa-23 | 303 | 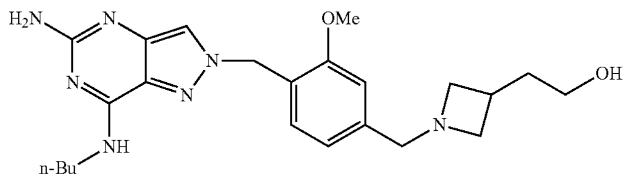 |
| IIa-24 | 130 | 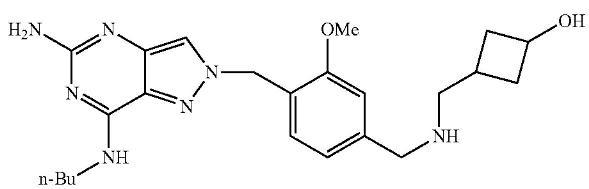 |
| IIa-25 | 880 | 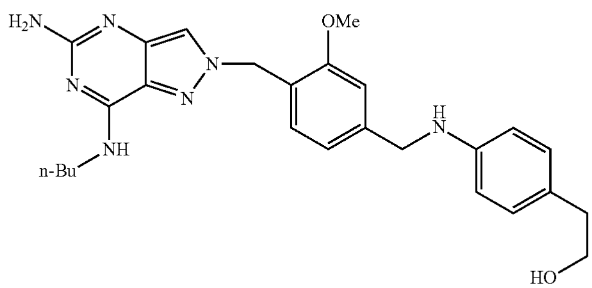 |
| IIa-26 | 194 | 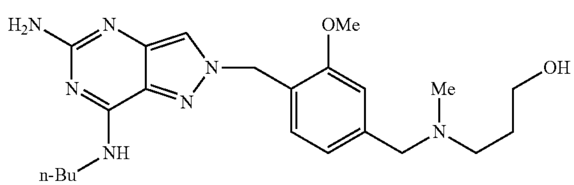 |
| IIa-27 | 710 | 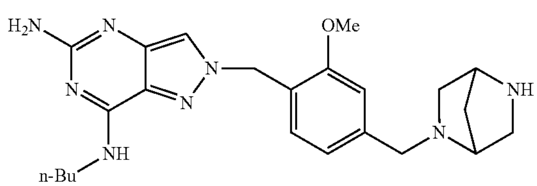 |
| IIa-28 | 430 | 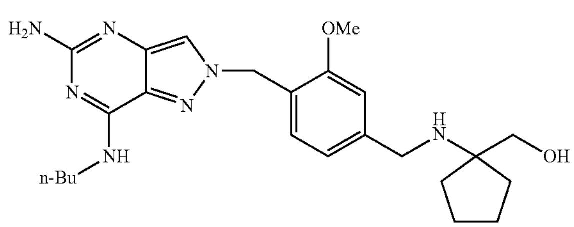 |
| IIa-29 | 760 | 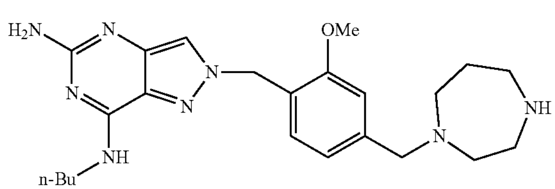 |

TABLE A-continued

Formula IIa compounds

| Compound No. | TLR7 EC$_{50}$ (nM) | Structure |
|---|---|---|
| IIa-30 | 580 | pyrazolopyrimidine with 5-NH$_2$, 7-NHn-Bu, 2-N-CH$_2$-(2-OMe-4-(morpholinomethyl)phenyl) |
| IIa-31 | 410 | pyrazolopyrimidine with 5-NH$_2$, 7-NHn-Bu, 2-N-CH$_2$-(2-OMe-4-(piperidinomethyl)phenyl) |
| IIa-32 | 600 | pyrazolopyrimidine with 5-NH$_2$, 7-NHn-Bu, 2-N-CH$_2$-(2-OMe-4-(pyrrolidinomethyl)phenyl) |
| IIa-33 | 810 | pyrazolopyrimidine with 5-NH$_2$, 7-NHn-Bu, 2-N-CH$_2$-(2-OMe-4-(n-butylaminomethyl)phenyl) |
| IIa-34 | 550 | pyrazolopyrimidine with 5-NH$_2$, 7-NHn-Bu, 2-N-CH$_2$-(2-OMe-4-(t-butylaminomethyl)phenyl) |
| IIa-35 | 2,100 | pyrazolopyrimidine with 5-NH$_2$, 7-NH-((S)-1-hydroxypentan-3-yl), 2-N-CH$_2$-(2-OMe-4-(hydroxymethyl)phenyl) |
| IIa-36 | 520 | pyrazolopyrimidine with 5-NH$_2$, 7-NHn-Bu, 2-N-CH$_2$-(2-OMe-4-((4-methylpiperazin-1-yl)methyl)phenyl) |

An embodiment of compounds according to formula II wherein m is 1 is represented by formula IIb, wherein $R^1$, $R^3$ and $X^1$ are as defined in respect of formula II hereinabove.
Preferably, in formula IIb
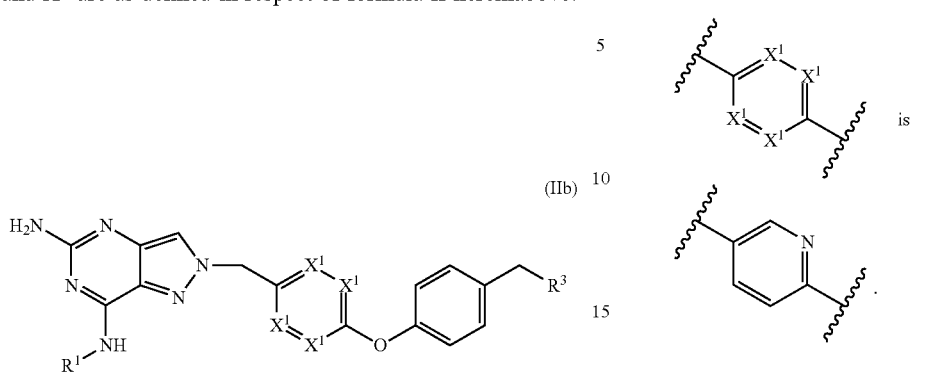
Examples of compounds according to formula IIb are shown in Table B:
TABLE B
| Compound No. | TLR7 EC$_{50}$ (nM) | Structure |
|---|---|---|
| IIb-01 | 820 | 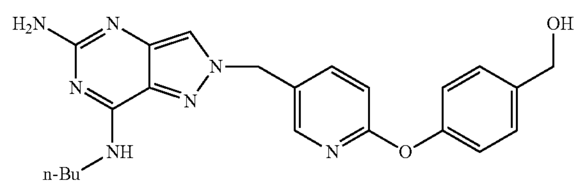 |
| IIb-02 | 1,600 | 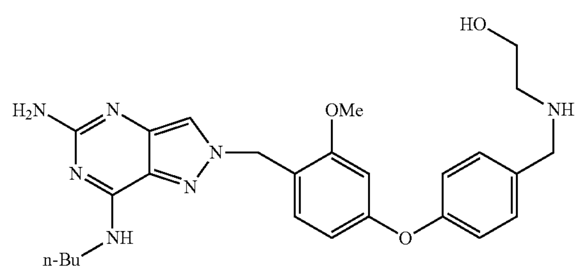 |
| IIb-03 | 5,000 | 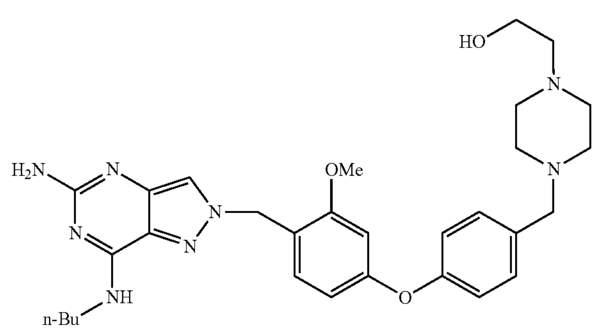 |

TABLE B-continued

Formula IIb compounds

| Compound No. | TLR7 EC$_{50}$ (nM) | Structure |
|---|---|---|
| IIb-04 | 2100 | 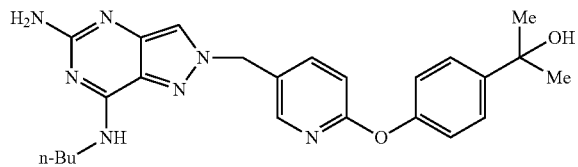 |

This specification further discloses compound III-02 (EC$_{50}$ 5,000 nM).

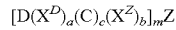

Conjugates
General

TLR7 agonists disclosed herein can be delivered to the site of intended action by localized administration or by targeted delivery in a conjugate with a targeting moiety. Preferably, the targeting moiety is an antibody or antigen binding portion thereof and its antigen is found at the locality of intended action, for example a tumor associated antigen if the intended site of action is at a tumor (cancer). Preferably, the tumor associated antigen is uniquely expressed or overexpressed by the cancer cell, compared to a normal cell. The tumor associated antigen can be located on the surface of the cancer cell or secreted by the cancer cell into its environs.

In one aspect, there is provided a conjugate comprising compound of this invention and a ligand, represented by formula (IV)

$$[D(X^D)_a(C)_c(X^Z)_b]_m Z \quad\quad (IV)$$

where Z is a targeting moiety, D is an agonist of this invention, and —(X$^D$)$_a$C(X$^Z$)$_b$— are collectively referred to as a "linker moiety" or "linker" because they link Z and D. Within the linker, C is a cleavable group designed to be cleaved at or near the site of intended biological action of D; X$^D$ and X$^Z$ are spacer moieties (or "spacers") that space apart D and C and C and Z, respectively; subscripts a, b, and c are independently 0 or 1 (that is, the presence of X$^D$, X$_Z$ and C are optional). Subscript m is 1, 2, 3, 4, 5, 6, 7, 8, 9, or 10 (preferably 1, 2, 3, or 4). D, X$_D$, C, X$_Z$ and Z are more fully described hereinbelow.

By binding to a target tissue or cell where its antigen or receptor is located, Z directs the conjugate there. Cleavage of group C at the target tissue or cell releases D to exert its effect locally. In this manner, precise delivery of D is achieved at the site of intended action, reducing the dosage needed. Also, D is normally biologically inactive (or significantly less active) in its conjugated state, thereby reducing off-target effects.

As reflected by the subscript m, each Z can conjugate with more than one D, depending on the number of sites Z has available for conjugation and the experimental conditions employed. Those skilled in the art will appreciate that, while each individual Z is conjugated to an integer number of Ds, a preparation of the conjugate may analyze for a non-integer ratio of D to Z, reflecting a statistical average. This ratio is referred to as the substitution ratio ("SR") or the drug-antibody ratio ("DAR").

Targeting Moiety Z

Preferably, targeting moiety Z is an antibody. For convenience and brevity and not by way of limitation, the detailed discussion in this specification about Z and its conjugates is written in the context of its being an antibody, but those skilled in the art will understand that other types of Z can be conjugated, mutatis mutandis. For example, conjugates with folic acid as the targeting moiety can target cells having the folate receptor on their surfaces (Leamon et al., Cancer Res. 2008, 68 (23), 9839). For the same reasons, the detailed discussion in this specification is primarily written in terms of a 1:1 ratio of Z to D (m=1).

Antibodies that can be used in conjugates of this invention include those recognizing the following antigens: mesothelin, prostate specific membrane antigen (PSMA), CD19, CD22, CD30, CD70, B7H3, B7H4 (also known as O8E), protein tyrosine kinase 7 (PTK7), glypican-3, RG1, fucosyl-GM1, CTLA-4, and CD44. The antibody can be animal (e.g., murine), chimeric, humanized, or, preferably, human. The antibody preferably is monoclonal, especially a monoclonal human antibody. The preparation of human monoclonal antibodies against some of the aforementioned antigens is disclosed in Korman et al., U.S. Pat. No. 8,609,816 B2 (2013; B7H4, also known as O8E; in particular antibodies 2A7, 1G11, and 2F9); Rao-Naik et al., 8,097,703 B2 (2012; CD19; in particular antibodies 5G7, 13F1, 46E8, 21D4, 21D4a, 47G4, 27F3, and 3C10); King et al., U.S. Pat. No. 8,481,683 B2 (2013; CD22; in particular antibodies 12C5, 19A3, 16F7, and 23C6); Keler et al., U.S. Pat. No. 7,387,776 B2 (2008; CD30; in particular antibodies 5F11, 2H9, and 17G1); Terrett et al., U.S. Pat. No. 8,124,738 B2 (2012; CD70; in particular antibodies 2H5, 10B4, 8B5, 18E7, and 69A7); Korman et al., U.S. Pat. No. 6,984,720 B1 (2006; CTLA-4; in particular antibodies 10D1, 4B6, and 1E2); Korman et al., U.S. Pat. No. 8,008,449 B2 (2011; PD-1; in particular antibodies 17D8, 2D3, 4H1, 5C4, 4A11, 7D3, and 5F4); Huang et al., US 2009/0297438 A1 (2009; PSMA. in particular antibodies 1C3, 2A10, 2F5, 2C6); Cardarelli et al., U.S. Pat. No. 7,875,278 B2 (2011; PSMA; in particular antibodies 4A3, 7F12, 8C12, 8A11, 16F9, 2A10, 2C6, 2F5, and 1C3); Terrett et al., U.S. Pat. No. 8,222,375 B2 (2012; PTK7; in particular antibodies 3G8, 4D5, 12C6, 12C6a, and 7C8); Harkins et al., U.S. Pat. No. 7,335,748 B2 (2008; RG1; in particular antibodies A, B, C, and D); Terrett et al., U.S. Pat. No. 8,268,970 B2 (2012; mesothelin; in particular antibodies 3C10, 6A4, and 7B1); Xu et al., US 2010/0092484 A1 (2010; CD44; in particular antibodies 14G9.B8.B4, 2D1.A3.D12, and 1A9.A6.B9); Deshpande et al., U.S. Pat. No. 8,258,266 B2 (2012; IP10; in particular antibodies 1D4, 1E1, 2G1, 3C4, 6A5, 6A8, 7C10, 8F6, 10A12, 10A12S, and 13C4); Kuhne et al., U.S. Pat. No. 8,450,464 B2 (2013; CXCR4; in particular antibodies F7, F9, D1, and E2); and Korman et al., U.S. Pat. No. 7,943,743 B2 (2011; PD-L1; in particular antibodies 3G10, 12A4, 10A5, 5F8, 10H10, 1B12, 7H1, 11E6, 12B7, and 13G4); the disclosures of which are incorporated herein by reference. Preferably, the antibody is an anti-mesothelin antibody.

In addition to being an antibody, Z can also be an antibody fragment (such as Fab, Fab', F(ab')$_2$, Fd, or Fv) or antibody mimetic, such as an affibody, a domain antibody (dAb), a nanobody, a unibody, a DARPin, an anticalin, a versabody, a duocalin, a lipocalin, or an avimer.

Any one of several different reactive groups on Z can be a conjugation site, including ε-amino groups in lysine residues, pendant carbohydrate moieties, carboxylic acid groups on aspartic or glutamic acid side chains, cysteine-cysteine disulfide groups, and cysteine thiol groups. For reviews on antibody reactive groups suitable for conjugation, see, e.g., Garnett, *Adv. Drug Delivery Rev.* 2001, 53, 171-216 and Dubowchik and Walker, *Pharmacology & Therapeutics* 1999, 83, 67-123, the disclosures of which are incorporated herein by reference.

Most antibodies have multiple lysine residues, which can be conjugated via their ε-amino groups via amide, urea, thiourea, or carbamate bonds.

A thiol (—SH) group in the side chain of a cysteine can be used to form a conjugate by several methods. It can be used to form a disulfide bond between it and a thiol group on the linker. Another method is via its Michael addition to a maleimide group on the linker.

Typically, although antibodies have cysteine residues, they lack free thiol groups because all their cysteines are engaged in intra- or inter-chain disulfide bonds. To generate a free thiol group, a native disulfide group can be reduced. See, e.g., Packard et al., *Biochemistry* 1986, 25, 3548; King et al., *Cancer Res.* 1994, 54, 6176; and Doronina et al., *Nature Biotechnol.* 2003, 21, 778. Alternatively, a cysteine having a free —SH group can be introduced by mutating the antibody, substituting a cysteine for another amino acid or inserting one into the polypeptide chain. See, for example, Eigenbrot et al., U.S. Pat. No. 7,521,541 B2 (2009); Chilkoti et al., *Bioconjugate Chem.* 1994, 5, 504; Urnovitz et al., U.S. Pat. No. 4,698,420 (1987); Stimmel et al., *J. Biol. Chem.* 2000, 275, 30445; Bam et al., U.S. Pat. No. 7,311,902 B2 (2007); Kuan et al., *J. Biol. Chem.* 1994, 269, 7610; Poon et al., *J. Biol. Chem.* 1995, 270, 8571; Junutula et al., *Nature Biotechnology* 2008, 26, 925 and Rajpal et al., U.S. Provisional Application No. 62/270,245, filed Dec. 21, 2015. In yet another approach, a cysteine is added to the C-terminus of the heavy of light chain. See, e.g., Liu et al., U.S. Pat. No. 8,865,875 B2 (2014); Cumber et al., *J. Immunol.* 1992, 149, 120; King et al, *Cancer Res.* 1994, 54, 6176; Li et al., *Bioconjugate Chem.* 2002, 13, 985; Yang et al., *Protein Engineering* 2003, 16, 761; and Olafson et al., *Protein Engineering Design &Selection* 2004, 17, 21. The disclosures of the documents cited in this paragraph are incorporated herein by reference.

Linkers and Their Components

As noted above, the linker comprises up to three elements: a cleavable group C and optional spacers $X_Z$ and $X^D$.

Group C is cleavable under physiological conditions. Preferably it is relatively stable while the conjugate is in circulation in the blood, but is readily cleaved once the conjugate reaches its site of intended action.

A preferred group C is a peptide that is cleaved selectively by a protease inside the target cell, as opposed to by a protease in the serum. Typically, the peptide comprises from 1 to 20 amino acids, preferably from 1 to 6 amino acids, more preferably from 2 to 3 amino acids. The amino acid(s) can be natural and/or non-natural α-amino acids. Natural amino acids are those encoded by the genetic code, as well as amino acids derived therefrom, e.g., hydroxyproline, γ-carboxyglutamate, citrulline, and O-phosphoserine. In this specification, the term "amino acid" also includes amino acid analogs and mimetics. Analogs are compounds having the same general $H_2N(R)CHCO_2H$ structure of a natural amino acid, except that the R group is not one found among the natural amino acids. Examples of analogs include homoserine, norleucine, methionine-sulfoxide, and methionine methyl sulfonium. An amino acid mimetic is a compound that has a structure different from the general chemical structure of an α-amino acid but functions in a manner similar to one. The amino acid can be of the "L" stereochemistry of the genetically encoded amino acids, as well as of the enantiomeric "D" stereochemistry.

Preferably, C contains an amino acid sequence that is a cleavage recognition sequence for a protease. Many cleavage recognition sequences are known in the art. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. Meth. Enzymol. 244: 412 (1994); and Bouvier et al. Meth. Enzymol. 248: 614 (1995); the disclosures of which are incorporated herein by reference.

A group C can be chosen such that it is cleaved by a protease present in the extracellular matrix in the vicinity of a cancer, e.g., a protease released by nearby dying cancer cells or a tumor-associated protease secreted by cancer cells. Exemplary extracellular tumor-associated proteases are plasmin, matrix metalloproteases (MMP), thimet oligopeptidase (TOP) and CD10. See, e.g., Trouet et al., U.S. Pat. No. 7,402,556 B2 (2008); Dubois et al., U.S. Pat. No. 7,425,541 B2 (2008); and Bebbington et al., U.S. Pat. No. 6,897,034 B2 (2005). Cathepsin D, normally lysosomal enzyme found inside cells, is sometimes found in the environs of a tumor, possibly released by dying cancer cells.

For conjugates designed to be by an enzyme, C preferably comprises an amino acid sequence selected for cleavage by proteases such cathepsins B, C, D, H, L and S, especially cathepsin B. Exemplary cathepsin B cleavable peptides include Val-Ala, Val-Cit, Val-Lys, Lys-Val-Ala, Asp-Val-Ala, Val-Ala, Lys-Val-Cit, Ala-Val-Cit, Val-Gly, Val-Gln, and Asp-Val-Cit. (Herein, amino acid sequences are written in the N-to-C direction, as in $H2N-AA^2-AA^1-CO_2H$, unless the context clearly indicates otherwise.) See Dubowchik et al., *Biorg. Med. Chem. Lett.* 1998, 8, 3341; Dubowchik et al., *Biorg. Med. Chem. Lett.* 1998, 8, 3347; and Dubowchik et al., *Bioconjugate Chem.* 2002, 13, 855; the disclosures of which are incorporated by reference.

Another enzyme that can be utilized for cleaving peptidyl linkers is legumain, a lysosomal cysteine protease that preferentially cleaves at Ala-Ala-Asn.

In one embodiment, Group C is a peptide comprising a two-amino acid sequence -$AA^2$-AA'- wherein AA' is lysine, arginine, or citrulline and $AA^2$ is phenylalanine, valine, alanine, leucine or isoleucine. In another embodiment, C consists of a sequence of one to three amino acids, selected from the group consisting of Val-Cit, Ala-Val, Val-Ala-Val, Lys-Lys, Ala-Asn-Val, Val-Leu-Lys, Cit-Cit, Val-Lys, Ala-Ala-Asn, Lys, Cit, Ser, and Glu. More preferably, it is a two to three amino acid peptide from the foregoing group.

The preparation and design of cleavable groups C consisting of a single amino acid is disclosed in Chen et al., U.S. Pat. No. 8,664,407 B2 (2014), the disclosure of which is incorporated herein by reference.

Group C can be bonded directly to Z or D; i.e. spacers $X^Z$ or $X^D$, as the case may be, can be absent.

When present, spacer $X^Z$ provides spatial separation between C and Z, lest the former sterically interfere with antigen binding by latter or the latter sterically interfere with cleavage of the former. Further, spacer $X^Z$ can be used to confer increased solubility or decreased aggregation properties to conjugates. A spacer $X^Z$ can comprise one or more modular segments, which can be assembled in any number of combinations. Examples of suitable segments for a spacer $X^Z$ are:

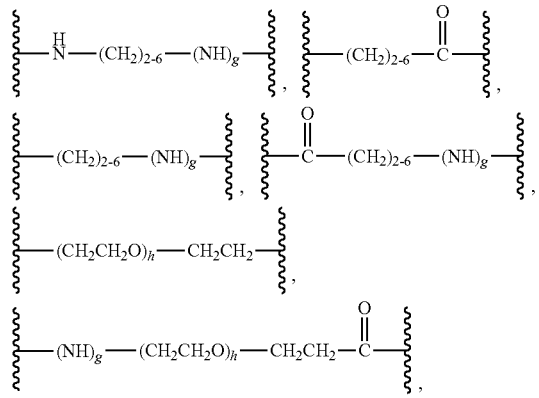

and combinations thereof,
where the subscript g is 0 or 1 and the subscript h is 1 to 24, preferably 2 to 4. These segments can be combined, such as illustrated below:

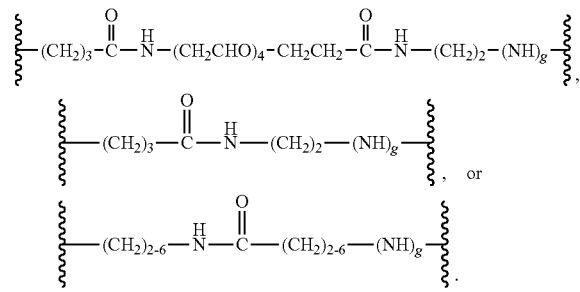

Spacer $X^D$, if present, provides spatial separation between C and D, lest the latter interfere sterically or electronically with cleavage of the former. Spacer $X^D$ also can serve to introduce additional molecular mass and chemical functionality into a conjugate. Generally, the additional mass and functionality will affect the serum half-life and other properties of the conjugate. Thus, through judicious selection of spacer groups, the serum half-live of a conjugate can be modulated. Spacer $X^D$ also can be assembled from modular segments, analogously to the description above for spacer $X^Z$.

Spacers $X^Z$ and/or $X^D$, where present, preferably provide a linear separation of from 4 to 25 atoms, more preferably from 4 to 20 atoms, between Z and C or D and C, respectively.

The linker can perform other functions in addition to covalently linking the antibody and the drug. For instance, the linker can contain a poly(ethylene glycol) ("PEG") group. Since the conjugation step typically involves coupling a drug-linker to an antibody in an aqueous medium, a PEG group many enhance the aqueous solubility of the drug-linker. Also, a PEG group may enhance the solubility or reduce aggregation in the resulting ADC. Where a PEG group is present, it may be incorporated into either spacer $X^Z$ of $X^D$, or both. The number of repeat units in a PEG group can be from 2 to 20, preferably between 4 and 10.

Either spacer $X^Z$ or $X^D$, or both, can comprise a self-immolating moiety. A self-immolating moiety is a moiety that (1) is bonded to C and either Z or D and (2) has a structure such that cleavage from group C initiates a reaction sequence resulting in the self-immolating moiety disbonding itself from Z or D, as the case may be. In other words, reaction at a site distal from Z or D (cleavage from group C) causes the $X^Z$-Z or the $X^D$-D bond to rupture as well. The presence of a self-immolating moiety is desirable in the case of spacer $X^D$ because, if, after cleavage of the conjugate, spacer $X^D$ or a portion thereof were to remain attached to D, the biological activity of D may be impaired. The use of a self-immolating moiety is especially desirable where cleavable group C is a polypeptide, in which instance the self-immolating moiety typically is located adjacent thereto, in order to prevent D from sterically or electronically interfering with peptide cleavage.

Exemplary self-immolating moieties (i)-(v) bonded to a hydroxyl or amino group of D are shown below:

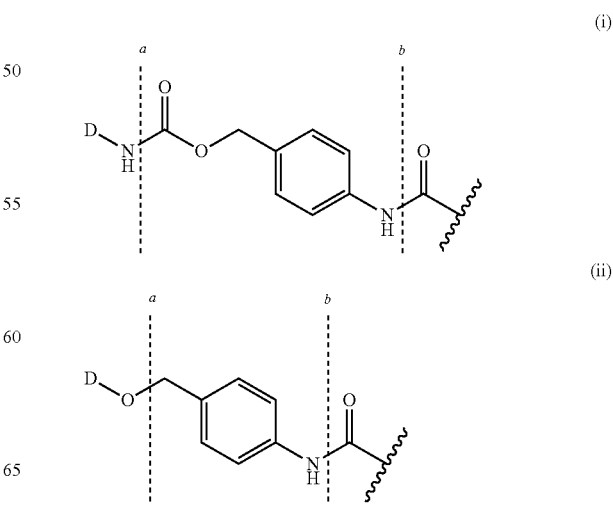

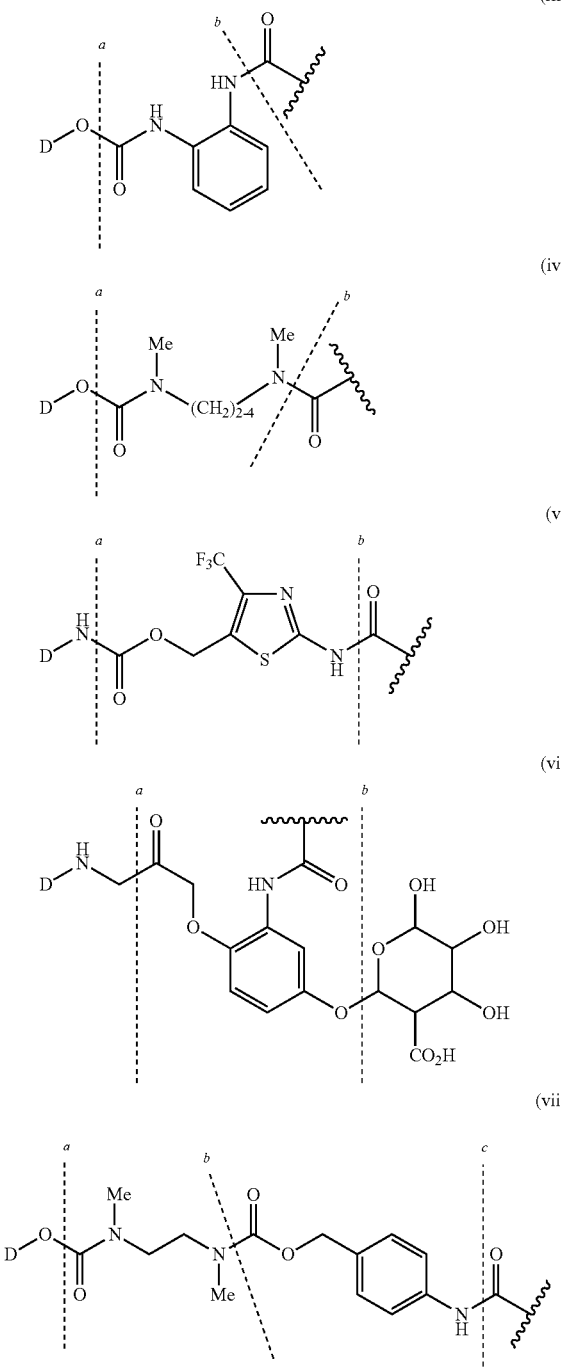

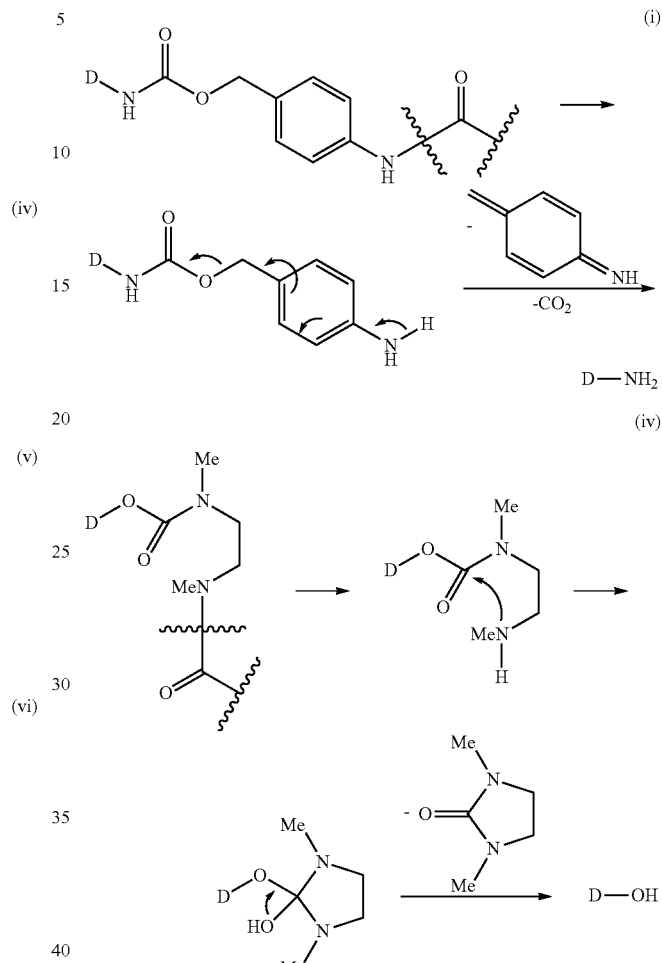

as the case may be. By way of illustration, self-immolating mechanisms for structures (i) and (iv) are shown below:

The self-immolating moiety is the structure between dotted lines a and b (or dotted lines b and c), with adjacent structural features shown to provide context. Self-immolating moieties (i) and (v) are bonded to a D-NH$_2$ (i.e., conjugation is via an amino group), while self-immolating moieties (ii), (iii), and (iv) are bonded to a D-OH (i.e., conjugation is via a hydroxyl or carboxyl group). Cleavage of the bond at dotted line b by an enzyme—a peptidase in the instance of structures (i)-(v) and a β-glucuronidase in the instance of structure (vi)—initiates a self-immolating reaction sequence that results in the cleavage of the bond at dotted line a and the consequent release of D-OH or D-NH$_2$, In other words, cleavage of a first chemical bond at one part of a self-immolating group initiates a sequence of steps that results in the cleavage of a second chemical bond—the one connecting the self-immolating group to the drug—at a different part of the self-immolating group, thereby releasing the drug.

In some instances, self-immolating groups can be used in tandem, as shown by structure (vii). In such case, cleavage at dotted line c triggers self-immolation of the moiety between dotted lines b and c by a 1,6-elimination reaction, followed by self-immolation of the moiety between dotted lines a and b by a cyclization-elimination reaction. For additional disclosures regarding self-immolating moieties, see Carl et al., *J. Med. Chem.* 1981, 24, 479; Carl et al., WO 81/01145 (1981); Dubowchik et al., *Pharmacology &Therapeutics* 1999, 83, 67; Firestone et al., U.S. Pat. No. 6,214, 345 B1 (2001); Toki et al., *J. Org. Chem.* 2002, 67, 1866; Doronina et al., *Nature Biotechnology* 2003, 21, 778 (erratum, p. 941); Boyd et al., U.S. Pat. No. 7,691,962 B2; Boyd et al., US 2008/0279868 A1; Sufi et al., WO 2008/083312 A2; Feng, U.S. Pat. No. 7,375,078 B2; Jeffrey et al., U.S. Pat. No. 8,039,273; and Senter et al., US 2003/0096743 A1; the disclosures of which are incorporated by reference.

In another embodiment, Z and D are linked by a non-cleavable linker, i.e., C is absent. Metabolism of D eventually reduces the linker to a small appended moiety that does not interfere with the biological activity of D.

Conjugation Techniques

Conjugates of TLR7 agonists disclosed herein preferably are made by first preparing a compound comprising D and linker $(X^D)_a(C)_c(X^Z)_b$ (where $X^D$, C, $X^Z$, a, b, and c are as defined for formula (II)) to form drug-linker compound represented by formula (V):

where $R^{31}$ is a functional group suitable for reacting with a complementary functional group on Z to form the conjugate. Examples of suitable groups $R^{31}$ include amino, azide, thiol, cyclooctyne,

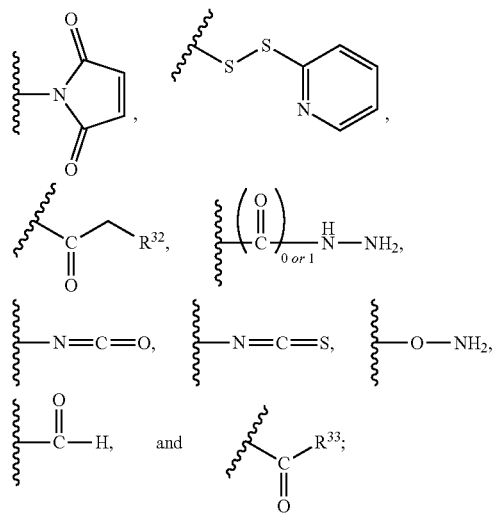

where $R^{32}$ is Cl, Br, F, mesylate, or tosylate and $R^{33}$ is Cl, Br, I, F, OH, —O—N-succinimidyl, —O-(4-nitrophenyl), —O-pentafluorophenyl, or —O-tetrafluorophenyl. Chemistry generally usable for the preparation of suitable moieties $D$-$(X^D)_a C(X^Z)_b$—$R^{31}$ is disclosed in Ng et al., U.S. Pat. No. 7,087,600 B2 (2006); Ng et al., U.S. Pat. No. 6,989,452 B2 (2006); Ng et al., U.S. Pat. No. 7,129,261 B2 (2006); Ng et al., WO 02/096910 A1; Boyd et al., U.S. Pat. No. 7,691,962 B2; Chen et al., U.S. Pat. No. 7,517,903 B2 (2009); Gangwar et al., U.S. Pat. No. 7,714,016 B2 (2010); Boyd et al., US 2008/0279868 A1; Gangwar et al., U.S. Pat. No. 7,847, 105 B2 (2010); Gangwar et al., U.S. Pat. No. 7,968,586 B2 (2011); Sufi et al., U.S. Pat. No. 8,461,117 B2 (2013); and Chen et al., U.S. Pat. No. 8,664,407 B2 (2014); the disclosures of which are incorporated herein by reference.

Preferably reactive functional group —$R^{31}$ is —$NH_2$, —OH, —$CO_2H$, —SH, maleimido, cyclooctyne, azido (—$N_3$), hydroxylamino (—$ONH_2$) or N-hydroxysuccinimido. Especially preferred functional groups —$R^{31}$ are:

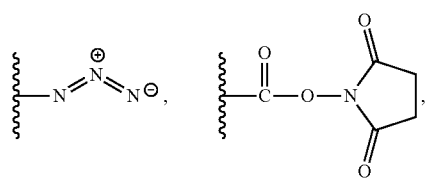

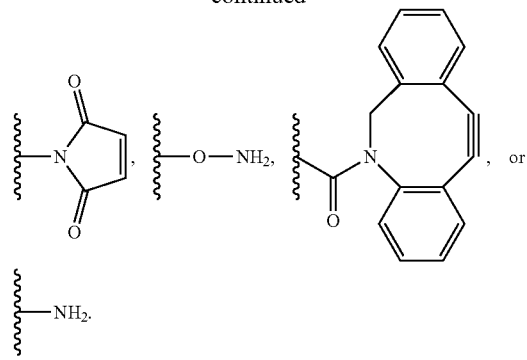

An —OH group can be esterified with a carboxy group on the antibody, for example, on an aspartic or glutamic acid side chain.

A —$CO_2H$ group can be esterified with a —OH group or amidated with an amino group (for example on a lysine side chain) on the antibody.

An N-hydroxysuccinimide group is functionally an activated carboxyl group and can conveniently be amidated by reaction with an amino group (e.g., from lysine).

A maleimide group can be conjugated with an —SH group on the antibody (e.g., from cysteine or from the chemical modification of the antibody to introduce a sulfhydryl functionality), in a Michael addition reaction.

Where an antibody does not have a cysteine —SH available for conjugation, an ε-amino group in the side chain of a lysine residue can be reacted with 2-iminothiolane or N-succinimidyl-3-(2-pyridyldithio)propionate ("SPDP") to introduce a free thiol (—SH) group—creating a cysteine surrogate, as it were. The thiol group can react with a maleimide or other nucleophile acceptor group to effect conjugation. The mechanism if illustrated below with 2-iminothiolane.

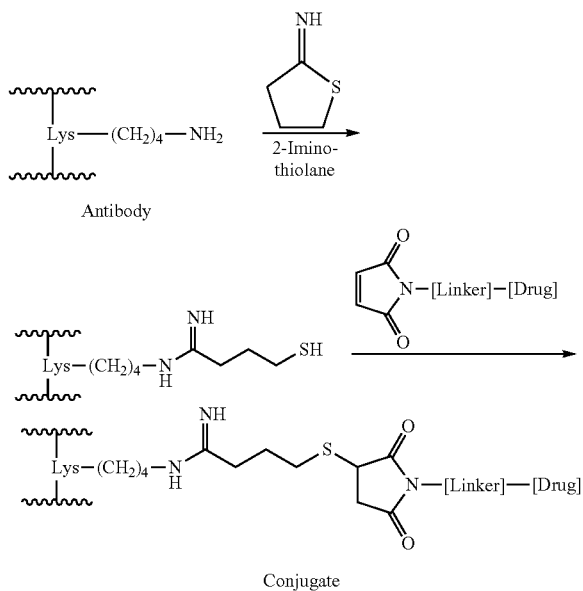

Typically, a thiolation level of two to three thiols per antibody is achieved. For a representative procedure, see Cong et al., U.S. Pat. No. 8,980,824 B2 (2015), the disclosure of which is incorporated herein by reference.

In a reversed arrangement, an antibody Z can be modified with N-succinimidyl 4-(maleimidomethyl)-cyclohexanecarboxylate ("SMCC") or its sulfonated variant sulfo-SMCC, both of which are available from Sigma-Aldrich, to introduce a maleimide group thereto. Then, conjugation can be effected with a drug-linker compound having an —SH group on the linker.

An alternative conjugation method employs copper-free "click chemistry," in which an azide group adds across a strained cyclooctyne to form an 1,2,3-triazole ring. See, e.g., Agard et al., *J. Amer. Chem. Soc.* 2004, 126, 15046; Best, *Biochemistry* 2009, 48, 6571, the disclosures of which are incorporated herein by reference. The azide can be located on the antibody and the cyclooctyne on the drug-linker moiety, or vice-versa. A preferred cyclooctyne group is dibenzocyclooctyne (DIBO). Various reagents having a DIBO group are available from Invitrogen/Molecular Probes, Eugene, Oreg. The reaction below illustrates click chemistry conjugation for the instance in which the DIBO group is attached to the antibody (Ab):

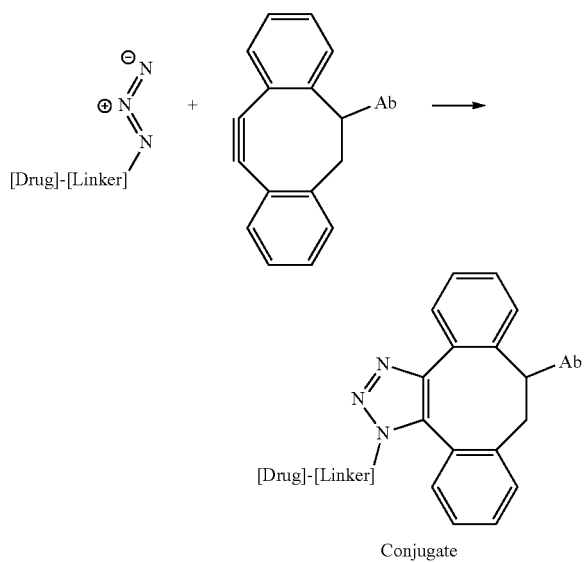

Conjugate

Yet another conjugation technique involves introducing a non-natural amino acid into an antibody, with the non-natural amino acid providing a functionality for conjugation with a reactive functional group in the drug moiety. For instance, the non-natural amino acid p-acetylphenylalanine can be incorporated into an antibody or other polypeptide, as taught in Tian et al., WO 2008/030612 A2 (2008). The ketone group in p-acetylphenylalanine can be a conjugation site via the formation of an oxime with a hydroxylamino group on the linker-drug moiety. Alternatively, the non-natural amino acid p-azidophenylalanine can be incorporated into an antibody to provide an azide functional group for conjugation via click chemistry, as discussed above. Non-natural amino acids can also be incorporated into an antibody or other polypeptide using cell-free methods, as taught in Goerke et al., US 2010/0093024 A1 (2010) and Goerke et al., *Biotechnol. Bioeng.* 2009, 102 (2), 400-416. The foregoing disclosures are incorporated herein by reference. Thus, in one embodiment, an antibody that is used for making a conjugate has one or more amino acids replaced by a non-natural amino acid, which preferably is p-acetylphenylalanine orp-azidophenylalanine, more preferably p-acetylphenylalanine.

Still another conjugation technique uses the enzyme transglutaminase (preferably bacterial transglutaminase from *Streptomyces mobaraensis* or BTG), per Jeger et al., *Angew. Chem. Int. Ed.* 2010, 49, 9995. BTG forms an amide bond between the side chain carboxamide of a glutamine (the amine acceptor) and an alkyleneamino group (the amine donor), which can be, for example, the ε-amino group of a lysine or a 5-amino-n-pentyl group. In a typical conjugation reaction, the glutamine residue is located on the antibody, while the alkyleneamino group is located on the linker-drug moiety, as shown below:

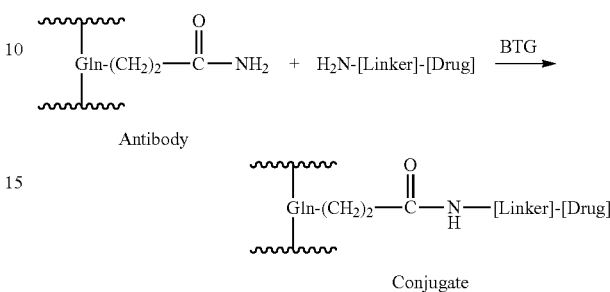

Conjugate

The positioning of a glutamine residue on a polypeptide chain has a large effect on its susceptibility to BTG mediated transamidation. None of the glutamine residues on an antibody are normally BTG substrates. However, if the antibody is deglycosylated—the glycosylation site being asparagine 297 (N297; numbering per EU index as set forth in Kabat et al., "Sequences of proteins of immunological interest," 5th ed., Pub. No. 91-3242, U.S. Dept. Health & Human Services, NIH, Bethesda, Md., 1991; hereinafter "Kabat") of the heavy chain—nearby glutamine 295 (Q295) is rendered BTG susceptible. An antibody can be deglycosylated enzymatically by treatment with PNGase F (Peptide-N-Glycosidase F). Alternatively, an antibody can be synthesized glycoside free by introducing an N297A mutation in the constant region, to eliminate the N297 glycosylation site. Further, it has been shown that an N297Q substitution not only eliminates glycosylation, but also introduces a second glutamine residue (at position 297) that too is an amine acceptor. Thus, in one embodiment, the antibody is deglycosylated. In another embodiment, the antibody has an N297Q substitution. Those skilled in the art will appreciate that deglycosylation by post-synthesis modification or by introducing an N297A mutation generates two BTG-reactive glutamine residues per antibody (one per heavy chain, at position 295), while an antibody with an N297Q substitution will have four BTG-reactive glutamine residues (two per heavy chain, at positions 295 and 297).

An antibody can also be rendered susceptible to BTG-mediated conjugation by introducing into it a glutamine containing peptide, or "tag," as taught, for example, in Pons et al., US 2013/0230543 A1 (2013) and Rao-Naik et al., WO 2016/144608 A1.

In a complementary approach, the substrate specificity of BTG can be altered by varying its amino acid sequence, such that it becomes capable of reacting with glutamine 295 in an umodified antibody, as taught in Rao-Naik et al., WO 2017/059158 A1 (2017).

While the most commonly available bacterial transglutaminase is that from *S. mobaraensis*, transglutaminase from other bacteria, having somewhat different substrate specificities, can be considered, such as transglutaminase from *Streptoverticillium ladakanum* (Hu et al., US 2009/0318349 A1 (2009), US 2010/0099610 A1 (2010), and US 2010/0087371 A1 (2010)).

TLR7 agonists of this disclosure having a primary or secondary alkyl amine are particularly suitable for use in conjugates, as the secondary amine provides a functional group for attachment of the linker. An example of such a TLR7 agonist-linker compound is compound 41, which can be made from compound IIa-01 and contains an enzymatically cleavable linker. FIG. 5 shows a scheme according to which compound 41 can be prepared.

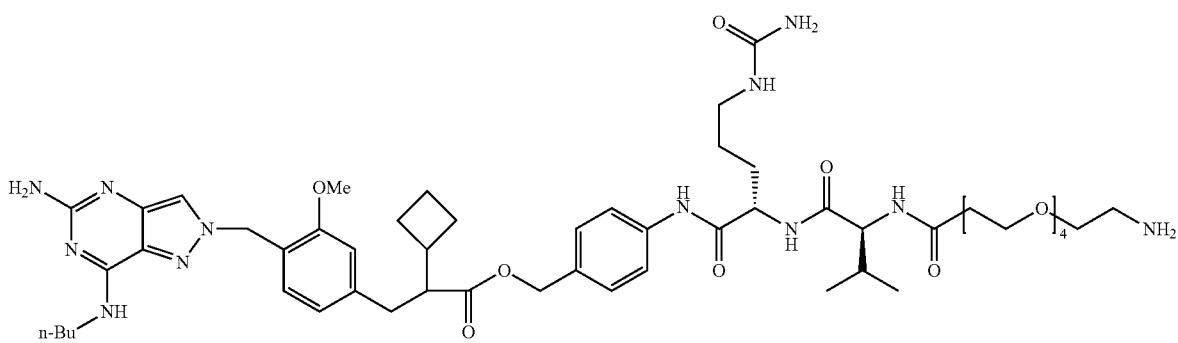

41

An example of a TLR7 agonist-linker compound that contains a non-enzymatically cleavable linker is compound 43, which also can be made from compound IIa-01. FIG. 6 shows a pathway for synthesizing compound 43.

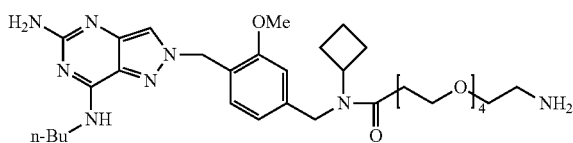

43

Both compounds 41 and 43 contain a primary alkylamino group, rendering them amenable to conjugation with transglutaminase. A suitable conjugation procedure is described in the Examples hereinbelow.

Conjugation can also be effected using the enzyme Sortase A, as taught in Levary et al., *PLoS One* 2011, 6(4), e18342; Proft, *Biotechnol. Lett.* 2010, 32, 1-10; Ploegh et al., WO 2010/087994 A2 (2010); and Mao et al., WO 2005/051976 A2 (2005). The Sortase A recognition motif (typically LPXTG, where X is any natural amino acid) may be located on the ligand Z and the nucleophilic acceptor motif (typically GGG) may be the group $R^{31}$ in formula (III), or vice-versa.

TLR7 Agonist Conjugates

Applying the fore-described techniques, TLR7 agonist conjugates such as the ones shown below can be prepared:

PEGYLATION

Attachment of a poly(ethylene glycol) (PEG) chain to a drug ("PEGylation") can improve the latter's pharmacokinetic properties. The circulation half-life of the drug is increased, sometimes by over an order of magnitude, concomitantly reducing the dosage needed to achieve a desired therapeutic effect. PEGylation can also decrease metabolic degradation of a drug and reduce its immunogenicity. For a review, see Kolate et al., *J. Controlled Release* 2014, 192, 167.

Initially, PEGylation was applied to biologic drugs. As of 2016, over ten PEGylated biologics had been approved. Turecek et al., *J. Pharmaceutical Sci.* 2016, 105, 460. More recently, stimulated by the successful application of the concept to biologics, attention has turned towards its application to small molecule drugs. In addition to the aforementioned benefits, PEGylated small molecule drugs may have increased solubility and cause fewer toxic effects. Li et al. *Prog. Polymer Sci.* 2013, 38, 421.

The compounds disclosed herein can be PEGylated. Where a compound has an aliphatic primary or secondary amine or an aliphatic hydroxyl, such as the case of compound shown below at the positions indicated by arrows, it can be PEGylated via an ester, amide, carbonate, or carbamate group with a carboxy-containing PEG molecule utilizing conventional techniques such as dicyclohexylcarbodiimide, HATU, N-hydroxysuccinimide esters, and the

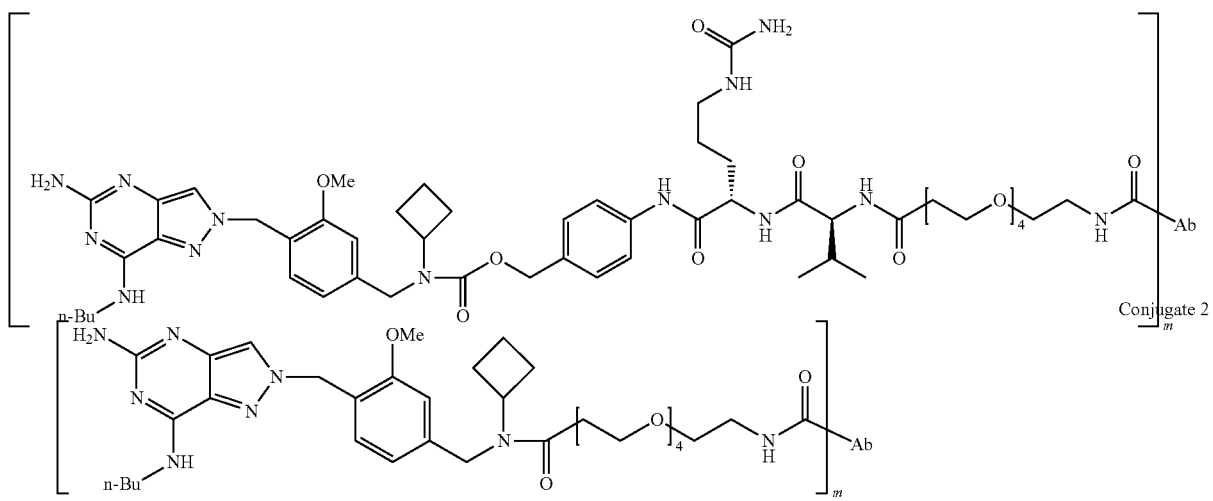

where m is 1, 2, 3, or 4 and Ab is an antibody.

like. Various other methods for PEGylating pharmaceutical molecules are disclosed in Alconcel et al., *Polymer Chem.* 2011, 2, 1442, the disclosure of which is incorporated herein by reference.

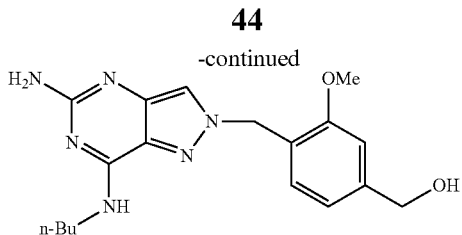

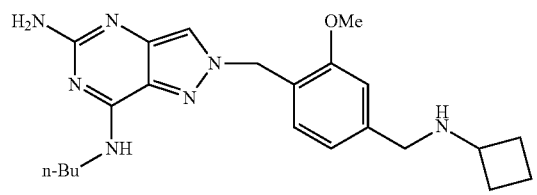

If desired, a TLR7 agonist disclosed herein can be PEGylated via an enzymatically cleavable linker comprising a self-immolating moiety, to allow release of the un-PEGylated agonist in a designed manner. Further, PEGylation can be combined with conjugation to a protein such as an antibody, if the PEG-containing molecule has a suitable functional group such as an amine for attachment to the protein. The protein can provide an additional therapeutic function or, if an antibody, can provide a targeting function. These concepts are illustrated in the following reaction sequence, where TLR7-NH—R generically represents a TLR7 agonist:

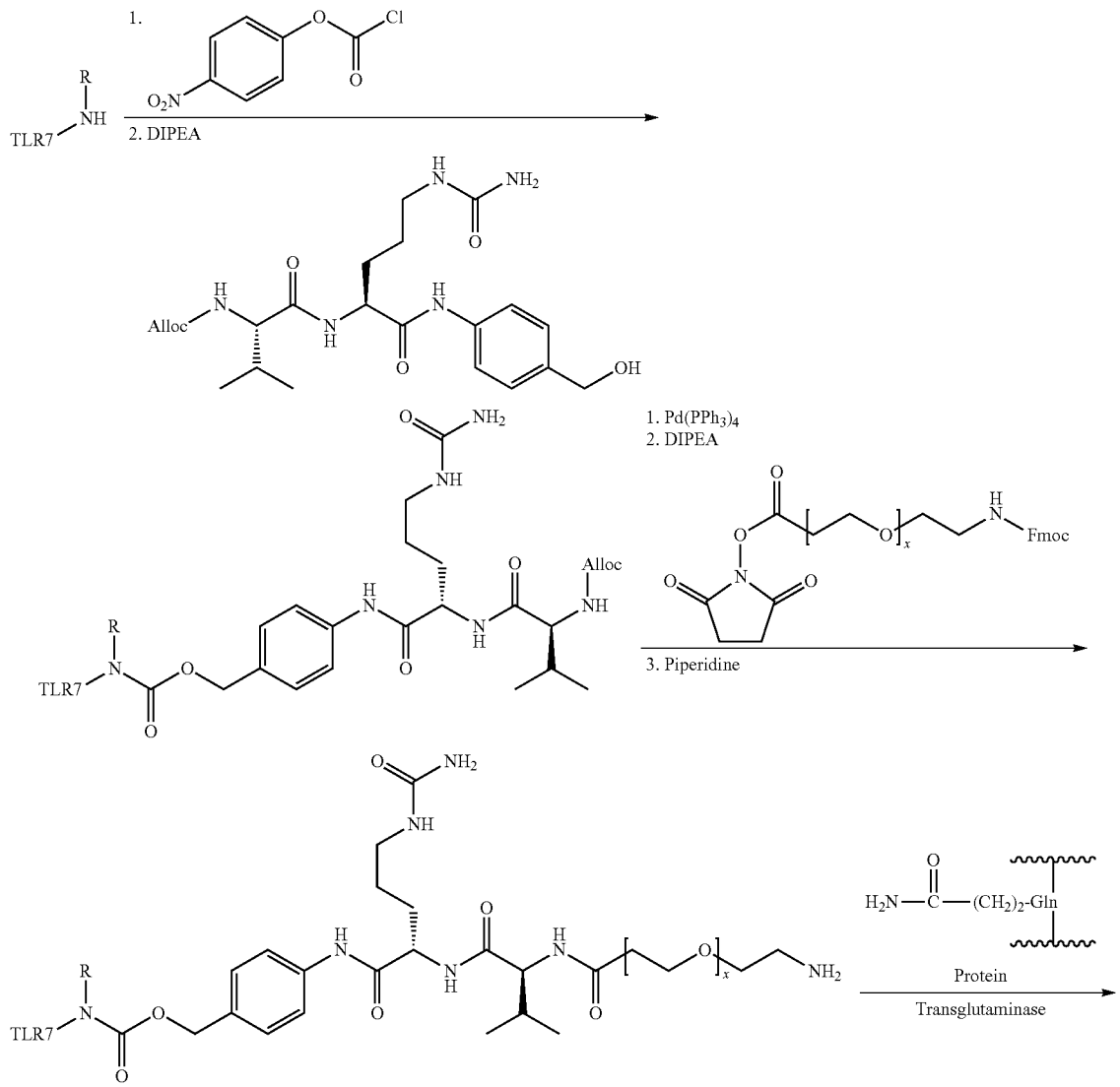

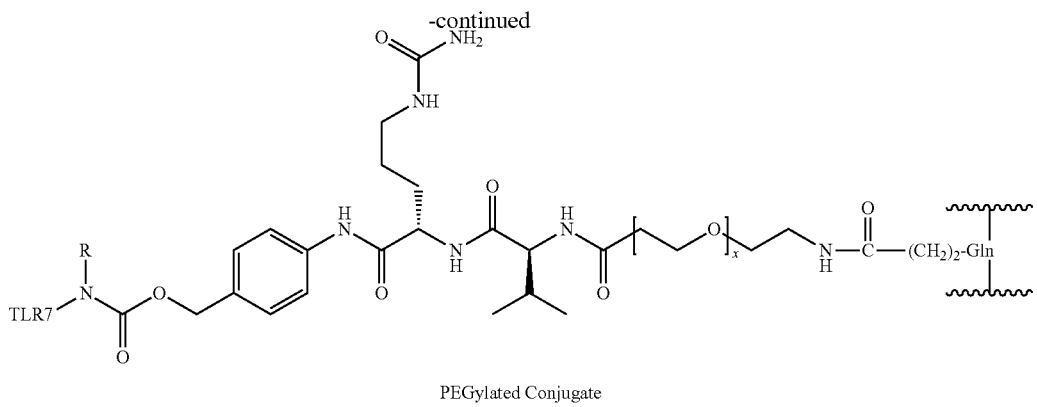

PEGylated Conjugate

In the above reaction sequence, the valine-citrulline (Val-Cit) dipeptide is cleavable by the enzyme cathepsin B, with ap-aminobenzyl oxycarbonyl (PABC) group serving as a self-immolating spacer. The functional group for conjugation is an amine group, which is temporarily protected by an Fmoc group. Conjugation is effected by the enzyme transglutaminase, with a glutamine (Gln) side chain acting as the acyl acceptor. The subscript x, denoting the number of PEG repeat units, can vary widely, depending on the purpose of the PEGylation, as discussed below. For some purposes, x can be relatively small, such as 2, 4, 8, 12, or 24. For other purposes, x is large, for example between about 45 and about 910.

Those skilled in the art will understand that the sequence is illustrative and that other elements—peptide, self-immolating group, conjugation method, PEG length, etc. —may be employed, as is well known in the art. They will also understand that, while the above sequence combines PEGylation and conjugation, PEGylation does not require conjugation, and vice-versa.

Where the compound lacks aliphatic hydroxyl or aliphatic primary or secondary amine, it still can be PEGylated at the aromatic amine on the pyrimidine ring. A method for PEGylating at this position is disclosed by Zarraga, US 2017/0166384 A1 (2007), the disclosure of which is incorporated by reference.

In some embodiments, it may be desirable to have multiple PEGylated agonists linked in a single molecule. For instance, four PEGylated arms can be constructed on pentaerythritol ($C(CH_2OH)_4$) and a TLR7 agonist can be attached to each PEGylated arm. See Gao et al., US 2013/0028857 A1 (2013), the disclosure of which is incorporated by reference.

For modulating pharmacokinetics, it is generally preferred that the PEG moiety have a formula weight of between about 2 kDa (corresponding to about 45 —($CH_2CH_2O$)— repeating units) and between about 40 kDa (corresponding to about 910 —($CH_2CH_2O$)— repeating units), more preferably between about 5 kDa and about 20 kDa. That is, the range of the subscript x in the above formulae is from about 45 to about 910. It is to be understood that PEG compositions are not 100% homogeneous but, rather, exhibit a distribution of molecular weights. Thus, a reference to, for example, "20 kDa PEG" means PEG having an average molecular weight of 20 kDa.

PEGylation can also be used for improving the solubility of an agonist. In such instances a shorter PEG chain can be used, for example comprising 2, 4, 8, 12, or 24 repeating units.

Pharmaceutical Compositions and Administration

In another aspect, there is provided a pharmaceutical composition comprising a compound of as disclosed herein, or of a conjugate thereof, formulated together with a pharmaceutically acceptable carrier or excipient. It may optionally contain one or more additional pharmaceutically active ingredients, such as a biologic or a small molecule drug. The pharmaceutical compositions can be administered in a combination therapy with another therapeutic agent, especially an anti-cancer agent.

The pharmaceutical composition may comprise one or more excipients. Excipients that may be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., *Remington: The Science and Practice of Pharmacy*, 20th Ed. (Lippincott Williams & Wilkins 2003).

Preferably, a pharmaceutical composition is suitable for intravenous, intramuscular, subcutaneous, parenteral, spinal or epidermal administration (e.g., by injection or infusion). Depending on the route of administration, the active compound may be coated in a material to protect it from the action of acids and other natural conditions that may inactivate it. The phrase "parenteral administration" means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, the pharmaceutical composition can be administered via a non-parenteral route, such as a topical, epidermal or mucosal route of administration, for example, intranasally, orally, vaginally, rectally, sublingually or topically.

Pharmaceutical compositions can be in the form of sterile aqueous solutions or dispersions. They can also be formulated in a microemulsion, liposome, or other ordered structure suitable to achieve high drug concentration. The compositions can also be provided in the form of lyophilates, for reconstitution in water prior to administration.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide a therapeutic response. For example, a single bolus may be administered, several divided doses may be administered over time, or the dose may be proportionally reduced or increased as indicated by the exigencies of the situation. It is especially advantageous to formulate parenteral compositions in dosage unit form for ease of administration and uniformity of dosage. "Dosage unit form" refers to physically discrete units suited as unitary dosages for the subjects to be treated; each unit containing a predetermined quantity of active compound calculated to produce the desired therapeutic response, in associ-ation with the required pharmaceutical carrier.

The dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg, or alternatively 0.1 to 5 mg/kg. Exemplary treatment regimens are administration once per week, once every two weeks, once every three weeks, once every four weeks, once a month, once every 3 months, or once every three to 6 months. Preferred dosage regimens include 1 mg/kg body weight or 3 mg/kg body weight via intravenous administration, using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 µg/mL and in some methods about 25-300 µg/mL.

A "therapeutically effective amount" of a compound of the invention preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective amount" preferably inhibits tumor growth by at least about 20%, more preferably by at least about 40%, even more preferably by at least about 60%, and still more preferably by at least about 80% relative to untreated subjects. A therapeutically effective amount of a therapeutic compound can decrease tumor size, or otherwise ameliorate symptoms in a subject, which is typically a human but can be another mammal. Where two or more therapeutic agents are administered in a combination treatment, "therapeutically effective amount" refers to the efficacy of the combination as a whole, and not each agent individually.

The pharmaceutical composition can be a controlled or sustained release formulation, including implants, transdermal patches, and microencapsulated delivery systems. Biodegrada-ble, biocompatible polymers can be used, such as ethylene vinyl acetate, polyanhydrides, poly-glycolic acid, collagen, polyorthoesters, and polylactic acid. See, e.g., *Sustained and Controlled Release Drug Delivery Systems*, J. R. Robinson, ed., Marcel Dekker, Inc., New York, 1978.

Therapeutic compositions can be administered via medical devices such as (1) needleless hypodermic injection devices; (2) micro-infusion pumps; (3) transdermal devices; (4) infusion devices; and (5) osmotic devices.

In certain embodiments, the pharmaceutical composition can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs.

INDUSTRIAL APPLICABILITY

TLR7 agonist compounds disclosed herein can be used for the treatment of a disease or condition that can be ameliorated by activation of TLR7.

In one embodiment, the TLR7 agonist is used in combination with an anti-cancer immunotherapy agent—also known as an immuno-oncology agent. An anti-cancer immunotherapy agent works by stimulating a body's immune system to attack and destroy cancer cells, especially through the activation of T cells. The immune system has numerous checkpoint (regulatory) molecules, to help maintain a balance between its attacking legitimate target cells and preventing it from attacking healthy, normal cells. Some are stimulators (up-regulators), meaning that their engagement promotes T cell activation and enhances the immune response. Others are inhibitors (down-regulators or brakes), meaning that their engagement inhibits T cell activation and abates the immune response. Binding of an agonistic immunotherapy agent to a stimulatory checkpoint molecule can lead to the latter's activation and an enhanced immune response against cancer cells. Reciprocally, binding of an antagonistic immunotherapy agent to an inhibitory checkpoint molecule can prevent down-regulation of the immune system by the latter and help maintain a vigorous response against cancer cells. Examples of stimulatory checkpoint molecules are B7-1, B7-2, CD28, 4-1BB (CD137), 4-1BBL, ICOS, CD40, ICOS-L, OX40, OX40L, GITR, GITRL, CD70, CD27, CD40, DR3 and CD28H. Examples of inhibitory checkpoint molecules are CTLA-4, PD-1, PD-L1, PD-L2, LAG-3, TIM-3, Galectin 9, CEACAM-1, BTLA, CD69, Galectin-1, CD113, GPR56, VISTA, 2B4, CD48, GARP, PD1H, LAIR1, TIM-1, CD96 and TIM-4.

Whichever the mode of action of an anti-cancer immunotherapy agent, its effectiveness can be increased by a general up-regulation of the immune system, such as by the activation of TLR7. Thus, in one embodiment, this specification provides a method of treating a cancer, comprising administering to a patient suffering from such cancer a therapeutically effective combination of an anti-cancer immunotherapy agent and a TLR7 agonist as disclosed herein. The timing of administration can be simultaneous, sequential, or alternating. The mode of administration can systemic or local. The TLR7 agonist can be delivered in a targeted manner, via a conjugate.

Cancers that could be treated by a combination treatment as described above include acute myeloid leukemia, adrenocortical carcinoma, Kaposi sarcoma, lymphoma, anal cancer, appendix cancer, teratoid/rhabdoid tumor, basal cell carcinoma, bile duct cancer, bladder cancer, bone cancer, brain cancer, breast cancer, bronchial tumor, carcinoid tumor, cardiac tumor, cervical cancer, chordoma, chronic lymphocytic leukemia, chronic myeloproliferative neoplasm, colon cancer, colorectal cancer, craniopharyngioma, bile duct cancer, endometrial cancer, ependymoma, esophageal cancer, esthesioneuroblastoma, Ewing sarcoma, eye cancer, fallopian tube cancer, gallbladder cancer, gastrointestinal carcinoid tumor, gastrointestinal stromal tumor, germ cell tumor, hairy cell leukemia, head and neck cancer, heart cancer, liver cancer, hypopharngeal cancer, pancreatic cancer, kidney cancer, laryngeal cancer, chronic myelogenous leukemia, lip and oral cavity cancer, lung cancer, melanoma, Merkel cell carcinoma, mesothelioma, mouth cancer, oral cancer, osteosarcoma, ovarian cancer, penile cancer, pharyngeal cancer, prostate cancer, rectal cancer, salivary gland cancer, skin cancer, small intestine cancer, soft tissue sarcoma, testicular cancer, throat cancer, thyroid cancer, urethral cancer, uterine cancer, vaginal cancer, and vulvar cancer.

Anti-cancer immunotherapy agents that can be used in combination therapies as disclosed herein include: AMG 557, AMP-224, atezolizumab, avelumab, BMS 936559, cemiplimab, CP-870893, dacetuzumab, durvalumab, enoblituzumab, galiximab, IMP321, ipilimumab, lucatumumab, MEDI-570, MEDI-6383, MEDI-6469, muromonab-CD3, nivolumab, pembrolizumab, pidilizumab, spartalizumab, tremelimumab, urelumab, utomilumab, varlilumab, vonlerolizumab. Table C below lists their alternative name(s) (brand name, former name, research code, or synonym) and the respective target checkpoint molecule.

TABLE C

| Immunotherapy Agent | Alternative Name(s) | Target |
|---|---|---|
| AMG 557 | | B7RP-1 (ICOSL) |
| AMP-224 | | PD-1 |
| Atezolizumab | MPDL3280A, RO5541267, TECENTRIQ® | PD-L1 |
| Avelumab | BAVENCIO® | PD-L1 |
| BMS 936559 | | PD-L1 |
| Cemiplimab | LIBTAYO® | PD-1 |
| CP-870893 | | CD40 |
| Dacetuzumab | | CD40 |
| Durvalumab | IMFINZI® | PD-L1 |
| Enoblituzumab | MGA271 | B7-H3 |
| Galiximab | | B7-1 (CD80) |
| IMP321 | | LAG-3 |
| Ipilimumab | YERVOY® | CTLA-4 |
| Lucatumumab | | CD40 |
| MEDI-570 | | ICOS (CD278) |
| MEDI-6383 | | OX40 |
| MEDI-6469 | | OX40 |
| Muromonab-CD3 | | CD3 |
| Nivolumab | OPDIVO® | PD-1 |
| Pembrolizumab | KEYTRUDA® | PD-1 |
| Pidilizumab | MDV9300 | PD-1 |
| Spartalizumab | PDR001 | PD-1 |
| Tremelimumab | Ticilimumab, CP-675, CP-75,206 | CTLA-4 |
| Urelumab | BMS-663513 | CD137 |
| Utomilumab | PF-05082566 | CD137 |
| Varlilumab | CDX 1127 | CD27 |
| Vonlerolizumab | RG7888, MOXR0916, pogalizumab | OX40 |

In one embodiment of a combination treatment with a TLR7 agonist, the anti-cancer immunotherapy agent is an antagonistic anti-CTLA-4, anti-PD-1, or anti-PD-L1 antibody. The cancer can be lung cancer (including non-small cell lung cancer), pancreatic cancer, kidney cancer, head and neck cancer, lymphoma (including Hodgkin's lymphoma), skin cancer (including melanoma and Merkel skin cancer), urothelial cancer (including bladder cancer), gastric cancer, hepatocellular cancer, or colorectal cancer.

In another embodiment of a combination treatment with a TLR7 agonist, the anti-cancer immunotherapy agent is an antagonistic anti-CTLA-4 antibody, preferably ipilimumab.

In another embodiment of a combination treatment with a TLR7 agonist, the anti-cancer immunotherapy agent is an antagonistic anti-PD-1 antibody, preferably nivolumab or pembrolizumab.

The TLR7 agonists disclosed herein also are useful as vaccine adjuvants.

Biological Activity

The biological activity of compounds disclosed herein as TLR7 agonists can be assayed by the procedures following.

Human TLR7 Agonist Activity Assay

This procedure describes a method for assaying human TLR7 (hTLR7) agonist activity of the compounds disclosed in this specification.

Engineered human embryonic kidney blue cells (HEK-Blue™ TLR cells; Invivogen) possessing a human TLR7-secreted embryonic alkaline phosphatase (SEAP) reporter transgene were suspended in a non-selective, culture medium (DMEM high-glucose (Invitrogen), supplemented with 10% fetal bovine serum (Sigma)). HEK-Blue™ TLR7 cells were added to each well of a 384-well tissue-culture plate (15,000 cells per well) and incubated 16-18 h at 37° C., 5% $CO_2$. Compounds (100 nl) were dispensed into wells containing the HEK-Blue™ TLR cells and the treated cells were incubated at 37° C., 5% $CO_2$. After 18 h treatment ten microliters of freshly-prepared Quanti-Blue™ reagent (Invivogen) was added to each well, incubated for 30 min (37° C., 5% $CO_2$) and SEAP levels measured using an Envision plate reader (OD=620 nm). The half maximal effective concentration values ($EC_{50}$; compound concentration which induced a response halfway between the assay baseline and maximum) were calculated. The reported activities may be the average of plural measurements.

Induction of Type I Interferon Genes (NIX-1) and CD69 in Human Blood

The induction of Type I interferon (IFN) MX-1 genes and the B-cell activation marker CD69 are downstream events that occur upon activation of the TLR7 pathway. The following is a human whole blood assay that measures their induction in response to a TLR7 agonist.

Heparinized human whole blood was harvested from human subjects and treated with test TLR7 agonist compounds at 1 mM. The blood was diluted with RPMI 1640 media and Echo was used to predot 10 nL per well giving a final concentration of 1 uM (10 nL in 10 uL of blood). After mixing on a shaker for 30 sec, the plates were covered and placed in a 37° C. chamber for o/n=17 hrs. Fixing/lysis buffer was prepared (5×->1× in $H_2O$, warm at 37° C.; Cat # BD 558049) and kept the perm buffer (on ice) for later use.

For surface markers staining (CD69): prepared surface Abs: 0.045 ul hCD14-FITC (ThermoFisher Cat # MHCD1401)+0.6 ul hCD19-ef450 (ThermoFisher Cat #48-0198-42)+1.5 ul hCD69-PE (cat # BD555531)+0.855 ul FACS buffer. Added 3 ul/well, spin1000 rpm for 1 min and mixed on shaker for 30 sec, put on ice for 30 mins. Stop stimulation after 30 minutes with 70 uL of prewarmed 1× fix/lysis buffer and use Feliex mate to resuspend (15 times, change tips for each plate) and incubate at 37C for 10 minutes.

Centrifuge at 2000 rpm for 5 minutes aspirate with HCS plate washer, mix on shaker for 30 sec and then wash with 70 uL in dPBS and pelleted 2×s (2000 rpm for 5 min) and 50 ul wash in FACS buffer pelleted 1×s (2000 rpm for 5 min). Mix on shaker for 30 sec. For Intracellular markers staining (MX-1): Add 50 ul of BD Perm buffer III and mix on shaker for 30 sec. Incubate on ice for 30 minutes (in the dark). Wash with 50 uL of FACS buffer 2× (spin A2300 rpm×5 min after perm) followed by mixing on shaker for 30 sec. Resuspended in 20 ul of FACS buffer containing MX1 antibody ( )(4812)-Alexa 647: Novus Biologicals # NBP2-43704AF647) 20 ul FACS bf+0.8 ul hIgG+0.04 ul MX-1. Spin 1000 rpm for 1 min, mix on shaker for 30 se and the samples were incubated at RT in the dark for 45 minutes followed by washing 2×FACS buffer (spin @2300 rpm×5 min after perm). Resuspend 20 ul (35 uL total per well) of FACS buffer and cover with foil and place in 4° C. to read the following day. Plates were read on iQuePlus. The results were loaded into toolset and IC50 curves are generated in curve master. The y-axis 100% is set to 1 uM of resiquimod.

Induction of TNF-Alpha and Type I IFN Response Genes in Mouse Blood

The induction of TNF-alpha and Type I IFN response genes are downstream events that occur upon activation of the TLR7 pathway. The following is an assay that measures their induction in whole mouse blood in response to a TLR7 agonist.

Heparinized mouse whole blood was diluted with RPMI 1640 media with Pen-Strep in the ratio of 5:4 (50 uL whole blood and 40 uL of media). A volume of 90 uL of the diluted blood was transferred to wells of Falcon flat bottom 96-well tissue culture plates, and the plates were incubated at 4° C. for 1 h. Test compounds in 100% DMSO stocks were diluted 20-fold in the same media for concentration response assays, and then 10 uL of the diluted test compounds were added to the wells, so that the final DMSO concentration was 0.5%. Control wells received 10 uL media containing 5% DMSO. The plates were then incubated at 37° C. in a 5% $CO_2$ incubator for 17 h. Following the incubation, 100 uL of the culture medium as added to each well. The plates were centrifuged and 130 uL of supernatant was removed for use in assays of TNFa production by ELISA (Invitrogen, Catalog Number 88-7324 by Thermo-Fisher Scientific). A 70 uL volume of mRNA catcher lysis buffer (1×) with DTT from the Invitrogen mRNA Catcher Plus kit (Cat # K1570-02) was added to the remaining 70 uL sample in the well, and was mixed by pipetting up and down 5 times. The plate was then shaken at room temperature for 5-10 min, followed by addition of 2 uL of proteinase K (20 mg/mL) to each well. Plates were then shaken for 15-20 min at RT. The plates were then stored at −80° C. until further processing.

The frozen samples were thawed and mRNA was extracted using the Invitrogen mRNA Catcher Plus kit (Cat # K1570-02) according to the manufacturer's instructions. Half yield of mRNA from RNA extraction were used to synthesize cDNA in 20 μL reverse transcriptase reactions using Invitrogen SuperScript IV VILO Master Mix (Cat #11756500). TaqMan® real-time PCR was performed using QuantStudio Real-Time PCR system from ThermoFisher (Applied Biosystems). All real-time PCR reactions were run in duplicate using commercial predesigned TaqMan assays for mouse IFIT1, IFIT3, MX1 and PPIA gene expression and TaqMan Master Mix. PPIA was utilized as the housekeeping gene. The recommendations from the manufacturer were followed. All raw data (Ct) were normalized by average housekeeping gene (Ct) and then the comparative Ct (∆∆Ct) method were utilized to quantify relative gene expression (RQ) for experimental analysis.

Synthesis

The practice of this invention can be further understood by reference to the following examples, which are provided by way of illustration and not of limitation.

A table after the Examples lists acronyms and abbreviations used herein and their meanings.

Example 1—Synthesis of Compounds per FIG. 1

This example and FIG. 1 relate to the synthesis of compound IIa-01.

Compound 3.

Methyl 4-amino-1H-pyrazole-5-carboxylate 2 (4 g, 28.3 mmol) and methyl (Z)-4-(2,3-bis(methoxycarbonyl)guanidino)-1H-pyrazole-5-carboxylate 1 in methanol (50 mL) was treated with acetic acid (8.11 mL, 142 mmol) at which time a precipitate formed. The reaction mixture was stirred overnight. Sodium methoxide (64.8 mL, 283 mmol) was added and stirring was continued overnight. LCMS showed completion of the reaction. The pH was adjusted to 5 by the slow addition of acetic acid, whereby a precipitate formed that was washed with water and then acetonitrile and dried to provide 5.2 g of compound 3 as an off white solid. LCMS ESI: calculated for $C_7H_7N_5O_3$=210.16 (M+H+), found 210.0 (M+H+).

Compound 4.

Compound 3 (2 g, 9.56 mmol), butan-1-amine (1.8 mL, 9 mmol), and DBU (1.6 mL, 10 mmol) in DMSO (10 mL) was slowly treated with BOP (5 g, 11 mmol). The reaction mixture was heated at 60° C. for 2 h at which time LCMS showed completion of the reaction. The reaction was directly purified on reverse phase COMBIFLASH™ apparatus using 80 g C-18 column eluting with 0-100% acetonitrile/water (0.1% formic acid) to yield compound 4 as a white solid. LCMS ESI: calculated for $C_{11}H_{16}N_6O_2$=265.28 (M+H$^+$), found 265.2 (M+H$^+$). $^1$H NMR (400 MHz, dmso-d6) δ 8.02 (s, 1H), 3.97 (s, 3H), 1.74-1.66 (m, 2H), 1.49-1.38 (m, 2H), 1.25 (s, 1H), 0.95 (t, J=7.4 Hz, 3H).

Compound 6.

A mixture of methyl 4-(bromomethyl)-2-methoxybenzoate 5 (1 g, 3.86 mmol) and cyclobutanamine 5a (0.659 mL, 7.72 mmol) in DMF (2 mL) was heated at 70° C. over 30 min at which point LCMS showed the formation of an amine product. The excess base was evaporated and Hunig's Base (1.348 mL, 7.72 mmol) was added, followed by addition of Boc-anhydride (0.896 mL, 3.86 mmol). LCMS showed the completion of reaction. The solvent was evaporated and the crude product was purified by COMBIFLASH™ apparatus using EtOAc/hexanes to provide 0.82 g desired product 6 as a colorless oil. LCMS ESI: calculated for $C_{19}H_{27}NO_5$=350.42 (M+H+), found 350.1 (M+H$^+$).

Compound 7.

A solution of compound 6 (0.82 g, 2.347 mmol) in THF (5 mL) at 0° C. was treated slowly with LiAlH$_4$ (2 M in THF, 1.173 mL, 2.347 mmol) and stirred for 30 min, at which point LCMS showed completion of the reaction. The reaction was quenched by the slow addition of methanol and stirred with Rochelle salt solution for 2 h. The organic layers were separated and the crude product 7 was purified on a COMBIFLASH™ apparatus using EtOAc/hexanes, silica gel column. LCMS ESI: calculated for $C_{18}H_{27}NO_4$=322.41 (M+H$^+$), found 322.1 (M+H$^+$).

Compounds 8 and 9.

A mixture of compound 4 (100 mg, 0.378 mmol), compound 7 (182 mg, 0.568 mmol) and triphenylphosphine (248 mg, 0.946 mmol) in THF (3 mL) was slowly treated with DIAD (0.110 mL, 0.568 mmol) over 5 min and stirred at RT for 30 min under $N_2$ at which point LCMS showed the completion of the reaction. The solvent was evaporated and the crude product was purified on reverse phase COMBIFLASH™ apparatus using 80 g C-18 column eluting with 0-100% acetonitrile/water (1 mM TEAA) to provide a mixture of compounds 8 and 9 as a white solid. LCMS ESI: calculated for $C_{29}H_{41}N_7O_5$=566.69 (M−H$^+$), found 566.3 (M−H$^+$).

The isomers were separated by chiral supercritical fluid chromatography using Column: Kromasil 5-CelluCoat, 21×250 mm, 5 micron, Mobile Phase: 15% MeOH-DEA/ 85%% $CO_2$, Flow Conditions: 45 mL/min, 150 Bar, 40° C., Detector Wavelength: 230 nm, Injection Details: 0.5 mL of ~25 mg/mL in MeOH to provide 17 mg of compound 8 and 25 mg of compound 9.

Analytical Data for Compound 8:
$^1$H NMR (400 MHz, DMSO-$d_6$) δ 9.61 (s, 2H), 7.86 (s, 2H), 6.94 (s, 2H), 6.83 (s, 2H), 6.63 (d, J=7.9 Hz, 2H), 6.51 (d, J=7.5 Hz, 2H), 5.69 (s, 4H), 4.39 (s, 4H), 3.79 (s, 6H), 3.63 (s, 6H), 3.48 (d, J=6.2 Hz, 4H), 3.33 (s, 20H), 3.18 (d, J=5.3 Hz, 1H), 2.05-1.95 (m, 8H), 1.53 (t, J=7.5 Hz, 7H), 1.35 (s, 11H), 1.23 (q, J=7.2 Hz, 6H), 0.86 (t, J=7.4 Hz, 6H).

Analytical Data for Compound 9:
$^1$H NMR (400 MHz, DMSO-$d_6$) δ 9.37 (s, 1H), 8.08 (s, 1H), 6.90 (s, 1H), 6.84 (s, 1H), 6.71 (d, J=7.7 Hz, 1H), 5.48 (s, 2H), 4.42 (s, 3H), 3.78 (d, J=18.0 Hz, 4H), 3.69 (s, 1H), 3.61 (s, 3H), 3.51-3.42 (m, 3H), 2.06-1.97 (m, 6H), 1.61-1.47 (m, 6H), 1.36 (s, 8H), 1.34-1.26 (m, 6H), 0.99 (t, J=7.1 Hz, 3H), 0.94-0.85 (m, 4H).

Compound 8a.

A solution of compound 8 (13 mg, 0.023 mmol) was dissolved in THF (0.5 mL) and was treated with TFA (0.018 mL, 0.229 mmol). LCMS in 30 min showed Boc deprotection. The TFA was evaporated and this mixture was treated with sodium hydroxide (9.16 mg, 0.229 mmol) and heated at 60° C. for 2 h, at which point LCMS showed completion of the reaction. The base was neutralized by the slow addition of 6M HCl and worked up with EtOAc/water. The crude material was purified via preparative HPLC under the following conditions: Column: XBridge C18, 200 mm×19 mm, 5-μm particles; Mobile Phase A: 5:95 acetonitrile:water with 10 mM ammonium acetate; Mobile Phase B: 95:5 acetonitrile:water with 10-mM ammonium acetate; Gradient: a 0-minute hold at 7% B, 7-47% B over 20 minutes, then a 4-minute hold at 100% B; Flow Rate: 20 mL/min. LCMS ESI: calculated for $C_{22}H_{31}N_7O$=410.5 (M+H$^+$), found 410.2 (M+H$^+$). $^1$H NMR (500 MHz, DMSO-$d_6$) δ 7.54 (s, 3H), 7.02 (s, 3H), 6.76 (d, J=7.6 Hz, 3H), 6.47-6.38 (m, 5H), 5.60 (d, J=11.5 Hz, 10H), 3.58 (s, 2H), 3.47 (s, 1H), 3.42 (s, 2H), 3.38 (s, 2H), 3.18-3.11 (m, 2H), 2.02 (s, 4H), 1.90 (s, 5H), 1.70 (t, J=9.5 Hz, 5H), 1.60 (d, J=9.8 Hz, 3H), 1.49 (dt, J=24.2, 8.3 Hz, 9H), 1.36 (d, J=19.4 Hz, 4H), 1.20 (dt, J=15.0, 7.2 Hz, 6H), 0.84 (t, J=7.4 Hz, 9H).

Compound IIa-01.

Compound IIa-01 was prepared in a manner analogous to that used for compound 8a. LCMS ESI: calculated for $C_{22}H_{31}N_7O$=410.5 (M−H$^+$), found 410.2 (M−H$^+$). $^1$H NMR (500 MHz, DMSO-d6) δ 7.64 (s, 1H), 7.02 (s, 1H), 6.90 (d, J=7.7 Hz, 1H), 6.85 (d, J=7.6 Hz, 1H), 5.75 (s, 1H), 5.37 (s, 2H), 3.56 (s, 1H), 3.18-3.11 (m, 1H), 2.55 (s, 3H), 2.04 (d, J=9.0 Hz, 2H), 1.88 (s, 6H), 1.71 (t, J=9.7 Hz, 2H), 1.56 (dq, J=19.1, 10.6, 10.2 Hz, 4H), 1.31 (q, J=7.7 Hz, 2H), 0.88 (t, J=7.4 Hz, 3H).

Figure 2A:
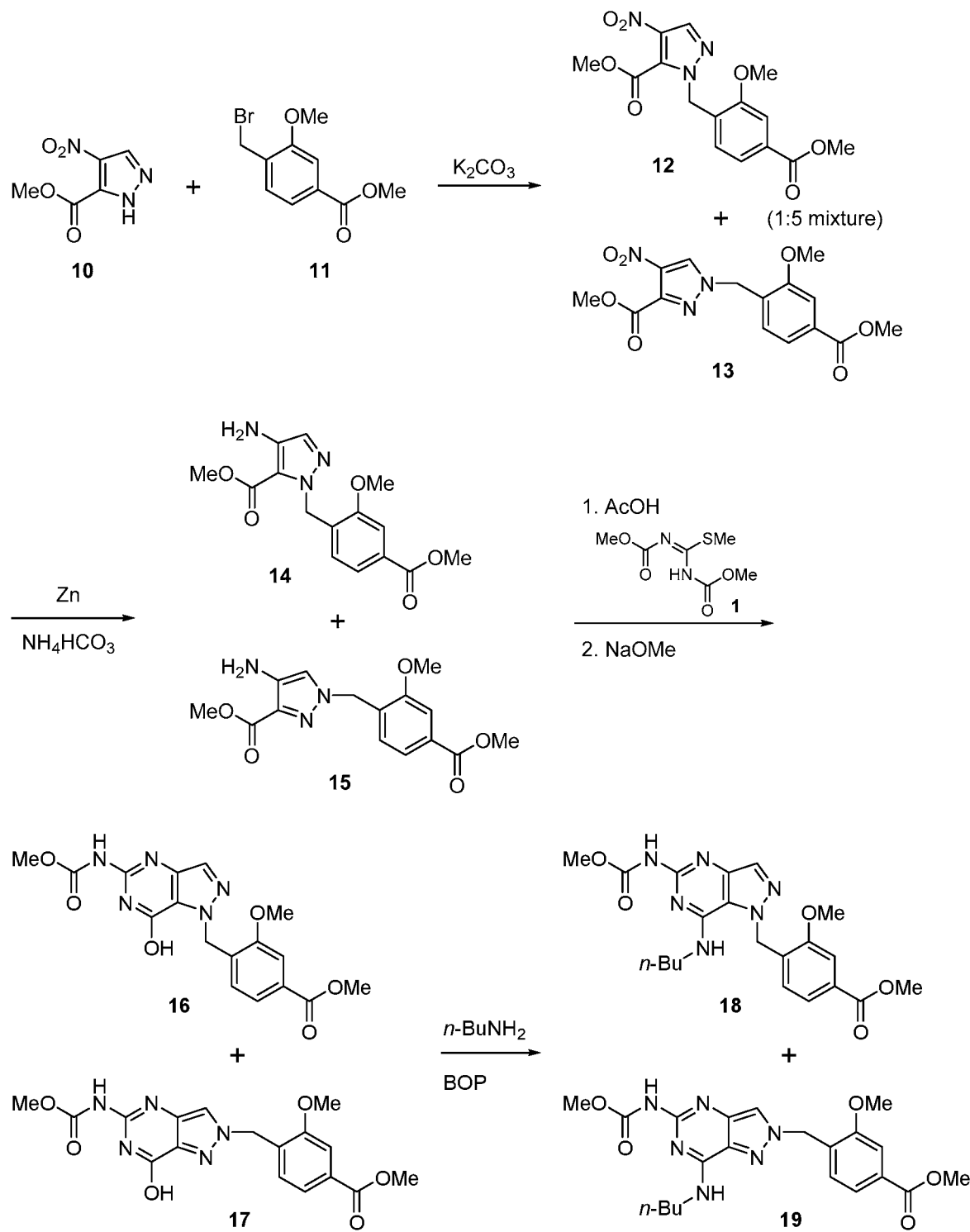
Figure 2B:
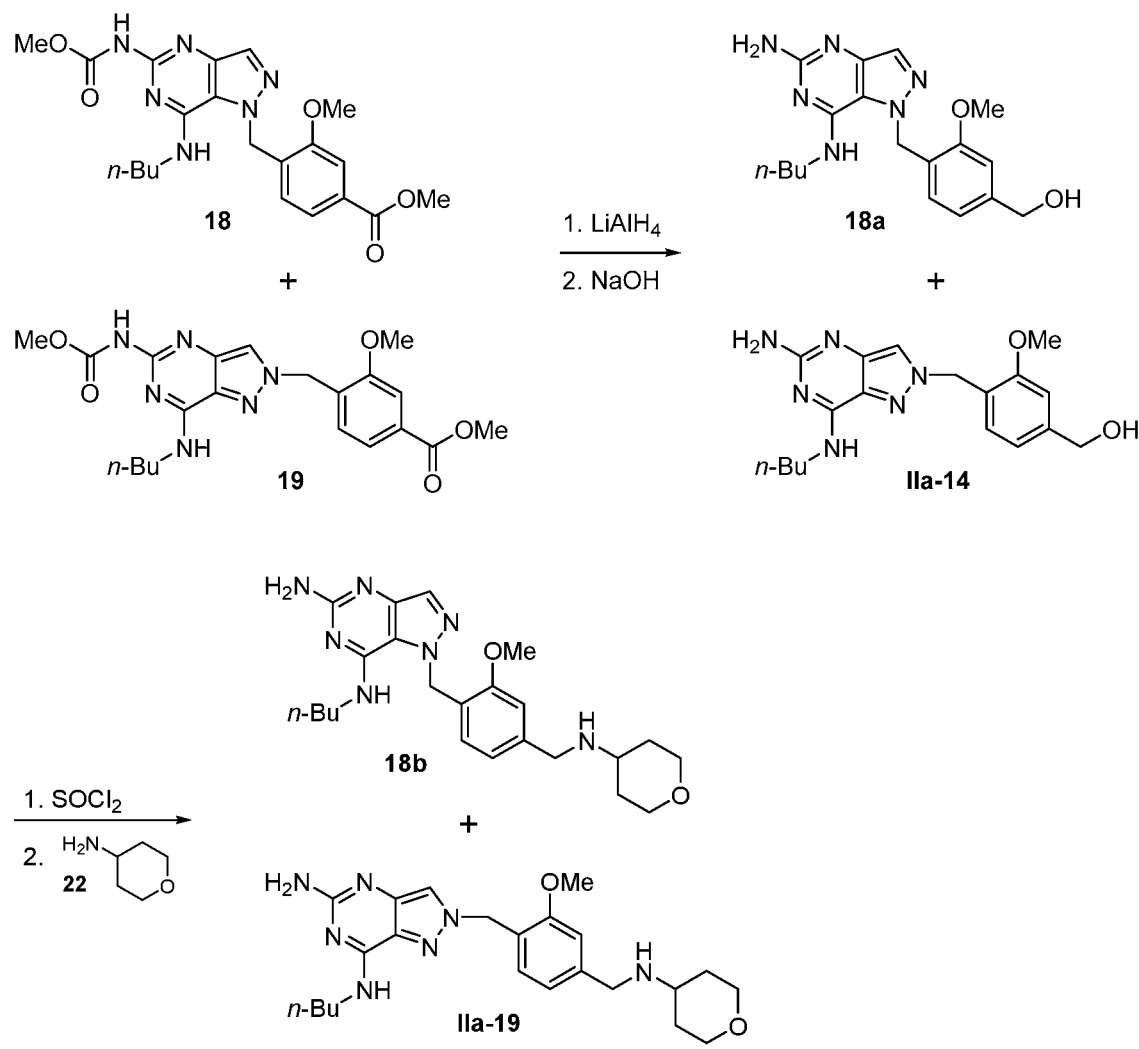

Example 2—Synthesis of Compounds per FIGS. 2A-2B

This example and FIGS. 2A-2B relate to the synthesis of compounds IIa-14 and IIa-19 and other compound analogously made.

Compounds 12 and 13.

A solution of methyl 4-nitro-1H-pyrazole-5-carboxylate 10 (3.27 g, 19.11 mmol) in DMF (20 mL) was treated with $K_2CO_3$ (2.90 g, 21.02 mmol) and methyl 4-(bromomethyl)-3-methoxybenzoate 11 (5 g, 19.30 mmol). The reaction was started at 0° C. and allowed to proceed for 1 h, at which point LCMS showed completion of the reaction with ~1:5 mixture of products. The base was filtered and the reaction was diluted with EtOAc and washed with water 2 times. The solvent was evaporated and the crude product was taken to next step as-is. LCMS ESI: calculated for $C_{15}H_{15}N_3O_7$=350.2 (M−H$^+$), found 350.0 (M−H$^+$).

For characterization purpose, a small amount of the mixture of products was separated using silica gel column chromatography using 0-50% EtOAc/hexanes.

Analytical Data for Compound 12:
$^1$H NMR (400 MHz, DMSO-$d_6$) δ 8.40 (s, 1H), 7.57 (dd, J=7.8, 1.5 Hz, 1H), 7.50 (d, J=1.6 Hz, 1H), 7.27 (d, J=7.9 Hz, 1H), 5.53 (s, 2H), 3.96 (s, 3H), 3.84 (d, J=16.2 Hz, 6H).

Analytical Data for Compound 13:
$^1$H NMR (400 MHz, DMSO-d6) δ 9.05 (s, 1H), 7.62-7.51 (m, 2H), 7.28 (d, J=7.9 Hz, 1H), 5.47 (s, 2H), 3.87 (s, 8H), 3.31 (s, 1H).

Compounds 14 and 15.

A solution of compounds 12 and 13 (2 g, 5.73 mmol), zinc and ammonium formate was stirred at RT for 2 h, after which LCMS showed completion of the reaction. Filtration and concentration yielded a crude mixture of compounds 14 and 15. LCMS ESI: calculated for $C_{15}H_{17}N_3O_5$=320.3 (M+H$^+$), found 320.2 (M+H$^+$).

Compounds 16 and 17.

A mixture of compounds 14 and 15 (1.830 g, 5.73 mmol) and compound 1 in MeOH (20 mL) was treated with acetic acid (1.640 mL, 28.7 mmol) and stirred overnight. The solution was treated with sodium methoxide (13.11 mL, 57.3 mmol) and stirred overnight. LCMS showed conversion to the product. The pH was adjusted to 5 and the resulting precipitate was washed with water. The residue was dried to afford a mixture of compounds 16 and 17. LCMS ESI: calculated for $C_{17}H_{17}N_5O_6$=388.3 (M+H$^+$), found 388.1 (M+H$^+$).

Compounds 18 and 19.

A mixture of compounds 16 and 17 (1 g, 2.58 mmol) in DMSO (10 mL) was treated with butan-1-amine (0.510 mL, 5.16 mmol), DBU (0.428 mL, 2.84 mmol) followed slowly by BOP (1.370 g, 3.10 mmol). The reaction was heated at 70° C. for 2 h, at which point LCMS showed completion of the reaction. The reaction was diluted with water and extracted with EtOAc. The combined organic phases were dried over $Na_2SO_4$ and taken as-is to the next step. LCMS ESI: calculated for $C_{21}H_{26}N_6O_5$=443.4 (M+H$^+$), found 443.2 (M+H$^+$). $^1$H NMR (400 MHz, DMSO-$d_6$) δ 9.41 (s, 1H), 8.20 (s, 1H), 8.08 (s, 1H), 7.57-7.42 (m, 3H), 6.93 (d, J=8.1 Hz, 1H), 5.80 (s, 1H), 5.60 (s, 2H), 4.04 (q, J=7.1 Hz, 1H), 3.95-3.82 (m, 10H), 3.62 (d, J=6.1 Hz, 4H), 3.45 (q, J=7.0 Hz, 3H), 2.68 (d, J=9.9 Hz, 1H), 2.57-2.50 (m, 6H), 2.00 (s, 1H), 1.59 (p, J=7.3 Hz, 3H), 1.54-1.48 (m, 1H), 1.39-1.26 (m, 3H), 1.18 (t, J=7.1 Hz, 2H), 0.86 (dt, J=29.5, 7.3 Hz, 5H).

Compounds 18a and IIa-14.

A solution of compounds 18 and 19 (1.142 g, 2.58 mmol) in THF (2.58 mL, 5.16 mmol) at 0° C. was treated with LiAlH$_4$ (THF, 2.58 mL, 5.16 mmol) and stirred for 1 h, after which LCMS showed completion of the reaction. The reaction was quenched with MeOH and stirred with Rochelle salt solution overnight. The product was extracted with EtOAc and taken to next step as a mixture of crude compounds reduced intermediate. LCMS ESI: calculated for $C_{20}H_{26}N_6O_4$=415.4 (M+H$^+$), found 415.2 (M+H$^+$).

A mixture of the reduced intermediates (1069 mg, 2.58 mmol) in 1,4-dioxane (10 mL) was treated with aqueous sodium hydroxide (2.58 mL, 25.8 mmol) and heated at 80° C. for 5 h, after which LCMS showed formation of product. The base was neutralized with 6M HCl and the solvent was evaporated. The residue was taken up in 5 mL DMF and syringe filtered. The solvent was evaporated to afford a 3:1 mixture of compounds 18a and IIa-14. LCMS ESI: calculated for $C_{18}H_{24}N_6O_2$=357.4 (M+H$^+$), found 357.2 (M+H$^+$).

Compounds 18b and IIa-19.

A solution of compounds Ia-38 and IIa-14 (420 mg, 1.178 mmol) in THF (1 mL) was treated with thionyl chloride (0.172 mL, 2.357 mmol) and stirred for 30 min, after which LCMS showed completion of the reaction. The solvent was evaporated and the crude product was taken to next step as-is. LCMS ESI: calculated for $C_{18}H_{23}ClN_6O$=375.8 (M+H$^+$), found 375.2 (M+H$^+$).

A mixture of the preceding crude product mixture (20 mg, 0.053 mmol) and tetrahydro-2H-pyran-4-amine 22 (5.40 mg, 0.053 mmol) in DMF (1 mL) was heated at 70° C. for 1 h, after which LCMS showed completion of the reaction. The reaction was syringe filtered and the crude products were purified and separated via preparative LC/MS with the following conditions: Column: XBridge C18, 200 mm×19 mm, 5-µm particles; Mobile Phase A: 5:95 acetonitrile:water with 0.1% trifluoroacetic acid; Mobile Phase B: 95:5 acetonitrile:water with 0.1% trifluoroacetic acid; Gradient: a 2-minute hold at 6% B, 6-27% B over 25 minutes, then a 2-minute hold at 100% B; Flow Rate: 20 mL/min; Column Temperature: 25 C. Fraction collection was triggered by MS signals. Fractions containing the desired product were combined and dried via centrifugal evaporation.

Analytical Data for IIa-19:

LCMS ESI: calculated for $C_{23}H_{33}N_7O_2$=440.5 (M+H$^+$), found 440.1 (M+H$^+$). $^1$H NMR (500 MHz, DMSO-d$_6$) δ 9.39 (s, 1H), 7.98 (s, 1H), 7.94 (s, 0H), 7.86 (s, 1H), 7.24 (s, 1H), 7.14-7.03 (m, 2H), 5.51 (s, 2H), 4.16 (s, 2H), 3.96-3.90 (m, 2H), 3.84 (s, 3H), 3.29 (d, J=11.6 Hz, 2H), 2.89 (s, 1H), 2.73 (s, 1H), 2.55 (s, 1H), 2.00 (d, J=12.6 Hz, 2H), 1.58 (p, J=7.5 Hz, 4H), 1.31 (q, J=7.5 Hz, 2H), 0.89 (t, J=7.4 Hz, 3H).

Additional compounds were prepared analogously to compound IIa-19, but using the amine indicated in Table D instead of tetrahydro-2H-pyran-4-amine 22 in the last step.

TABLE D

Compounds Made Analogously to Compound IIa-19

| Cpd. No. | Expected mass (M + H) | Observed mass (M + H) | Structure |
|---|---|---|---|
| IIa-02 | 425.5 | 425.2 | Piperazine |
| IIa-03 | 400.4 | 400.3 | 2-Aminoethan-1-ol |
| IIa-04 | 413.5 | 413.1 | Propane-1,3-diamine |
| IIa-05 | 447.5 | 447.2 | Pyridin-4-ylmethanamine |
| IIa-06 | 427.5 | 437.1 | 2-Azaspiro[3.3]heptan-6-amine |
| IIa-07 | 426.5 | 426.1 | Oxetan-3-ylmethanamine |
| IIa-08 | 454.5 | 454.1 | 4-Aminocyclohexan-1-ol |
| IIa-09 | 426.5 | 426.0 | 3-Aminocyclobutan-1-ol |
| IIa-10 | 461.1 | 461.3 | 4-(Aminomethyl)aniline |
| IIa-11 | 462.5 | 462.1 | 2-(Methylsulfonyl)ethan-1-amine |
| IIa-12 | 495.6 | 495.1 | Octahydropyrrolo[3,4-c]pyrrole |
| IIa-15 | 412.5 | 412.2 | Oxetan-3-amine |
| IIa-17 | 469.6 | 469.2 | 2-(Piperazin-1-yl)ethan-1-ol |
| IIa-18 | 451.5 | 450.9 | 2,6-Diazaspiro[3.3]heptane |
| IIa-20 | 428.5 | 428.2 | 1-Amino-2-methylpropan-2-ol |
| IIa-21 | 407.4 | 407.0 | 1H-Imidazole |
| IIa-22 | 414.5 | 414.2 | 2-Methoxyethan-1-amine |
| IIa-23 | 440.5 | 440.3 | 2-(Azetidin-3-yl)ethan-1-ol |
| IIa-24 | 440.5 | 439.9 | 3-(Aminomethyl)cyclobutan-1-ol |
| IIa-25 | 476.5 | 476.3 | 2-(4-aminophenyl)ethan-1-ol |
| IIa-26 | 428.5 | 427.9 | 3-(Methylamino)propan-1-ol |
| IIa-27 | 437.5 | 437.9 | 2,5-Diazabicyclo[2.2.1]heptane |
| IIa-28 | 454.5 | 453.9 | (1-Aminocyclopentyl)methanol |
| IIa-29 | 439.5 | 438.9 | 1,4-Diazepane |
| IIa-30 | 426.5 | 426.3 | Morpholine |
| IIa-31 | 424.5 | 424.2 | Piperidine |
| IIa-32 | 410.5 | 410.1 | Pyrrolidine |
| IIa-33 | 412.5 | 412.1 | Butan-1-amine |
| IIa-34 | 412.5 | 412.2 | 2-Methylpropan-2-amine |
| IIa-36 | 439.5 | 439.2 | 1-Methylpiperazine |

Figure 3:
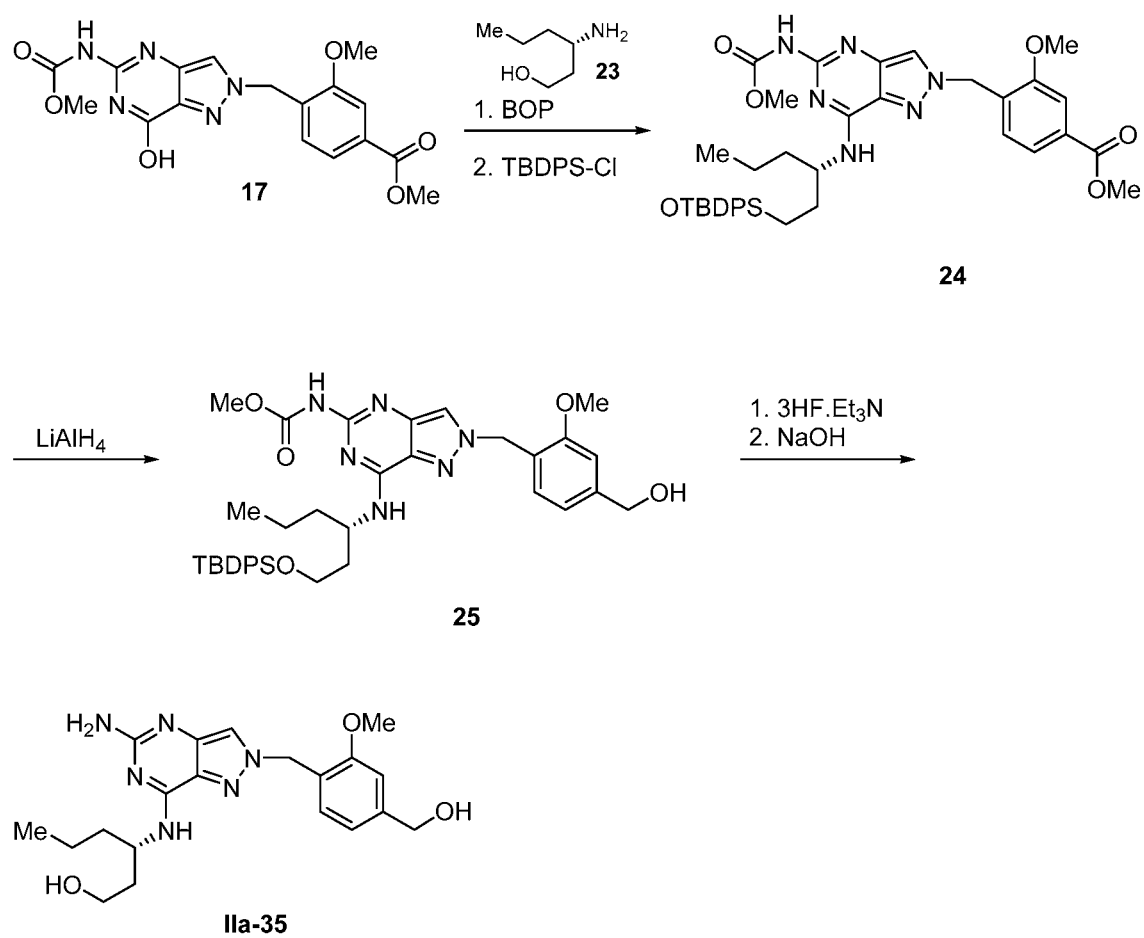

Example 3—Synthesis of Compounds per FIG. 3

Compound IIa-35 was made following the synthetic scheme pf FIG. 3. Expected mass (M+H) 401.4; observed 401.1.

Figure 4A:
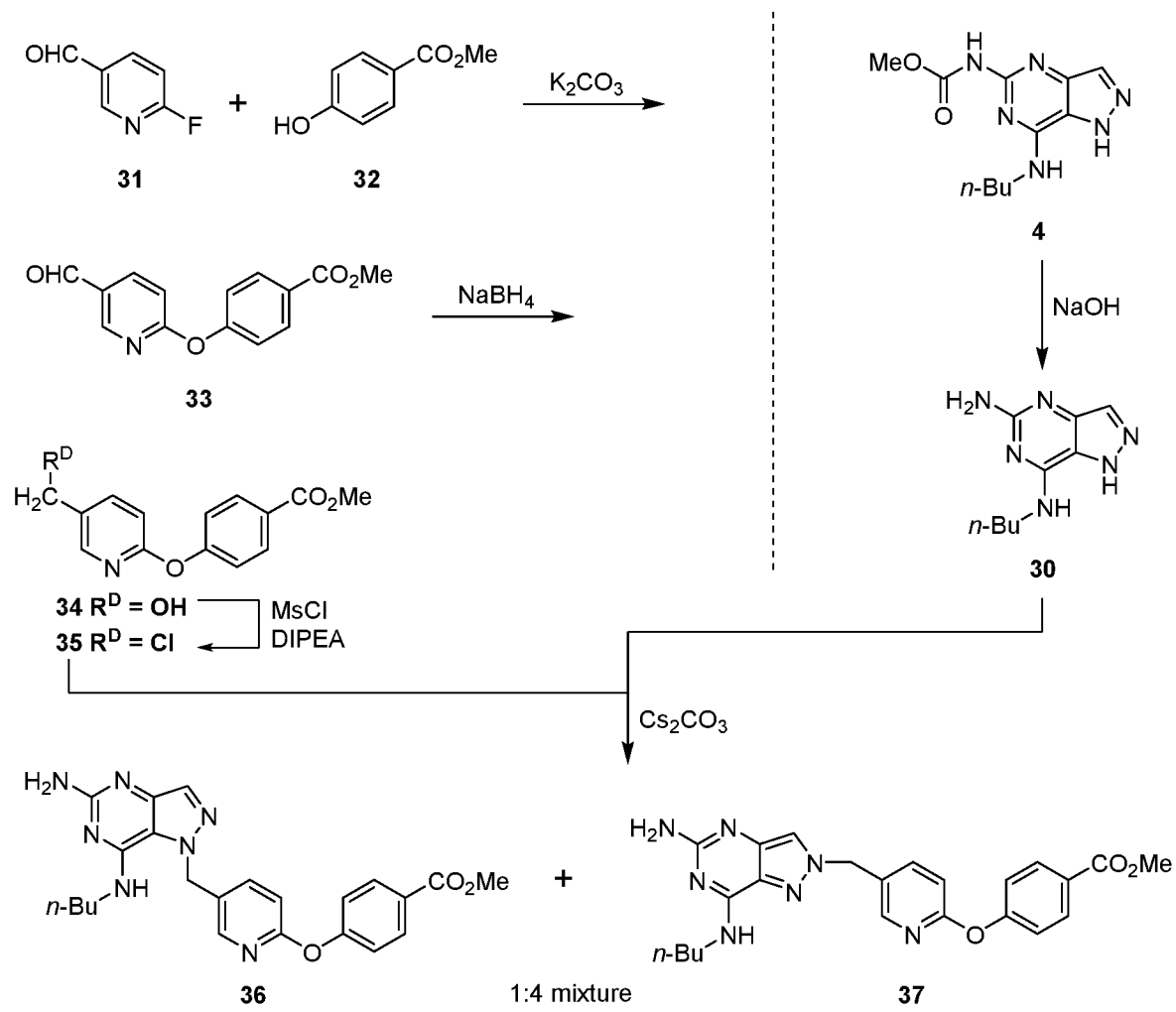
Figure 4B:
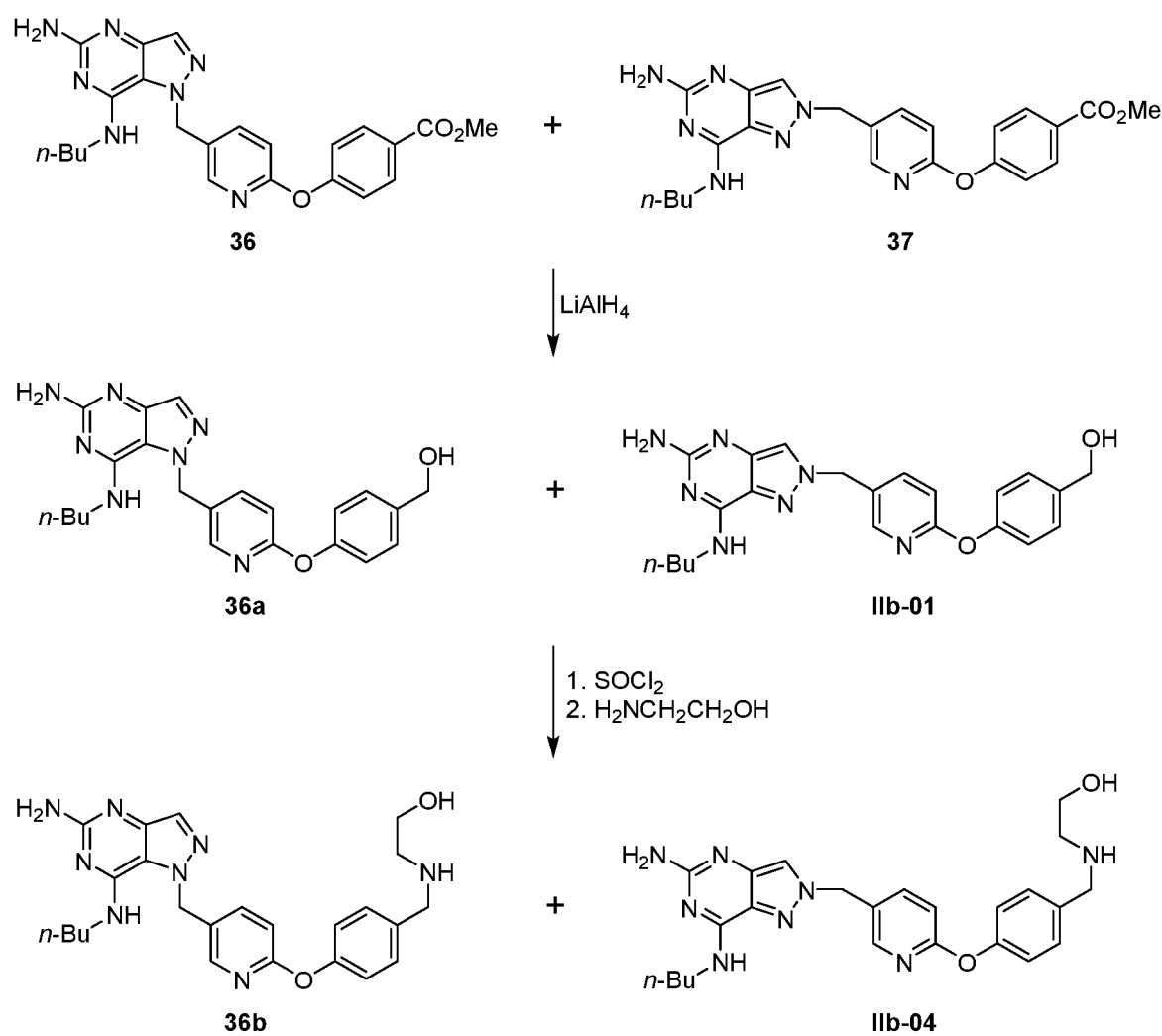

Example 4—Synthesis of Compounds per FIGS. 4A-4B

This example and FIGS. 4A-4B relate to the synthesis of compounds IIb-01, and IIb-04, and other compounds analogously made.

Compound 30.

A suspension of compound 4 (400 mg, 1.513 mmol) in dioxane (5 mL) was treated with sodium hydroxide (10 N in water, 1.513 mL, 15.13 mmol) and stirred at 60° C. for 45 min. The reaction mixture was concentrated. The crude product was dissolved into water and purified by reverse phase chromatography on a COMBIFLASH™ unit using a 150 g C-18 column eluting with 10 mM TEAA in acetonitrile:10 mM in water, 0-70% gradient. The desired fractions were frozen and lyophilized to yield compound 30 (150 mg, 0.727 mmol, 48.1% yield). LCMS ESI: calculated for $C_9H_{15}N_6$=207.1 (M+H$^+$), found 207.2 (M+H$^+$). $^1$H NMR (400 MHz, DMSO-d6) δ 7.56 (br s, 1H), 5.53 (br s, 2H), 3.43 (br d, J=6.2 Hz, 2H), 1.57 (t, J=7.2 Hz, 2H), 1.44-1.29 (m, 2H), 0.95-0.76 (m, 3H).

Compound 33.

A suspension of 6-fluoronicotinaldehyde 31 (1.809 g, 14.46 mmol), methyl 4-hydroxybenzoate 32 (2 g, 13.15 mmol), and K$_2$CO$_3$ (1.998 g, 14.46 mmol) in DMF (26.3 ml) was stirred at 110° C. for 4 h. LCMS indicated the reaction was complete. Upon cooling, the reaction was quenched with water. The resulting solid was collected by filtration and rinsed with water and dried in vacuo to yield compound 33 (3.30 g, 12.84 mmol, 95.1% yield). LCMS ESI: calculated for $C_{14}H_{11}NO_4$=258.1 (M+H$^+$), found 258.0 (M+H$^+$). $^1$H NMR (400 MHz, CHLOROFORM-d) δ 10.01 (s, 1H), 8.63 (d, J=2.4 Hz, 1H), 8.23 (dd, J=8.6, 2.4 Hz, 1H), 8.17-7.97 (m, 2H), 7.27-7.22 (m, 2H), 7.10 (d, J=8.6 Hz, 1H), 3.93 (s, 3H).

Compound 34.

A solution of compound 33 (3.76 g, 14.62 mmol) in MeOH (100 ml) was treated with NaBH$_4$ (0.553 g, 14.62 mmol) portionwise at 0° C. and then stirred for 10 min with continued cooling. LCMS indicated the reaction was complete. Reaction was quenched by slowly adding half saturated NH$_4$Cl. Stirring was continued for 30 min at RT. The reaction mixture was extracted with ethyl acetate. The organic extracts were dried over Na$_2$SO$_4$, filtered, and concentrated. The crude solid was slurried into water and collected by filtration and dried in vacuo to yield compound 34 (3.37 g, 13.00 mmol, 89% yield). LCMS ESI: calculated for $C_{14}H_{13}NO_4$=260.1 (M+H$^+$), found 260.0 (M+H$^+$). $^1$H NMR (400 MHz, CHLOROFORM-d) δ 8.21 (d, J=2.2 Hz, 1H), 8.12-8.04 (m, 2H), 7.81 (dd, J=8.4, 2.4 Hz, 1H), 7.21-7.13 (m, 2H), 6.99 (d, J=8.4 Hz, 1H), 4.71 (s, 2H), 3.91 (s, 3H).

Compound 35.

Compound 34 (7.9 g, 30.5 mmol) in DCM (75 mL) was treated with MsCl (2.61 mL, 33.5 mmol) at 0° C. After stirring at RT for 16 h, the reaction was done. The reaction was quenched with water. After extraction with DCM (3×20 mL), the combined organic extracts were dried over $Na_2SO_4$, filtered and concentrated. The crude product was purified on an ISCO silica column (80 g), eluting with ethyl acetate:hexanes, 0-70% gradient. The desired fractions were concentrated to yield compound 35 (7.47 g, 26.9 mmol, 88% yield). LCMS ESI: calculated for $C_{14}H_{13}ClNO_3$=278.1 (M+H+), found 278.0 (M+H+). 1H NMR (400 MHz, CHLOROFORM-d) δ 8.19 (d, J=2.2 Hz, 1H), 8.13-8.02 (m, 2H), 7.79 (dd, J=8.5, 2.5 Hz, 1H), 7.22-7.14 (m, 2H), 6.99 (d, J=8.6 Hz, 1H), 4.57 (s, 2H), 3.92 (s, 3H).

Compounds 36 and 37.

Compound 30 (70 mg, 0.339 mmol) in DMF (1 mL) was treated with cesium carbonate (332 mg, 1.018 mmol), followed by compound 35 (94 mg, 0.339 mmol). After stirring for 5 h at RT, the reaction was complete. After quenching with water and extraction with ethyl acetate (3×10 mL), the combined organic extracts were dried over $Na_2SO_4$, filtered and concentrated The crude product was purified on an ISCO silica column (24 g), eluted with 20% MeOH in DCM:DCM, 0-60% gradient. The desired fractions were concentrated to yield a mixture of compounds 36 and 37 (120 mg, 0.080 mmol, 79% yield), in a 1:4 ratio. LCMS ESI: calculated for $C_{23}H_{26}N_7O_3$=448.2 (M+H+), found 448.3 (M+H+).

Compounds 36a and IM-01.

A mixture of compounds 36 and 37 (60 mg, 0.114 mmol) in THF (2 mL) was treated with LiAlH4 (1.0 M in THF, 0.22 mL, 0.22 mmol) slowly at 0° C. under $N_2$. The reaction mixture was stirred at 0° C. for 1 h, at which point LCMS showed completion of the reaction. Reaction was quenched by adding $Na_2SO_4 \cdot 10H_2O$ slowly, followed by MeOH and stirring at RT for 3 h. The solid was filtered off. The filtrate was concentrated. The residue dissolved in DMF and the products were purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 10% B, 10-45% B over 20 minutes, then a 4-minute hold at 100% B; Flow Rate: 20 mL/min. Fraction collection was triggered by MS and UV signals. Fractions containing desired product were combined and dried via centrifugal evaporation.

Analytical Data for Compound IIb-01:

LCMS ESI: calculated for $C_{22}H_{26}N_7O_2$=420.2 (M+H+), found 420.2 (M+H+). $^1$H NMR (500 MHz, DMSO-$d_6$) δ 9.45-9.29 (m, 1H), 8.21-8.15 (m, 1H), 8.13 (s, 1H), 7.86-7.78 (m, 1H), 7.78-7.68 (m, 1H), 7.35 (br d, J=8.2 Hz, 2H), 7.08-7.03 (m, 2H), 7.03-6.99 (m, 1H), 5.52 (s, 2H), 4.50 (br d, J=4.9 Hz, 2H), 2.98-2.82 (m, 2H), 1.65-1.51 (m, 2H), 1.40-1.27 (m, 2H), 0.90 (br t, J=7.2 Hz, 3H).

Compound IIb-04.

A mixture of compound 36a and compound IIb-04 (40 mg, 0.095 mmol) in THF (1 mL) was treated with thionyl chloride (0.14 mL, 1.9 mmol). After stirring at RT for 3 h, LCMS showed completion of the reaction. The solvent was evaporated and the excess thionyl chloride was azeotropically removed with DCM. The crude chloride material was directly carried over to next step without further purification. LCMS ESI: calculated for $C_{22}H_{25}N_7O$=438.2 (M+H+), found 438.1 (M+H+).

A mixture of the preceding chlorides (40 mg, 0.091 mmol) from preceding paragraph was dissolved in DMF (1.0 mL) and treated with 2-aminoethan-1-ol (55.0 μl, 0.91 mmol), followed by stirring at RT for 16 h. LCMS showed completion of the reaction. The mixture was purified via preparative LC/MS with the following conditions: Column: XBridge C18, 200 mm×19 mm, 5-μm particles; Mobile Phase A: 5:95 acetonitrile:water with 10 mM ammonium acetate; Mobile Phase B: 95:5 acetonitrile:water with 10 mM ammonium acetate; Gradient: a 0-minute hold at 8% B, 8-48% B over 25 minutes, then a 4-min hold at 100% B; Flow Rate: 20 mL/min; Column Temperature: 25° C. Fraction collection was triggered by MS signals. Fractions containing the desired product were combined and dried via centrifugal evaporation.

Analytical Data for Compound IIb-04:

LCMS ESI: calculated for $C_{24}H_{31}N_8O_2$=463.2 (M+H+), found 463.3 (M+H+). $^1$H NMR (500 MHz, DMSO-$d_6$) δ 8.18 (br s, 2H), 7.91 (br s, 1H), 7.84 (br d, J=8.7 Hz, 1H), 7.55 (br d, J=8.1 Hz, 2H), 7.18 (br d, J=8.3 Hz, 2H), 7.09 (br d, J=8.7 Hz, 1H), 5.55 (s, 2H), 4.18 (s, 2H), 3.73-3.63 (m, 2H), 3.12-2.74 (m, 4H), 1.69-1.50 (m, 2H), 1.38-1.25 (m, 2H), 0.91 (br t, J=7.3 Hz, 3H).

Replacing 6-fluoronicotinaldehyde 31 with 4-fluoro-2-methoxybenzaldehyde in the scheme of FIGS. 4A-4B and generally following the procedures above, the compounds in Table E were analogously prepared, using the indicated amine.

TABLE E

| Compounds Made Analogously per FIGS. 4A-4B | | | |
|---|---|---|---|
| Cpd. No. | Expected Mass (M + H) | Observed Mass (M + H) | Amine used |
| IIb-02 | 492.3 | 492.1 | 2-Aminoethan-1-ol |
| IIb-03 | 561.3 | 561.4 | 2-(Piperazin-1-yl)ethan-1-ol |

Example 5—Synthesis of Compounds III-01 and III-02

This example relates to the preparation of compounds III-01 and III-02. These compounds were prepared by reacting compounds 36 and 37 with MeMgCl Grignard reagent.

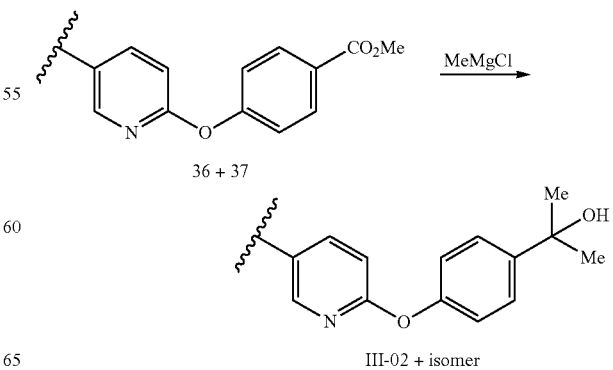

To a mixture of compounds 36 and 37 (60 mg, 0.134 mmol) in THF (1 mL) was added MeMgCl (0.171 mL, 0.513 mmol) at 0° C. After 1 hr, LCMS showed reaction was completed. The mixture was purified via preparative LC/MS with the following conditions: Column: XBridge C18, 200 mm×19 mm, 5-μm particles; Mobile Phase A: 5:95 acetonitrile:water with 0.1% TFA; Mobile Phase B: 95:5 acetonitrile:water with 0.1% TFA; Gradient: a 0-minute hold at 10% B, 10-45% B over 20 minutes, then a 4-minute hold at 100% B; Flow Rate: 20 mL/min; Column Temperature: 25° C. Fraction collection was triggered by MS signals. Fractions containing the desired product were combined and dried via centrifugal evaporation.

Analytical data for III-02.

LCMS ESI: calculated for $C_{24}H_{30}N_7O_2$=448.2 (M+H$^+$), found 448.2 (M+H$^+$). $^1$H NMR (500 MHz, DMSO-d6) δ 8.22 (d, J=1.8 Hz, 1H), 8.06-7.97 (m, 2H), 7.87 (br dd, J=8.5, 2.4 Hz, 2H), 7.23 (d, J=8.8 Hz, 2H), 7.15 (d, J=8.5 Hz, 1H), 5.99-5.97 (m, 1H), 5.56 (s, 2H), 3.58-3.54 (m, 2H), 1.64-1.49 (m, 2H), 1.37-1.25 (m, 2H), 1.17 (s, 6H), 0.90 (t, J=7.4 Hz, 3H), 0.71-0.70 (m, 1H)

The foregoing detailed description of the invention includes passages that are chiefly or exclusively concerned with particular parts or aspects of the invention. It is to be understood that this is for clarity and convenience, that a particular feature may be relevant in more than just the passage in which it is disclosed, and that the disclosure herein includes all the appropriate combinations of information found in the different passages. Similarly, although the various figures and descriptions herein relate to specific embodiments of the invention, it is to be understood that where a specific feature is disclosed in the context of a particular figure or embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

Acronyms and Abbreviations

This is a list of acronyms and abbreviations used in this specification, along with their meanings.

| ACRONYM OR ABBREVIATION | MEANING OR DEFINITION |
| --- | --- |
| Boc | t-Butyloxycarbonyl |
| BOP | (Benzotriazol-1-yloxy)tris(dimethylamino)-phosphonium hexafluorophosphate (V) |
| DBU | 1,8-Diazabicyclo[5.4.0]undec-7-ene |
| DCM | Dichloromethane |
| DIAD | Diisopropyl azodicarboxylate |
| DIPEA, DIEA | N,N-diisopropylethylamine, also known as Hunig's base |
| DMF | N,N-dimethylformamide |
| DMSO | Dimethyl sulfoxide |
| Hunig's base | See DIPEA, DIEA |
| LCMS | Liquid chromatography mass spectrometry |
| MsCl | Methanesylfonyl chloride, mesyl chloride |
| PEG | Poly(ethylene glycol) |
| RT | Room temperature, circa 25° C. |
| TBDPS | tert-Butyldiphenylsilyl |
| TEAA | Triethylammonium acetate |
| TFA | Trifluoroacetic acid |
| THF | Tetrahydrofuran |

REFERENCES

Full citations for the following references cited in abbreviated fashion by first author (or inventor) and date earlier in this specification are provided below. Each of these references is incorporated herein by reference for all purposes.

Akinbobuyi et al., *Tetrahedron Lett.* 2015, 56, 458, "Facile syntheses of functionalized toll-like receptor 7 agonists".
Akinbobuyi et al., *Bioorg. Med. Chem. Lett.* 2016, 26, 4246, "Synthesis and immunostimulatory activity of substituted TLR7 agonists."
Barberis et al., US 2012/0003298 A1 (2012).
Beesu et al., *J. Med. Chem.* 2017, 60, 2084, "Identification of High-Potency Human TLR8 and Dual TLR7/TLR8 Agonists in Pyrimidine-2,4-diamines."
Berghöfer et al., *J. Immunol.* 2007, 178, 4072, "Natural and Synthetic TLR7 Ligands Inhibit CpG-A- and CpG-C-Oligodeoxynucleotide-Induced IFN-α Production."
Bonfanti et al., US 2014/0323441 A1 (2015) [2015a].
Bonfanti et al., US 2015/0299221 A1 (2015) [2015b].
Bonfanti et al., US 2016/0304531 A1 (2016).
Carson et al., US 2013/0202629 A1 (2013).
Carson et al., U.S. Pat. No. 8,729,088 B2 (2014).
Carson et al., U.S. Pat. No. 9,050,376 B2 (2015).
Carson et al., US 2016/0199499 A1 (2016).
Chan et al., *Bioconjugate Chem.* 2009, 20, 1194, "Synthesis and Immunological Characterization of Toll-Like Receptor 7 Agonistic Conjugates."
Chan et al., *Bioconjugate Chem.* 2011, 22, 445, "Synthesis and Characterization of PEGylated Toll Like Receptor 7 Ligands."
Chen et al., U.S. Pat. No. 7,919,498 B2 (2011).
Coe et al., U.S. Pat. No. 9,662,336 B2 (2017).
Cortez and Va, *Medicinal Chem. Rev.* 2018, 53, 481, "Recent Advances in Small-Molecule TLR7 Agonists for Drug Discovery".
Cortez et al., US 2017/0121421 A1 (2017).
Cortez et al., U.S. Pat. No. 9,944,649 B2 (2018).
Dellaria et al., WO 2007/028129 A1 (2007).
Desai et al., U.S. Pat. No. 9,127,006 B2 (2015).
Ding et al., WO 2016/107536 A1 (2016).
Ding et al., US 2017/0273983 A1 (2017) [2017a].
Ding et al., WO 2017/076346 A1 (2017) [2017b].
Gadd et al., *Bioconjugate Chem.* 2015, 26, 1743, "Targeted Activation of Toll-Like Receptors: Conjugation of a Toll-Like Receptor 7 Agonist to a Monoclonal Antibody Maintains Antigen Binding and Specificity."
Graupe et al., U.S. Pat. No. 8,993,755 B2 (2015).
Embrechts et al., *J. Med. Chem.* 2018, 61, 6236, "2,4-Diaminoquinazolines as Dual Toll Like Receptor (TLR) 7/8 Modulators for the Treatment of Hepatitis B Virus."
Halcomb et al., U.S. Pat. No. 9,161,934 B2 (2015).
Hashimoto et al., US 2009/0118263 A1 (2009).
He et al., US 2019/0055246 A1 (2019) [2019a].
He et al., US 2019/0055247 A1 (2019) [2019b].
Hirota et al., U.S. Pat. No. 6,028,076 (2000).
Holldack et al., US 2012/0083473 A1 (2012).

Isobe et al., U.S. Pat. No. 6,376,501 B1 (2002).
Isobe et al., JP 2004137157 (2004).
Isobe et al., *J. Med. Chem.* 2006, 49 (6), 2088, "Synthesis and Biological Evaluation of Novel 9-Substituted-8-Hydroxyadenine Derivatives as Potent Interferon Inducers."
Isobe et al., U.S. Pat. No. 7,521,454 B2 (2009) [2009a].
Isobe et al., US 2009/0105212 A1 (2009) [2009b].
Isobe et al., US 2011/0028715 A1 (2011).
Isobe et al., U.S. Pat. No. 8,148,371 B2 (2012).
Jensen et al., WO 2015/036044 A1 (2015).
Jones et al., U.S. Pat. No. 7,691,877 B2 (2010).
Jones et al., US 2012/0302598 A1 (2012).
Kasibhatla et al., U.S. Pat. No. 7,241,890 B2 (2007).
Koga-Yamakawa et al., *Int. J. Cancer* 2013, 132 (3), 580, "Intratracheal and oral administration of SM-276001: A selective TLR7 agonist, leads to antitumor efficacy in primary and metastatic models of cancer."
Li et al., U.S. Pat. No. 9,902,730 B2 (2018).
Lioux et al., U.S. Pat. No. 9,295,732 B2 (2016).
Lund et al., *Proc. Nat'l Acad. Sci* (USA) 2004, 101 (15), 5598, "Recognition of single-stranded RNA viruses by Toll-like receptor 7."
Maj et al., U.S. Pat. No. 9,173,935 B2 (2015).
McGowan et al., US 2016/0168150 A1 (2016) [2016a].
McGowan et al., U.S. Pat. No. 9,499,549 B2 (2016) [2016b].
McGowan et al., *J. Med. Chem.* 2017, 60, 6137, "Identification and Optimization of Pyrrolo[3,2-d]pyrimidine Toll-like Receptor 7 (TLR7) Selective Agonists for the Treatment of Hepatitis B."
Musmuca et al., *J. Chem. Information &Modeling* 2009, 49 (7), 1777, "Small-Molecule Interferon Inducers. Toward the Comprehension of the Molecular Determinants through Ligand-Based Approaches."
Nakamura et al., *Bioorg. Med. Chem. Lett.* 2013, 13, 669, "Synthesis and evaluation of 8-oxoadenine derivatives as potent Toll-like receptor agonists with high water solubility."
Ogita et al., US 2007/0225303 A1 (2007).
Ota et al., WO 2019/124500 A1 (2019).
Pilatte et al., WO 2017/216293 A1 (2017).
Poudel et al., US 2019/0055243 A1 (2019) [2019a].
Poudel et al., US 2019/0055245 A1 (2019) [2019b].
Purandare et al., PCT Application Ser. No. PCT/US19/28697, filed Apr. 23, 2019.
Pryde, U.S. Pat. No. 7,642,350 B2 (2010).
Sato-Kaneko et al., *JCI Insight* 2017, 2, e93397, "Combination Immunotherapy with TLR Agonists and Checkpoint Inhibitors Suppresses Head and Neck Cancer".
Smits et al., *The Oncologist* 2008, 13, 859, "The Use of TLR7 and TLR8 Ligands for the Enhancement of Cancer Immunotherapy".
Vasilakos and Tomai, *Expert Rev. Vaccines* 2013, 12, 809, "The Use of Toll-like Receptor 7/8 Agonists as Vaccine Adjuvants".
Vemejoul et al., US 2014/0141033 A1 (2014).
Young et al., US 2019/0055244 A1 (2019).
Yu et al., *PLoS One* 2013, 8 (3), e56514, "Toll-Like Receptor 7 Agonists: Chemical Feature Based Pharmacophore Identification and Molecular Docking Studies."
Zhang et al., *Immunity* 2016, 45, 737, "Structural Analysis Reveals that Toll-like Receptor 7 Is a Dual Receptor for Guanosine and Single-Stranded RNA."
Zhang et al., WO 2018/095426 A1 (2018)>
Zurawski et al., US 2012/0231023 A1 (2012).

What is claimed is:

1. A compound having a structure according to formula II

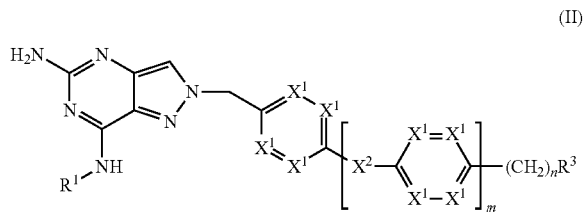

wherein
each $X^1$ is independently N or $CR^2$;
$X^2$ is O, $CH_2$, NH, S, or $N(C_1$-$C_3$ alkyl);
$R^1$ is H, $CH_3(CH_2)_{1\text{-}3}$, $CH_3(CH_2)_{0\text{-}1}O(CH_2)_{2\text{-}3}$, $CH_3(CH_2)_{0\text{-}3}C(=O)$, $CH_3(CH_2)_{0\text{-}1}O(CH_2)_{2\text{-}3}C(=O)$,

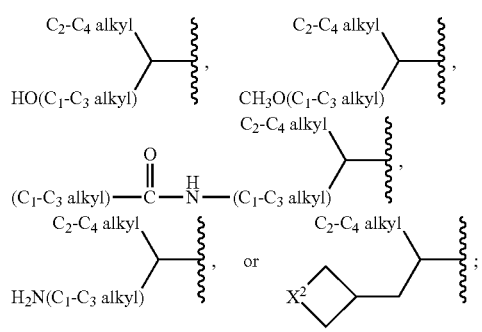

$R^2$ is H, $O(C_1$-$C_3$ alkyl), $C_1$-$C_3$ alkyl, Cl, F, or CN;
$R^3$ is H, halo, OH, CN, $NH_2$, $NH(C_1$-$C_5$ alkyl), $N(C_1$-$C_5$ alkyl)$_2$, $NH(CH_2)_{0\text{-}1}(C_3$-$C_6$ cycloalkyl), $NH(C_4$-$C_8$ bicycloalkyl), $NH(C_6$-$C_{10}$ spirocycloalkyl), $N(C_3$-$C_6$ cycloalkyl)$_2$, $NH(CH_2)_{1\text{-}3}$(aryl), $N((CH_2)_{1\text{-}3}$(aryl))$_2$, a cyclic amine moiety having the structure

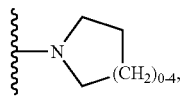

a 6-membered aromatic or heteroaromatic moiety or a 5-membered heteroaromatic moiety;
wherein
an alkyl, cycloalkyl, bicycloalkyl, spirocycloalkyl, cyclic amine, 6-membered aromatic or heteroaromatic, or 5-membered heteroaromatic moiety is optionally substituted with one or more substituents selected from OH, halo, CN, ($C_1$-$C_3$ alkyl), O($C_1$-$C_3$ alkyl), C(=O)(Me), $SO_2(C_1$-$C_3$ alkyl), C(=O)(Et), $NH_2$, NH(Me), N(Me)$_2$, NH(Et), N(Et)$_2$, and N($C_1$-$C_3$ alkyl), $(CH_2)_{1\text{-}2}OH$, $(CH_2)_{1\text{-}2}OMe$; and
a cycloalkyl, bicycloalkyl, spirocycloalkyl, or cyclic amine moiety may have a $CH_2$ group replaced by O, S, $SO_2$, NH, C(=O), N($C_1$-$C_3$ alkyl), NC(=O)($C_1$-$C_3$ alkyl), or N(Boc); m is 0 or 1; and n is 1, 2, or 3.

2. A compound according to claim 1, wherein the group $R^1$ is

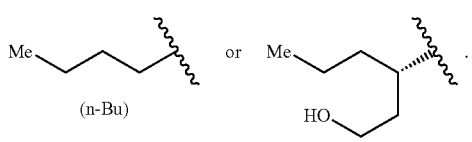 [SMILES: *CCCC ; *[C@@H](CCC)CCO]
(n-Bu)
3. A compound according to claim 1, wherein, in the moiety
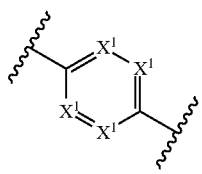
either each $X^1$ is $CR^2$ or not more than two $X^1$'s are N.
4. A compound according to claim 1, wherein the moiety
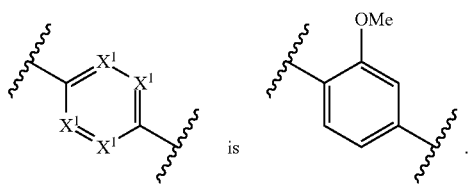
5. A compound according to claim 1, wherein the group $R^3$ is selected from the group consisting of Cl, H,
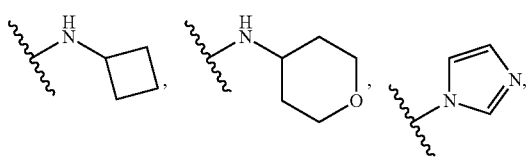
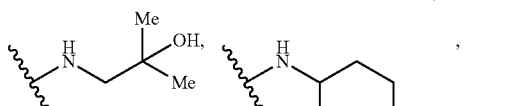
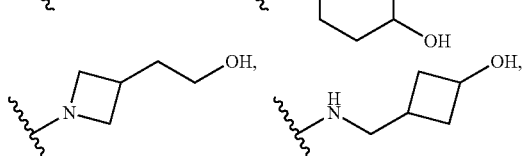
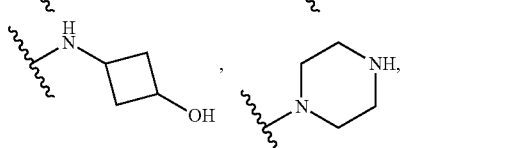
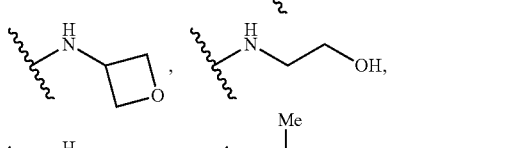
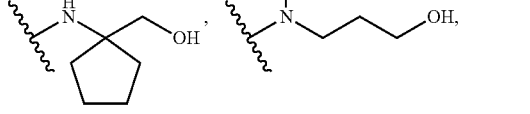
-continued
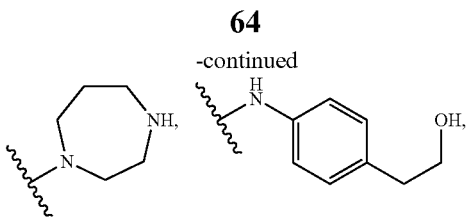
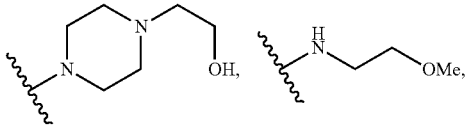
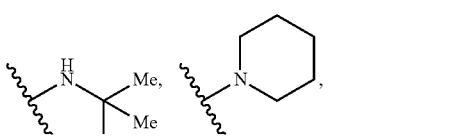
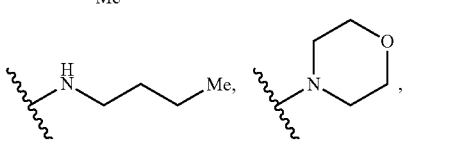
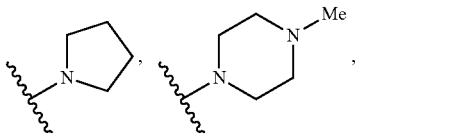
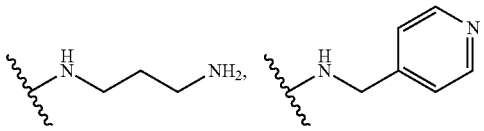
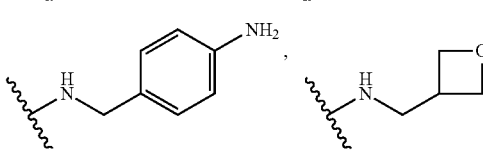
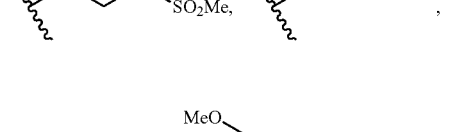
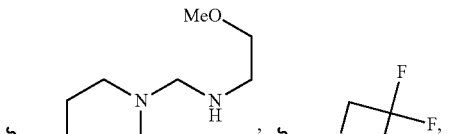
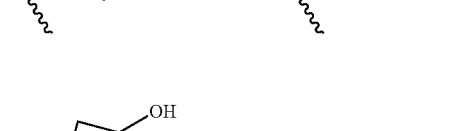
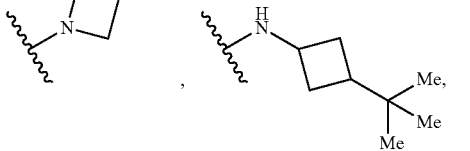

-continued

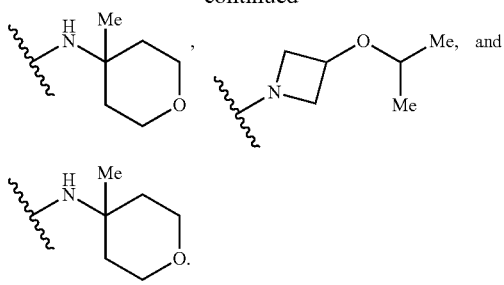

6. A compound according to claim 1, having a structure according to formula (II')

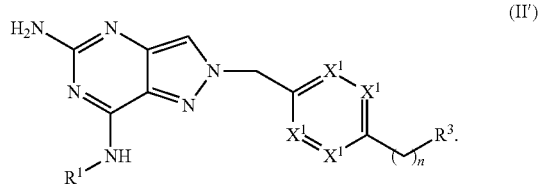
(II')

7. A compound according to claim 1, having a structure according to formula IIa

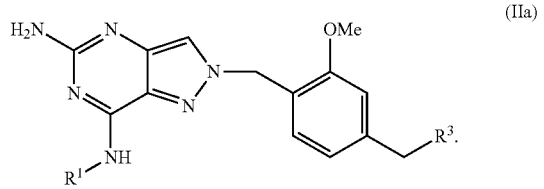
(IIa)

8. A compound according to claim 1, having a structure according to formula IIb

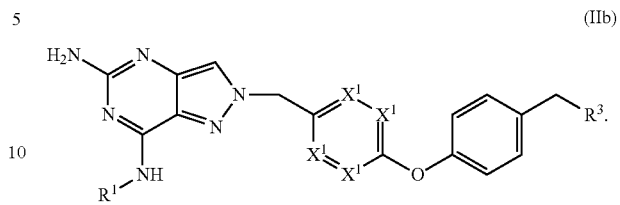
(IIb)

9. A compound according to claim 1, which is covalently bonded to a poly(ethylene glycol) moiety between 2 kDa and 40 kDa in size.

10. A method of treating cancer, comprising administering to a patient suffering from such cancer a therapeutically effective combination of an anti-cancer immunotherapy agent and a compound according to claim 1.

11. A method according to claim 10, wherein the anti-cancer immunotherapy agent is an antagonistic anti-CTLA-4, anti-PD-1, or anti-PD-L1 antibody.

12. A method according to claim 11, wherein the cancer is lung cancer, pancreatic cancer, kidney cancer, head and neck cancer, lymphoma, skin cancer, urothelial cancer, gastric cancer, hepatocellular cancer, or colorectal cancer.

13. A method according to claim 11, wherein the anti-cancer immunotherapy agent is ipilimumab, nivolumab, or pembrolizumab.

14. A method according to claim 12, wherein the lung cancer is non-small cell lung cancer.

15. A method according to claim 12, wherein the lymphoma is Hodgkin's lymphoma.

16. A method according to claim 12, wherein the skin cancer is melanoma.

17. A method according to claim 12, wherein the skin cancer is Merkel skin cancer.

18. A method according to claim 12, wherein the urothelial cancer is bladder cancer.

\* \* \* \* \*